(12) United States Patent
Chen

(10) Patent No.: US 7,687,518 B2
(45) Date of Patent: Mar. 30, 2010

(54) THERAPEUTIC AGENTS USEFUL FOR TREATING PAIN

(75) Inventor: Zhengming Chen, Belle Mead, NJ (US)

(73) Assignee: Purdue Pharma L.P., Stamford, CT (US)

( * ) Notice: Subject to any disclaimer, the term of this patent is extended or adjusted under 35 U.S.C. 154(b) by 155 days.

(21) Appl. No.: 11/729,660

(22) Filed: Mar. 28, 2007

(65) Prior Publication Data

US 2007/0179141 A1 Aug. 2, 2007

Related U.S. Application Data

(62) Division of application No. 10/714,066, filed on Nov. 13, 2003, now Pat. No. 7,202,259.

(60) Provisional application No. 60/427,381, filed on Nov. 18, 2002, provisional application No. 60/460,278, filed on Apr. 3, 2003, provisional application No. 60/488,488, filed on Jul. 17, 2003.

(51) Int. Cl.
*A61K 31/445* (2006.01)
*C07D 401/04* (2006.01)

(52) U.S. Cl. ............ 514/315; 514/317; 514/326; 546/184; 546/192; 546/208; 546/210

(58) Field of Classification Search .......... 514/326, 514/315, 317; 546/184, 192, 208, 210
See application file for complete search history.

(56) References Cited

U.S. PATENT DOCUMENTS 6,423,519 B1 * 7/2002 Bergnes et al. ............ 435/193

\* cited by examiner

*Primary Examiner*—Rebecca L Anderson
(74) *Attorney, Agent, or Firm*—Dechert LLP

(57) ABSTRACT

4-Tetrazolyl-4-phenylpiperidine Compounds, compositions comprising an effective amount of a 4-Tetrazolyl-4-phenylpiperidine Compound, methods for treating or preventing pain or diarrhea in an animal comprising administering to an animal in need thereof an effective amount of a 4-Tetrazolyl-4-phenylpiperidine Compound and methods for stimulating opioid-receptor function in a cell comprising contacting a cell capable of expressing an opioid receptor with an effective amount of a 4-Tetrazolyl-4-phenylpiperidine Compound are disclosed.

23 Claims, No Drawings

THERAPEUTIC AGENTS USEFUL FOR TREATING PAIN

This application is a divisional of application Ser. No. 10/714,066, filed Nov. 13, 2003 now U.S. Pat. No. 7,202,259, which claims the benefit of U.S. provisional application Ser. No. 60/427,381, filed Nov. 18, 2002, U.S. provisional application Ser. No. 60/460,278, filed Apr. 3, 2003, and U.S. provisional application Ser. No. 60/488,488 filed Jul. 17, 2003, the entire disclosure of each of which is incorporated by reference herein in its entirety.

1. FIELD OF THE INVENTION

The present invention relates to 4-Tetrazolyl-4-phenylpiperidine Compounds, compositions comprising an effective amount of a 4-Tetrazolyl-4-phenylpiperidine Compound and methods for preventing or treating pain or diarrhea in an animal comprising administering to an animal in need of such treatment or prevention an effective amount of a 4-Tetrazolyl-4-phenylpiperidine Compound.

2. BACKGROUND OF THE INVENTION

Pain is the most common symptom for which patients seek medical advice and treatment. Pain can be acute or chronic. While acute pain is usually self-limited, chronic pain can persist for 3 months or longer and lead to significant changes in a patient's personality, lifestyle, functional ability or overall quality of life (K. M. Foley, Pain, in *Cecil Textbook of Medicine* 100-107, J. C. Bennett and F. Plum eds., 20th ed. 1996).

Pain has been traditionally managed by administering a non-opioid analgesic, such as acetylsalicylic acid, choline magnesium trisalicylate, acetaminophen, ibuprofen, fenoprofen, diflusinal and naproxen; or an opioid analgesic, such as morphine, hydromorphone, methadone, levorphanol, fentanyl, oxycodone and oxymorphone. Id.

U.S. Pat. No. 6,576,650 B1, U.S. Pat. No. 6,166,039, and U.S. Pat. No. 5,849,761, to Yaksh and U.S. Pat. No. 6,573,282, to Yaksh et al. describe 1,4 substituted piperidine derivatives allegedly useful as peripherally active anti hyperalgesic opiates.

U.S. Pat. No. 6,362,203 B1 to Mogi et al. describes 4 hydroxy-4-phenylpiperidine derivatives that are alleged to exhibit peripheral analgesic action.

Canadian Patent Publication No. 949560 of Carron et al. describes piperidine derivatives bearing substituents at the 1 and 4 positions that are alleged to be useful as analgesics.

International Publication No. WO 02/38185 A2 of Dunn et al. describes 1,4-substituted piperidine compounds that are allegedly useful as an antihyperalgesic opiate.

The Abstract of International Publication No. WO 01/70689 A1 also discloses piperidine derivatives carrying substituents at the 1 and 4 positions that are allegedly useful as opioid δ receptor agonists.

Traditional opioid analgesics exert their pharmacological activity once they have passed through the blood-brain barrier. But this blood-brain barrier passage can lead to undesirable central nervous system-mediated side effects, such as respiratory depression, increased drug tolerance, increased drug dependence, constipation and unwanted euphoria.

There remains a clear need for new drugs that are useful for treating or preventing pain or diarrhea and that reduce or avoid one or more side effects associated with traditional therapy for treating pain or diarrhea.

Citation of any reference in Section 2 of this application is not an admission that such reference is prior art to the present application.

3. SUMMARY OF THE INVENTION

The present invention encompasses compounds having the formula (Ia):

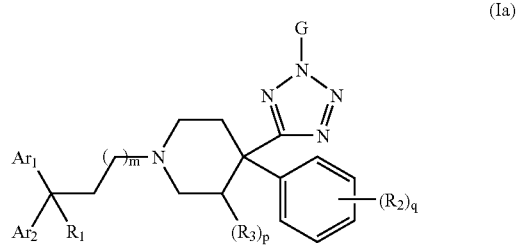

(Ia)

and pharmaceutically acceptable salts thereof, wherein:

$Ar_1$ is $-C_3-C_8$ cycloalkyl, phenyl, naphthyl, anthryl, phenanthryl or -(5- to 7-membered) heteroaryl, each being unsubstituted or substituted with one or more $R_2$ groups;

$Ar_2$ is phenyl, naphthyl, anthryl, phenanthryl or -(5- to 7-membered) heteroaryl, each being unsubstituted or substituted with one or more $R_2$ groups;

G is $-H$, $-L-(CH_2)_nCO_2R_4$, $-L-(CH_2)_nR_5$, $-(C_1-C_5$ alkylene$)CO_2R_4$, or $-(C_1-C_5$ alkylene$)R_5$;

$L=-C(O)-$, $-SO_2-$ or $-SO-$;

$R_1=-H$, $-C(O)NH_2$, $-C(O)NHOH$, $-CO_2R_4$, $-CHO$, $-CN$, $-(C_1-C_4$ alkyl), $-C(O)NH(C_1-C_4$ alkyl), $-C(O)N(C_1-C_4$ alkyl$)_2$,

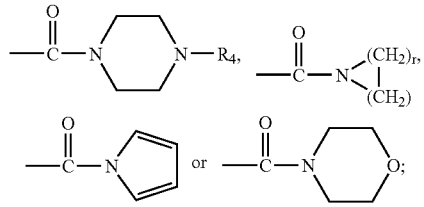

$R_2$ and $R_3$ are each independently -halogen, $-C_1-C_3$ alkyl, $-O(C_1-C_3$ alkyl), $-NH(C_1-C_3$ alkyl) or $-N(C_1-C_3$ alkyl$)_2$;

$R_4=-H$, $-C_1-C_{10}$ alkyl, $-CH_2O(C_1-C_4$ alkyl), $-CH_2N(C_1-C_4$ alkyl$)_2$, or $-CH_2NH(C_1-C_4$ alkyl);

$R_5=-NH_2$, $-NHSO_2R_4$, $-C(O)NH_2$, $-C(O)NHOH$, $-SO_2NH_2$, $-C(O)NH(C_1-C_4$ alkyl), $-C(O)N(C_1-C_4$ alkyl$)_2$, $-SO_2NH(C_1-C_4$ alkyl), $-SO_2N(C_1-C_4$ alkyl$)_2$, $-H$, $-OH$, $-CN$, $-C_3-C_8$ cycloalkyl, phenyl, naphthyl, anthryl, phenanthryl, or -(5- to 7-membered) heteroaryl, each being unsubstituted or substituted with one or more $R_2$ groups;

m=an integer ranging from 0 to 4;

n=an integer ranging from 1 to 4;

p=0 or 1;

q=an integer ranging from 0 to 3; and r=an integer ranging from 1 to 6.

The present invention also encompasses compounds having the formula (Ib):

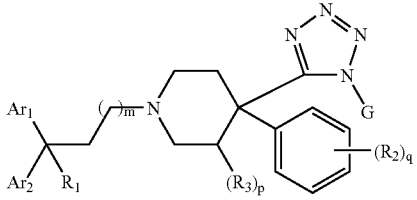

(Ib)

and pharmaceutically acceptable salts thereof, wherein:

Ar$_1$ is —C$_3$-C$_8$ cycloalkyl, phenyl, naphthyl, anthryl, phenanthryl, or -(5- to 7-membered) heteroaryl, each being unsubstituted or substituted with one or more R$_2$ groups;

Ar$_2$ is phenyl, naphthyl, anthryl, phenanthryl, or -(5- to 7-membered) heteroaryl, each being unsubstituted or substituted with one or more R$_2$ groups;

G=H, -L(CH$_2$)$_n$C(O)OR$_4$, -L(CH$_2$)$_n$R$_5$, —(C$_1$-C$_5$ alkylene)COOR$_4$, or —(C$_1$-C$_5$ alkylene)R$_5$;

L=—C(O)—, —SO$_2$—, or —SO—;

R$_1$=H, —C(O)NH$_2$, —C(O)NHOH, —CO$_2$R$_4$, —CHO, —CN, —(C$_1$-C$_4$ alkyl), —C(O)NH(C$_1$-C$_4$ alkyl), —C(O)N(C$_1$-C$_4$ alkyl)$_2$,

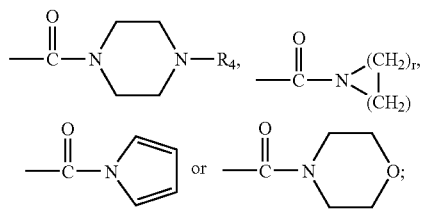

R$_2$ and R$_3$ are each independently halogen, —C$_1$-C$_3$ alkyl, —O(C$_1$-C$_3$ alkyl), —NH(C$_1$-C$_3$ alkyl), or —N(C$_1$-C$_3$ alkyl)$_2$;

R$_4$=—H, —C$_1$-C$_{10}$ alkyl, —CH$_2$O(C$_1$-C$_4$ alkyl), —CH$_2$N(C$_1$-C$_4$ alkyl)$_2$, or —CH$_2$NH(C$_1$-C$_4$ alkyl);

R$_5$=—NH$_2$, —NHSO$_2$R$_4$, —C(O)NH$_2$, —C(O)NHOH, —SO$_2$NH$_2$, —C(O)NH(C$_1$-C$_4$ alkyl), —C(O)N(C$_1$-C$_4$ alkyl)$_2$, —SO$_2$NH(C$_1$-C$_4$ alkyl), —SO$_2$N(C$_1$-C$_4$ alkyl)$_2$, —H, —OH, —CN, —C$_3$-C$_8$ cycloalkyl, phenyl, naphthyl, anthryl, phenanthryl, or -(5- to 7-membered) heteroaryl, each being unsubstituted or substituted with one or more R$_2$ groups;

m=an integer ranging from 0 to 4;
n=an integer ranging from 1 to 4;
p=0 or 1;
q=an integer ranging from 0 to 3; and
r=an integer ranging from 1 to 6.

The present invention also encompasses compounds having the formula (Ic):

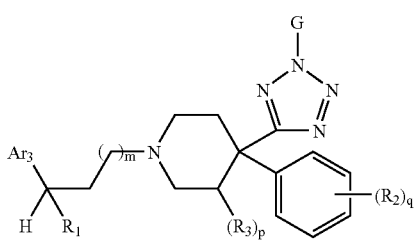

(Ic)

and pharmaceutically acceptable salts thereof, wherein:

Ar$_3$ is phenyl, naphthyl, anthryl, phenanthryl, or -(5- to 7-membered) heteroaryl, each being unsubstituted or substituted with one or more R$_2$ groups;

G=H, -L(CH$_2$)$_n$C(O)OR$_4$, -L(CH$_2$)$_n$R$_5$, —(C$_1$-C$_5$ alkylene)COOR$_4$, or —(C$_1$-C$_5$ alkylene)R$_5$;

L=—C(O)—, —SO$_2$—, or —SO—;

R$_1$=—H, —C(O)NH$_2$, —C(O)NHOH, —CO$_2$R$_4$, —CHO, —CN, —(C$_1$-C$_4$ alkyl), —C(O)NH(C$_1$-C$_4$ alkyl), —C(O)N(C$_1$-C$_4$ alkyl)$_2$,

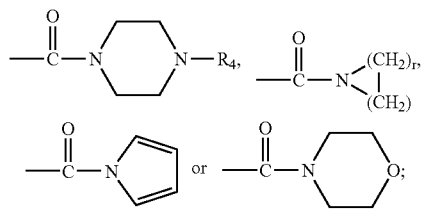

R$_2$ and R$_3$ are each independently halogen, —C$_1$-C$_3$ alkyl, —O(C$_1$-C$_3$ alkyl), —NH(C$_1$-C$_3$ alkyl), or —N(C$_1$-C$_3$ alkyl)$_2$;

R$_4$=—H, —C$_1$-C$_{10}$ alkyl, —CH$_2$O(C$_1$-C$_4$ alkyl), —CH$_2$N(C$_1$-C$_4$ alkyl)$_2$, or —CH$_2$NH(C$_1$-C$_4$ alkyl);

R$_5$=—NH$_2$, —NHSO$_2$R$_4$, —C(O)NH$_2$, —C(O)NHOH, —SO$_2$NH$_2$, —C(O)NH(C$_1$-C$_4$ alkyl), —C(O)N(C$_1$-C$_4$ alkyl)$_2$, —SO$_2$NH(C$_1$-C$_4$ alkyl), —SO$_2$N(C$_1$-C$_4$ alkyl)$_2$, —H, —OH, —CN, —C$_3$-C$_8$ cycloalkyl, phenyl, naphthyl, anthryl, phenanthryl, or -(5- to 7-membered) heteroaryl, each being unsubstituted or substituted with one or more R$_2$ groups;

m=an integer ranging from 0 to 4;
n=an integer ranging from 1 to 4;
p=0 or 1;
q=an integer ranging from 0 to 3; and
r=an integer ranging from 1 to 6.

The present invention also encompasses compounds having the formula (Id):

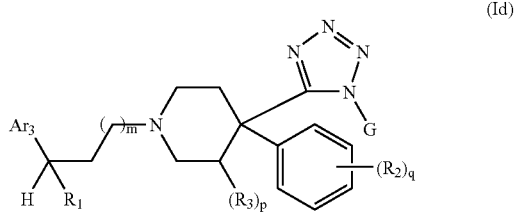

(Id)

and pharmaceutically acceptable salts thereof, wherein:

Ar$_3$ is phenyl, naphthyl, anthryl, phenanthryl, or -(5- to 7-membered) heteroaryl, each being unsubstituted or substituted with one or more R$_2$ groups;

G=H, -L(CH$_2$)$_n$C(O)OR$_4$, -L(CH$_2$)$_n$R$_5$, —(C$_1$-C$_5$ alkylene)COOR$_4$, or —(C$_1$-C$_5$ alkylene)R$_5$;

L=—C(O)—, —SO$_2$—, or —SO—;

R$_1$=—H, —C(O)NH$_2$, —C(O)NHOH, —CO$_2$R$_4$, —CHO, —CN, —(C$_1$-C$_4$ alkyl), —C(O)NH(C$_1$-C$_4$ alkyl), —C(O)N(C$_1$-C$_4$ alkyl)$_2$,

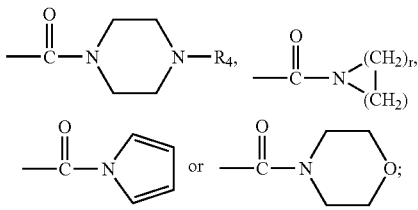

R$_2$ and R$_3$ are each independently halogen, —C$_1$-C$_3$ alkyl, —O(C$_1$-C$_3$ alkyl), —NH(C$_1$-C$_3$ alkyl), or —N(C$_1$-C$_3$ alkyl)$_2$;

R$_4$=—H, —C$_1$-C$_{10}$ alkyl, —CH$_2$O(C$_1$-C$_4$ alkyl), —CH$_2$N(C$_1$-C$_4$ alkyl)$_2$, or —CH$_2$NH(C$_1$-C$_4$ alkyl);

R$_5$=—NH$_2$, —NHSO$_2$R$_4$, —C(O)NH$_2$, —C(O)NHOH, —SO$_2$NH$_2$, —C(O)NH(C$_1$-C$_4$ alkyl), —C(O)N(C$_1$-C$_4$ alkyl)$_2$, —SO$_2$NH(C$_1$-C$_4$ alkyl), —SO$_2$N(C$_1$-C$_4$ alkyl)$_2$, —H, —OH, —CN, —C$_3$-C$_8$ cycloalkyl, phenyl, naphthyl, anthryl, phenanthryl, or -(5- to 7-membered) heteroaryl, each being unsubstituted or substituted with one or more R$_2$ groups;

m=an integer ranging from 0 to 4;
n=an integer ranging from 1 to 4;
p=0 or 1;
q=an integer ranging from 0 to 3; and
r=an integer ranging from 1 to 6.

A compound of formula (Ia), (Ib), (Ic), (Id) or a pharmaceutically acceptable salt thereof (each being a "4-Tetrazolyl-4-phenylpiperidine Compound") is useful for treating or preventing pain or diarrhea in an animal.

The invention also relates to compositions comprising an effective amount of a 4-Tetrazolyl-4-phenylpiperidine Compound and a pharmaceutically acceptable carrier or excipient. The present compositions are useful for treating or preventing pain or diarrhea in an animal.

The invention also relates to kits comprising a container containing an effective amount of a 4-Tetrazolyl-4-phenylpiperidine Compound and instructions for using it to treat or prevent pain or diarrhea.

The invention further relates to methods for preventing pain or diarrhea in an animal, comprising administering to an animal in need thereof an effective amount of a 4-Tetrazolyl-4-phenylpiperidine Compound.

The invention further relates to methods for treating pain or diarrhea in an animal, comprising administering to an animal in need thereof an effective amount of a 4-Tetrazolyl-4-phenylpiperidine Compound.

The invention still further relates to methods for stimulating opioid-receptor function in a cell, comprising contacting a cell capable of expressing an opioid receptor with an effective amount of a 4-Tetrazolyl-4-phenylpiperidine Compound.

The invention still further relates to methods for preparing a pharmaceutical composition, comprising the step of admixing a 4-Tetrazolyl-4-phenylpiperidine Compound and a pharmaceutically acceptable carrier or excipient.

The present invention may be understood more fully by reference to the following detailed description and illustrative examples, which are intended to exemplify non-limiting embodiments of the invention.

4. DETAILED DESCRIPTION OF THE INVENTION

4.1 Definitions

As used herein, the terms used above having following meaning:

"—C$_1$-C$_3$ alkyl" means a straight or branched non cyclic hydrocarbon chain having from 1 to 3 carbon atoms. Representative straight chain and branched chain —C$_1$-C$_3$ alkyls include -methyl, -ethyl, -n-propyl and isopropyl.

"—C$_1$-C$_4$ alkyl" means a straight or branched non-cyclic hydrocarbon chain having from 1 to 4 carbon atoms. Representative straight chain —C$_1$-C$_4$ alkyls include methyl, -ethyl, -n-propyl, and -n-butyl. Representative branched chain —C$_1$-C$_4$ alkyls include -isopropyl, -sec-butyl, -isobutyl, and -tert-butyl.

"—C$_1$-C$_6$ alkyl" means a straight or branched non-cyclic hydrocarbon chain having from 1 to 6 carbon atoms. Representative straight chain —C$_1$-C$_6$ alkyls include methyl, -ethyl, -n-propyl, -n-butyl, -n-pentyl and -n-hexyl. Representative branched chain —C$_1$-C$_6$ alkyls include -isopropyl, -sec-butyl, -isobutyl, -tert-butyl, -isopentyl, -neopentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl and 3,3-dimethylbutyl.

"—(C$_1$-C$_{10}$)alkyl" means a straight chain or branched non-cyclic hydrocarbon having from 1 to 10 carbon atoms. Representative straight chain —(C$_1$-C$_{10}$) alkyls include methyl, -ethyl, -n-propyl, -n-butyl, -n-pentyl, -n-hexyl, -n-heptyl, -n-octyl, -n-nonyl, and -n-decyl. Representative branched —(C$_1$-C$_{10}$) alkyls include isopropyl, sec-butyl, isobutyl, -tert-butyl, isopentyl, neopentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-methylhexyl, 2-methylhexyl, 3-methylhexyl, 4-methylhexyl, 5-methylhexyl, 1,2-dimethylpentyl, 1,3-dimethylpentyl, 1,2-dimethylhexyl, 1,3-dimethylhexyl, 3,3-dimethylhexyl, 1,2-dimethylheptyl, 1,3-dimethylheptyl, and 3,3-dimethylheptyl.

"—C$_1$-C$_5$ alkylene" means a straight chain or branched, non-cyclic, divalent hydrocarbon having from 1 to 5 carbon atoms. Representative straight chain —C$_1$-C$_5$ alkylene groups are —CH$_2$—, —(CH$_2$)$_2$—, —(CH$_2$)$_3$—, —(CH$_2$)$_4$— and —(CH$_2$)$_5$—. Representative branched —C$_2$-C$_5$ alkylene groups include —CH(CH$_3$)—, —C(CH$_3$)$_2$— —CH(CH$_3$)CH$_2$—, —CH$_2$CH(CH$_3$)—, —CH$_2$C(CH$_3$)$_2$—, —C(CH$_3$)$_2$CH$_2$—, —CH(CH$_3$)CH(CH$_3$)—, —CH$_2$C(CH$_3$)$_2$CH$_2$—, —(CH$_2$)$_2$C(CH$_3$)$_2$—, —(CH$_3$)$_2$(CH$_2$)$_2$C— and —CH(CH$_3$)CH$_2$CH(CH$_3$)—.

"—C$_3$-C$_8$ cycloalkyl" means a saturated cyclic hydrocarbon having from 3 to 8 carbon atoms. Representative —C$_3$-C$_8$ cycloalkyls are -cyclopropyl, -cyclobutyl, -cyclopentyl, -cyclohexyl, -cycloheptyl and -cyclooctyl.

"-(5- to 7-membered)heteroaryl" means an aromatic heterocycle ring of 5 to 7 members, wherein at least one carbon atom of the ring is replaced with a heteroatom independently selected from nitrogen, oxygen, and sulfur. The -(5- to 7-membered)heteroaryl's ring contains at least one carbon atom. Representative -(5- to 7-membered)heteroaryls include pyridyl, furyl, thiophenyl, pyrrolyl, oxazolyl, imidazolyl, thiazolyl, isoxazolyl, pyrazolyl, isothiazolyl, pyridazinyl, pyrimidinyl, pyrazinyl, thiadiazolyl, and triazinyl.

"-Halogen" means —F, —Cl, —Br, or —I.

The term "animal," includes, but is not limited to, a cow, ape, monkey, chimpanzee, baboon, horse, sheep, pig, chicken, turkey, quail, cat, dog, mouse, rat, rabbit, guinea pig and human.

The phrase "pharmaceutically acceptable salt," as used herein, is a salt formed from an acid and the basic nitrogen group of a 4-Tetrazolyl-4-phenylpiperidine Compound. Illustrative salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. The term "pharmaceutically acceptable salt" also refers to a salt of a 4-Tetrazolyl-4-phenylpiperidine Compound having an acidic functional group, such as a carboxylic acid functional group, and a pharmaceutically acceptable inorganic or organic base. Illustrative bases include, but are not limited to, hydroxides of alkali metals such as sodium, potassium and lithium; hydroxides of alkaline earth metal such as calcium and magnesium; hydroxides of other metals, such as aluminum and zinc; ammonia; and organic amines, such as unsubstituted or hydroxy substituted mono-, di-, or trialkylamines; dicyclohexylamine; tributylamine; pyridine; N-methyl-N-ethylamine; diethylamine; triethylamine; mono-, bis- or tris-(2-hydroxy-lower alkyl amines), such as mono- bis- or tris-(2-hydroxyethyl)amine, 2-hydroxy-tert-butylamine, or tris-(hydroxymethyl)methylamine, N,N-di-lower alkyl-N-(hydroxy lower alkyl)-amines, such as N,N-dimethyl-N-(2-hydroxyethyl)amine, or tri-(2-hydroxyethyl)amine; N-methyl-D-glucamine; and amino acids such as arginine, lysine, and the like.

The terms "treatment of" and "treating" pain or diarrhea include the lessening of the severity of or cessation of pain or diarrhea. In one embodiment, "treating" or "treatment of" includes inhibiting, for example decreasing, the overall frequency of episodes of pain or diarrhea.

The terms "prevention of" and "preventing" pain or diarrhea include the avoidance of the onset of pain or diarrhea.

The phrase "opioid receptor" means a δ-opioid receptor, a κ-opioid receptor, a μ-opioid receptor or an ORL-1 receptor.

The phrase "effective amount" when used in connection with a 4-Tetrazolyl-4-phenylpiperidine Compound means an amount of the 4-Tetrazolyl-4-phenylpiperidine Compound that is useful for treating or preventing pain or diarrhea in an animal or stimulating opioid-receptor function in a cell.

The phrase "effective amount" when used in connection with another therapeutic agent means an amount for providing the therapeutic effect of that therapeutic agent.

When a first group is "substituted with with one or more" second groups, each of one or more of the first group's hydrogen atoms is replaced with a second group.

In one embodiment, a first group is substituted with up to three second groups.

In another embodiment, a first group is substituted with one or two second groups.

In another embodiment, a first group is substituted with only one second group.

4.2 The 4-Tetrazolyl-4-phenylpiperidine Compounds

As stated above, the present invention encompasses 4-Tetrazolyl-4-phenylpiperidine Compounds having the formula (Ia):

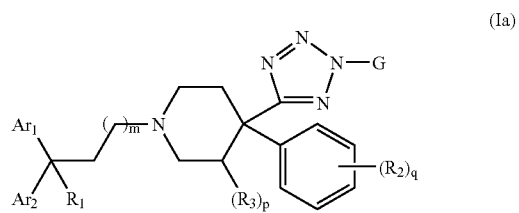

and pharmaceutically acceptable salts thereof, wherein $Ar_1$, $Ar_2$, $R_1$-$R_3$, G, m, p and q are as defined above.

In one embodiment, the 4-Tetrazolyl-4-phenylpiperidine Compounds of formula (Ia) are those wherein G is —H.

In another embodiment, the 4-Tetrazolyl-4-phenylpiperidine Compounds of formula (Ia) are those wherein G is -L-$(CH_2)_n CO_2 R_4$.

In another embodiment, the 4-Tetrazolyl-4-phenylpiperidine Compounds of formula (Ia) are those wherein G is -L-$(CH_2)_n CO_2 R_4$ and L=—C(O)—.

In another embodiment, the 4-Tetrazolyl-4-phenylpiperidine Compounds of formula (Ia) are those wherein G is -L-$(CH_2)_n CO_2 R_4$ and L=—$SO_2$— or —SO—.

In another embodiment, the 4-Tetrazolyl-4-phenylpiperidine Compounds of formula (Ia) are those wherein G is -L-$(CH_2)_n CO_2 R_4$ and $R_4$=H.

In another embodiment, the 4-Tetrazolyl-4-phenylpiperidine Compounds of formula (Ia) are those wherein G is -L-$(CH_2)_n CO_2 R_4$ and $R_4$=—$C_1$-$C_{10}$ alkyl.

In another embodiment, the 4-Tetrazolyl-4-phenylpiperidine Compounds of formula (Ia) are those wherein G is -L-$(CH_2)_n CO_2 R_4$ and $R_4$=—$CH_2 O(C_1$-$C_4$ alkyl).

In another embodiment, the 4-Tetrazolyl-4-phenylpiperidine Compounds of formula (Ia) are those wherein G is -L-$(CH_2)_n CO_2 R_4$ and $R_4$=—$CH_2 NH(C_1$-$C_4$ alkyl) or —$CH_2 N(C_1$-$C_4$ alkyl)$_2$.

In another embodiment, the 4-Tetrazolyl-4-phenylpiperidine Compounds of formula (Ia) are those wherein G=—$(C_1$-$C_5$ alkylene)$COOR_4$.

In another embodiment, the 4-Tetrazolyl-4-phenylpiperidine Compounds of formula (Ia) are those wherein G=—$CH_2$—$COOR_4$.

In another embodiment, the 4-Tetrazolyl-4-phenylpiperidine Compounds of formula (Ia) are those wherein G=—$(CH_2)_2$—$COOR_4$.

In another embodiment, the 4-Tetrazolyl-4-phenylpiperidine Compounds of formula (Ia) are those wherein G=—$(CH_2)_3$—$COOR_4$.

In another embodiment, the 4-Tetrazolyl-4-phenylpiperidine Compounds of formula (Ia) are those wherein G=—$(CH_2)_4$—$COOR_4$.

In another embodiment, the 4-Tetrazolyl-4-phenylpiperidine Compounds of formula (Ia) are those wherein G=—$(CH_2)_5$—$COOR_4$.

In another embodiment, the 4-Tetrazolyl-4-phenylpiperidine Compounds of formula (Ia) are those wherein G is -L-$(CH_2)_n R_5$ and $R_5$=—$NHSO_2 R_4$.

In another embodiment, the 4-Tetrazolyl-4-phenylpiperidine Compounds of formula (Ia) are those wherein G is -L-$(CH_2)_n R_5$ and $R_5$=—$C(O)NH_2$, —C(O)NHOH, —C(O)NH($C_1$-$C_4$ alkyl), or —C(O)N($C_1$-$C_4$ alkyl)$_2$.

In another embodiment, the 4-Tetrazolyl-4-phenylpiperidine Compounds of formula (Ia) are those wherein G is -L-$(CH_2)_nR_5$ and $R_5$=—$SO_2NH_2$, —$SO_2NH(C_1-C_4$ alkyl), or —$SO_2N(C_1-C_4$ alkyl$)_2$.

In another embodiment, the 4-Tetrazolyl-4-phenylpiperidine Compounds of formula (Ia) are those wherein G is -L-$(CH_2)_nR_5$ and $R_5$=—$NHSO_2H$.

In another embodiment, the 4-Tetrazolyl-4-phenylpiperidine Compounds of formula (Ia) are those wherein G is -L-$(CH_2)_nR_5$ and L=—C(O)—.

In another embodiment, the 4-Tetrazolyl-4-phenylpiperidine Compounds of formula (Ia) are those wherein G is -L-$(CH_2)_nR_5$ and L=—$SO_2$— or —SO—.

In another embodiment, the 4-Tetrazolyl-4-phenylpiperidine Compounds of formula (Ia) are those wherein G=—$(C_1$-$C_5$ alkylene$)R_5$.

In another embodiment, the 4-Tetrazolyl-4-phenylpiperidine Compounds of formula (Ia) are those wherein G=—$CH_2$—$R_5$.

In another embodiment, the 4-Tetrazolyl-4-phenylpiperidine Compounds of formula (Ia) are those wherein G=—$(CH_2)_2$—$R_5$.

In another embodiment, the 4-Tetrazolyl-4-phenylpiperidine Compounds of formula (Ia) are those wherein G=—$(CH_2)_3$—$R_5$.

In another embodiment, the 4-Tetrazolyl-4-phenylpiperidine Compounds of formula (Ia) are those wherein G=—$(CH_2)_4$—$R_5$.

In another embodiment, the 4-Tetrazolyl-4-phenylpiperidine Compounds of formula (Ia) are those wherein G=—$(CH_2)_5$—$R_5$.

In another embodiment, the 4-Tetrazolyl-4-phenylpiperidine Compounds of formula (Ia) are those wherein G=—$(C_1$-$C_5$ alkylene$)R_5$ and $R_5$=—$C(O)NH_2$, —$C(O)NHOH$, —$C(O)NH(C_1-C_4$ alkyl), or —$C(O)N(C_1-C_4$ alkyl$)_2$.

In another embodiment, the 4-Tetrazolyl-4-phenylpiperidine Compounds of formula (Ia) are those wherein G=—$CH_2$—$R_5$ and $R_5$=—$C(O)NH_2$, —$C(O)NHOH$, —$C(O)NH(C_1-C_4$ alkyl), or —$C(O)N(C_1-C_4$ alkyl$)_2$.

In another embodiment, the 4-Tetrazolyl-4-phenylpiperidine Compounds of formula (Ia) are those wherein G=—$CH_2C(O)N(CH_3)_2$.

In another embodiment, the 4-Tetrazolyl-4-phenylpiperidine Compounds of formula (Ia) are those wherein G=—$(CH_2)_2$—$R_5$ and $R_5$=—$C(O)NH_2$, —$C(O)NHOH$, —$C(O)NH(C_1-C_4$ alkyl), or —$C(O)N(C_1-C_4$ alkyl$)_2$.

In another embodiment, the 4-Tetrazolyl-4-phenylpiperidine Compounds of formula (Ia) are those wherein G=—$(CH_2)_3$—$R_5$ and $R_5$=—$C(O)NH_2$, —$C(O)NHOH$, —$C(O)NH(C_1-C_4$ alkyl), or —$C(O)N(C_1-C_4$ alkyl$)_2$.

In another embodiment, the 4-Tetrazolyl-4-phenylpiperidine Compounds of formula (Ia) are those wherein G=—$(CH_2)_4$—$R_5$ and $R_5$=—$C(O)NH_2$, —$C(O)NHOH$, —$C(O)NH(C_1-C_4$ alkyl), or —$C(O)N(C_1-C_4$ alkyl$)_2$.

In another embodiment, the 4-Tetrazolyl-4-phenylpiperidine Compounds of formula (Ia) are those wherein G=—$(CH_2)_5$—$R_5$ and $R_5$=—$C(O)NH_2$, —$C(O)NHOH$, —$C(O)NH(C_1-C_4$ alkyl), or —$C(O)N(C_1-C_4$ alkyl$)_2$.

In another embodiment, the 4-Tetrazolyl-4-phenylpiperidine Compounds of formula (Ia) are those wherein p=0.

In another embodiment, the 4-Tetrazolyl-4-phenylpiperidine Compounds of formula (Ia) are those wherein p=1.

In another embodiment, the 4-Tetrazolyl-4-phenylpiperidine Compounds of formula (Ia) are those wherein p=1 and the carbon atom to which $R_3$ is attached is in the (R)-configuration.

In another embodiment, the 4-Tetrazolyl-4-phenylpiperidine Compounds of formula (Ia) are those wherein p=1 and the carbon atom to which $R_3$ is attached is in the (S)-configuration.

In another embodiment, the 4-Tetrazolyl-4-phenylpiperidine Compounds of formula (Ia) are those wherein p=1 and $R_3$ is —$C_1$-$C_3$ alkyl.

In another embodiment, the 4-Tetrazolyl-4-phenylpiperidine Compounds of formula (Ia) are those wherein p=1 and $R_3$ is —$CH_3$.

In another embodiment, the 4-Tetrazolyl-4-phenylpiperidine Compounds of formula (Ia) are those wherein p=1, $R_3$ is —$C_1$-$C_3$ alkyl, and the carbon atom to which $R_3$ is attached is in the (R) configuration.

In another embodiment, the 4-Tetrazolyl-4-phenylpiperidine Compounds of formula (Ia) are those wherein p=1, $R_3$ is —$CH_3$, and the carbon atom to which $R_3$ is attached is in the (R) configuration.

In another embodiment, the 4-Tetrazolyl-4-phenylpiperidine Compounds of formula (Ia) are those wherein p=1, $R_3$ is —$C_1$-$C_3$ alkyl, and the carbon atom to which $R_3$ is attached is in the (S) configuration.

In another embodiment, the 4-Tetrazolyl-4-phenylpiperidine Compounds of formula (Ia) are those wherein p=1, and $R_3$ is —$CH_3$, and the carbon atom to which $R_3$ is attached is in the (S) configuration.

In another embodiment, the 4-Tetrazolyl-4-phenylpiperidine Compounds of formula (Ia) are those wherein q=0.

In another embodiment, the 4-Tetrazolyl-4-phenylpiperidine Compounds of formula (Ia) are those wherein m=0.

In another embodiment, the 4-Tetrazolyl-4-phenylpiperidine Compounds of formula (Ia) are those wherein m=1.

In another embodiment, the 4-Tetrazolyl-4-phenylpiperidine Compounds of formula (Ia) are those wherein m=0, and p=0.

In another embodiment, the 4-Tetrazolyl-4-phenylpiperidine Compounds of formula (Ia) are those wherein m=1 and p=0.

In another embodiment, the 4-Tetrazolyl-4-phenylpiperidine Compounds of formula (Ia) are those wherein m=0, and q=0.

In another embodiment, the 4-Tetrazolyl-4-phenylpiperidine Compounds of formula (Ia) are those wherein m=1 and q=0.

In another embodiment, the 4-Tetrazolyl-4-phenylpiperidine Compounds of formula (Ia) are those wherein m=0, p=0 and q=0.

In another embodiment, the 4-Tetrazolyl-4-phenylpiperidine Compounds of formula (Ia) are those wherein m=1, p=0 and q=0.

In another embodiment, the 4-Tetrazolyl-4-phenylpiperidine Compounds of formula (Ia) are those wherein $R_2$ is —Br, —Cl, —I, or —F.

In another embodiment, the 4-Tetrazolyl-4-phenylpiperidine Compounds of formula (Ia) are those wherein $R_2$ is —O($C_1$-$C_3$ alkyl).

In another embodiment, the 4-Tetrazolyl-4-phenylpiperidine Compounds of formula (Ia) are those wherein $R_2$ is —$C_1$-$C_3$ alkyl.

In another embodiment, the 4-Tetrazolyl-4-phenylpiperidine Compounds of formula (Ia) are those wherein $R_2$ is —NH($C_1$-$C_3$ alkyl) or —N($C_1$-$C_3$ alkyl$)_2$.

In another embodiment, the 4-Tetrazolyl-4-phenylpiperidine Compounds of formula (Ia) are those wherein $R_3$ is —Br, —Cl, —I, or —F.

In another embodiment, the 4-Tetrazolyl-4-phenylpiperidine Compounds of formula (Ia) are those wherein $R_3$ is —O($C_1$-$C_3$ alkyl).

In another embodiment, the 4-Tetrazolyl-4-phenylpiperidine Compounds of formula (Ia) are those wherein $R_3$ is —$C_1$-$C_3$ alkyl.

In another embodiment, the 4-Tetrazolyl-4-phenylpiperidine Compounds of formula (Ia) are those wherein $R_3$ is —NH($C_1$-$C_3$ alkyl), or —N($C_1$-$C_3$ alkyl)$_2$.

In another embodiment, the 4-Tetrazolyl-4-phenylpiperidine Compounds of formula (Ia) are those wherein $R_1$ is H.

In another embodiment, the 4-Tetrazolyl-4-phenylpiperidine Compounds of formula (Ia) are those wherein $R_1$ is —C(O)NH$_2$, —C(O)NHOH, —C(O)NH($C_1$-$C_4$ alkyl), or —C(O)N($C_1$-$C_4$ alkyl)$_2$.

In another embodiment, the 4-Tetrazolyl-4-phenylpiperidine Compounds of formula (Ia) are those wherein $R_1$ is —C(O)N(CH$_3$)$_2$.

In another embodiment, the 4-Tetrazolyl-4-phenylpiperidine Compounds of formula (Ia) are those wherein $R_1$ is —C(O)N(CH$_2$CH$_3$)$_2$.

In another embodiment, the 4-Tetrazolyl-4-phenylpiperidine Compounds of formula (Ia) are those wherein $R_1$ is —C(O)NHCH$_3$.

In another embodiment, the 4-Tetrazolyl-4-phenylpiperidine Compounds of formula (Ia) are those wherein $R_1$ is —C(O)NH(CH$_2$CH$_3$).

In another embodiment, the 4-Tetrazolyl-4-phenylpiperidine Compounds of formula (Ia) are those wherein $R_1$ is —COOR$_4$.

In another embodiment, the 4-Tetrazolyl-4-phenylpiperidine Compounds of formula (Ia) are those wherein $R_1$ is —CHO.

In another embodiment, the 4-Tetrazolyl-4-phenylpiperidine Compounds of formula (Ia) are those wherein $R_1$ is —CN.

In another embodiment, the 4-Tetrazolyl-4-phenylpiperidine Compounds of formula (Ia) are those wherein $R_1$ is —($C_1$-$C_4$ alkyl).

In another embodiment, the 4-Tetrazolyl-4-phenylpiperidine Compounds of formula (Ia) are those wherein $R_1$ is

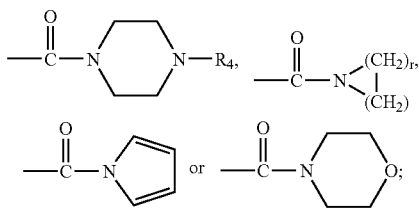

In another embodiment, the 4-Tetrazolyl-4-phenylpiperidine Compounds of formula (Ia) are those wherein $Ar_1$ is —$C_3$-$C_8$ cycloalkyl.

In another embodiment, the 4-Tetrazolyl-4-phenylpiperidine Compounds of formula (Ia) are those wherein $Ar_1$ is phenyl, naphthyl, anthryl, or phenanthryl.

In another embodiment, the 4-Tetrazolyl-4-phenylpiperidine Compounds of formula (Ia) are those wherein $Ar_1$ is -(5- to 7-membered) heteroaryl.

In another embodiment, the 4-Tetrazolyl-4-phenylpiperidine Compounds of formula (Ia) are those wherein $Ar_1$ is substituted with one or more $R_2$ groups.

In another embodiment, the 4-Tetrazolyl-4-phenylpiperidine Compounds of formula (Ia) are those wherein $Ar_2$ is phenyl, naphthyl, anthryl, or phenanthryl.

In another embodiment, the 4-Tetrazolyl-4-phenylpiperidine Compounds of formula (Ia) are those wherein $Ar_2$ is -(5- to 7-membered) heteroaryl.

In another embodiment, the 4-Tetrazolyl-4-phenylpiperidine Compounds of formula (Ia) are those wherein $Ar_2$ is substituted with one or more $R_2$ groups.

In another embodiment, the 4-Tetrazolyl-4-phenylpiperidine Compounds of formula (Ia) are those wherein $Ar_1$ and $Ar_2$ are phenyl.

In another embodiment, the 4-Tetrazolyl-4-phenylpiperidine Compounds of formula (Ia) are those wherein $Ar_1$ is cyclohexyl.

In another embodiment, the 4-Tetrazolyl-4-phenylpiperidine Compounds of formula (Ia) are those wherein $Ar_1$ is cyclohexyl and $Ar_2$ is phenyl.

In another embodiment, the 4-Tetrazolyl-4-phenylpiperidine Compounds of formula (Ia) are those wherein G=H, and p=0.

In another embodiment, the 4-Tetrazolyl-4-phenylpiperidine Compounds of formula (Ia) are those wherein G=H, and q=0.

In another embodiment, the 4-Tetrazolyl-4-phenylpiperidine Compounds of formula (Ia) are those wherein G=H, and m=0.

In another embodiment, the 4-Tetrazolyl-4-phenylpiperidine Compounds of formula (Ia) are those wherein G=H, and m=1.

In another embodiment, the 4-Tetrazolyl-4-phenylpiperidine Compounds of formula (Ia) are those wherein G=H, and $Ar_1$ and $Ar_2$ are phenyl.

In another embodiment, the 4-Tetrazolyl-4-phenylpiperidine Compounds of formula (Ia) are those wherein G=H, p=0, and q=0.

In another embodiment, the 4-Tetrazolyl-4-phenylpiperidine Compounds of formula (Ia) are those wherein G=H, p=0, and m=0.

In another embodiment, the 4-Tetrazolyl-4-phenylpiperidine Compounds of formula (Ia) are those wherein G=H, p=0, and m=1.

In another embodiment, the 4-Tetrazolyl-4-phenylpiperidine Compounds of formula (Ia) are those wherein G=H, p=0, and $Ar_1$ and $Ar_2$ are phenyl.

In another embodiment, the 4-Tetrazolyl-4-phenylpiperidine Compounds of formula (Ia) are those wherein G=H, p=0, q=0, and m=0.

In another embodiment, the 4-Tetrazolyl-4-phenylpiperidine Compounds of formula (Ia) are those wherein G=H, p=0, q=0, and m=1.

In another embodiment, the 4-Tetrazolyl-4-phenylpiperidine Compounds of formula (Ia) are those wherein G=H, p=0, q=0, and $Ar_1$ and $Ar_2$ are phenyl.

In another embodiment, the 4-Tetrazolyl-4-phenylpiperidine Compounds of formula (Ia) are those wherein G=H, p=0, q=0, m=0, and $Ar_1$ and $Ar_2$ are phenyl.

In another embodiment, the 4-Tetrazolyl-4-phenylpiperidine Compounds of formula (Ia) are those wherein G=H, p=0, q=0, m=1, and $Ar_1$ and $Ar_2$ are phenyl.

Illustrative 4-Tetrazolyl-4-phenylpiperidine Compounds of formula (Ia) have the following structure:

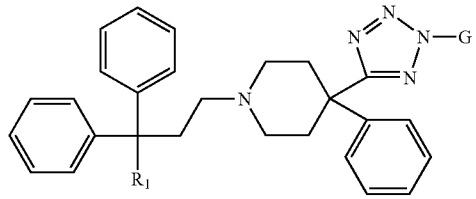

are pharmaceutically acceptable salts thereof, wherein G and R₁ are as follows:

| Compound No.: | G: | R₁: |
|---|---|---|
| AAA | —H | —H |
| AAB | —CH₂C(O)NH₂ | —H |
| AAC | —CH₂C(O)N(CH₃)₂ | —H |
| AAD | —C(O)CH₂NHSO₂CH₃ | —H |
| AAE | —(CH₂)₂C(O)NH₂ | —H |
| AAF | —(CH₂)₂C(O)N(CH₃)₂ | —H |
| AAG | —C(O)(CH₂)₂NHSO₂CH₃ | —H |
| AAH | —CH₂CO₂CH₃ | —H |
| AAI | —CH₂CO₂CH₂CH₃ | —H |
| AAJ | —(CH₂)₂CO₂CH₃ | —H |
| AAK | —(CH₂)₂CO₂CH₂CH₃ | —H |
| AAL | —(CH₂)₃CO₂CH₃ | —H |
| AAM | —(CH₂)₃CO₂CH₂CH₃ | —H |
| AAN | —(CH₂)₄CO₂CH₃ | —H |
| AAO | —(CH₂)₄CO₂CH₂CH₃ | —H |
| AAP | —CH₂SO₂NH₂ | —H |
| AAQ | —CH₂SO₂N(CH₃)₂ | —H |
| AAR | —(CH₂)₂NHSO₂H | —H |
| AAS | —(CH₂)₂NHSO₂CH₃ | —H |
| AAT | —H | —C(O)NH₂ |
| AAU | —CH₂C(O)NH₂ | —C(O)NH₂ |
| AAV | —CH₂C(O)N(CH₃)₂ | —C(O)NH₂ |
| AAW | —CH₂NHSO₂CH₃ | —C(O)NH₂ |
| AAX | —(CH₂)₂C(O)NH₂ | —C(O)NH₂ |
| AAY | —(CH₂)₂C(O)N(CH₃)₂ | —C(O)NH₂ |
| AAZ | —(CH₂)₂NHSO₂CH₃ | —C(O)NH₂ |
| ABA | —CH₂CO₂CH₃ | —C(O)NH₂ |
| ABB | —CH₂CO₂CH₂CH₃ | —C(O)NH₂ |
| ABC | —(CH₂)₂CO₂CH₃ | —C(O)NH₂ |
| ABD | —(CH₂)₂CO₂CH₂CH₃ | —C(O)NH₂ |
| ABE | —(CH₂)₃CO₂CH₃ | —C(O)NH₂ |
| ABF | —(CH₂)₃CO₂CH₂CH₃ | —C(O)NH₂ |
| ABG | —(CH₂)₄CO₂CH₃ | —C(O)NH₂ |
| ABH | —(CH₂)₄CO₂CH₂CH₃ | —C(O)NH₂ |
| ABI | —CH₂SO₂NH₂ | —C(O)NH₂ |
| ABJ | —CH₂SO₂N(CH₃)₂ | —C(O)NH₂ |
| ABK | —(CH₂)₂NHSO₂H | —C(O)NH₂ |
| ABL | —(CH₂)₂NHSO₂CH₃ | —C(O)NH₂ |
| ABM | —H | —CO₂CH₃ |
| ABN | —CH₂C(O)NH₂ | —CO₂CH₃ |
| ABO | —CH₂C(O)N(CH₃)₂ | —CO₂CH₃ |
| ABP | —C(O)CH₂NHSO₂CH₃ | —CO₂CH₃ |
| ABQ | —(CH₂)₂C(O)NH₂ | —CO₂CH₃ |
| ABR | —(CH₂)₂C(O)N(CH₃)₂ | —CO₂CH₃ |
| ABS | —C(O)(CH₂)₂NHSO₂CH₃ | —CO₂CH₃ |
| ABT | —CH₂CO₂CH₃ | —CO₂CH₃ |
| ABU | —CH₂CO₂CH₂CH₃ | —CO₂CH₃ |
| ABV | —(CH₂)₂CO₂CH₃ | —CO₂CH₃ |
| ABW | —(CH₂)₂CO₂CH₂CH₃ | —CO₂CH₃ |
| ABX | —(CH₂)₃CO₂CH₃ | —CO₂CH₃ |
| ABY | —(CH₂)₃CO₂CH₂CH₃ | —CO₂CH₃ |
| ABZ | —(CH₂)₄CO₂CH₃ | —CO₂CH₃ |
| ACA | —(CH₂)₄CO₂CH₂CH₃ | —CO₂CH₃ |
| ACB | —CH₂SO₂NH₂ | —CO₂CH₃ |
| ACC | —CH₂SO₂N(CH₃)₂ | —CO₂CH₃ |
| ACD | —(CH₂)₂NHSO₂H | —CO₂CH₃ |
| ACE | —(CH₂)₂NHSO₂CH₃ | —CO₂CH₃ |
| ACF | —H | —CHO |
| ACG | —CH₂C(O)NH₂ | —CHO |
| ACH | —CH₂C(O)N(CH₃)₂ | —CHO |
| ACI | —C(O)CH₂NHSO₂CH₃ | —CHO |
| ACJ | —(CH₂)₂C(O)NH₂ | —CHO |
| ACK | —(CH₂)₂C(O)N(CH₃)₂ | —CHO |
| ACL | —C(O)(CH₂)₂NHSO₂CH₃ | —CHO |
| ACM | —CH₂CO₂CH₃ | —CHO |
| ACN | —CH₂CO₂CH₂CH₃ | —CHO |
| ACO | —(CH₂)₂CO₂CH₃ | —CHO |
| ACP | —(CH₂)₂CO₂CH₂CH₃ | —CHO |
| ACQ | —(CH₂)₃CO₂CH₃ | —CHO |
| ACR | —(CH₂)₃CO₂CH₂CH₃ | —CHO |
| ACS | —(CH₂)₄CO₂CH₃ | —CHO |
| ACT | —(CH₂)₄CO₂CH₂CH₃ | —CHO |
| ACU | —CH₂SO₂NH₂ | —CHO |
| ACV | —CH₂SO₂N(CH₃)₂ | —CHO |
| ACW | —(CH₂)₂NHSO₂H | —CHO |
| ACX | —(CH₂)₂NHSO₂CH₃ | —CHO |
| ACY | —H | —CN |
| ACZ | —CH₂C(O)NH₂ | —CN |
| ADA | —CH₂C(O)N(CH₃)₂ | —CN |
| ADB | —C(O)CH₂NHSO₂CH₃ | —CN |
| ADC | —(CH₂)₂C(O)NH₂ | —CN |
| ADD | —(CH₂)₂C(O)N(CH₃)₂ | —CN |
| ADE | —C(O)(CH₂)₂NHSO₂CH₃ | —CN |
| ADF | —CH₂CO₂CH₃ | —CN |
| ADG | —CH₂CO₂CH₂CH₃ | —CN |
| ADH | —(CH₂)₂CO₂CH₃ | —CN |
| ADI | —(CH₂)₂CO₂CH₂CH₃ | —CN |
| ADJ | —(CH₂)₃CO₂CH₃ | —CN |
| ADK | —(CH₂)₃CO₂CH₂CH₃ | —CN |
| ADL | —(CH₂)₄CO₂CH₃ | —CN |
| ADM | —(CH₂)₄CO₂CH₂CH₃ | —CN |
| AND | —CH₂SO₂NH₂ | —CN |
| ADO | —CH₂SO₂N(CH₃)₂ | —CN |
| ADP | —(CH₂)₂NHSO₂H | —CN |
| ADQ | —(CH₂)₂NHSO₂CH₃ | —CN |
| ADR | —H | —CH₃ |
| ADS | —CH₂C(O)NH₂ | —CH₃ |
| ADT | —CH₂C(O)N(CH₃)₂ | —CH₃ |
| ADU | —C(O)CH₂NHSO₂CH₃ | —CH₃ |
| ADV | —(CH₂)₂C(O)NH₂ | —CH₃ |
| ADW | —(CH₂)₂C(O)N(CH₃)₂ | —CH₃ |
| ADX | —C(O)(CH₂)₂NHSO₂CH₃ | —CH₃ |
| ADY | —CH₂CO₂CH₃ | —CH₃ |
| ADZ | —CH₂CO₂CH₂CH₃ | —CH₃ |
| AEA | —(CH₂)₂CO₂CH₃ | —CH₃ |
| AEB | —(CH₂)₂CO₂CH₂CH₃ | —CH₃ |
| AEC | —(CH₂)₃CO₂CH₃ | —CH₃ |
| AED | —(CH₂)₃CO₂CH₂CH₃ | —CH₃ |
| AEE | —(CH₂)₄CO₂CH₃ | —CH₃ |
| AEF | —(CH₂)₄CO₂CH₂CH₃ | —CH₃ |
| AEG | —CH₂SO₂NH₂ | —CH₃ |
| AEH | —CH₂SO₂N(CH₃)₂ | —CH₃ |
| AEI | —(CH₂)₂NHSO₂H | —CH₃ |
| AEJ | —(CH₂)₂NHSO₂CH₃ | —CH₃ |
| AEK | —H | —C(O)NH(CH₃) |
| AEL | —CH₂C(O)NH₂ | —C(O)NH(CH₃) |
| AEM | —CH₂C(O)N(CH₃)₂ | —C(O)NH(CH₃) |
| AEN | —C(O)CH₂NHSO₂CH₃ | —C(O)NH(CH₃) |
| AEO | —(CH₂)₂C(O)NH₂ | —C(O)NH(CH₃) |
| AEP | —(CH₂)₂C(O)N(CH₃)₂ | —C(O)NH(CH₃) |
| AEQ | —C(O)(CH₂)₂NHSO₂CH₃ | —C(O)NH(CH₃) |
| AER | —CH₂CO₂CH₃ | —C(O)NH(CH₃) |
| AES | —CH₂CO₂CH₂CH₃ | —C(O)NH(CH₃) |
| AET | —(CH₂)₂CO₂CH₃ | —C(O)NH(CH₃) |
| AEU | —(CH₂)₂CO₂CH₂CH₃ | —C(O)NH(CH₃) |
| AEV | —(CH₂)₃CO₂CH₃ | —C(O)NH(CH₃) |
| AEW | —(CH₂)₃CO₂CH₂CH₃ | —C(O)NH(CH₃) |
| AEX | —(CH₂)₄CO₂CH₃ | —C(O)NH(CH₃) |
| AEY | —(CH₂)₄CO₂CH₂CH₃ | —C(O)NH(CH₃) |
| AEZ | —CH₂SO₂NH₂ | —C(O)NH(CH₃) |
| AFA | —CH₂SO₂N(CH₃)₂ | —C(O)NH(CH₃) |
| AFB | —(CH₂)₂NHSO₂H | —C(O)NH(CH₃) |
| AFC | —(CH₂)₂NHSO₂CH₃ | —C(O)NH(CH₃) |
| AFD | —H | —C(O)N(CH₃)₂ |

| Compound No.: | G: | R₁: |
|---|---|---|
| AFE | —CH₂C(O)NH₂ | —C(O)N(CH₃)₂ |
| AFF | —CH₂C(O)N(CH₃)₂ | —C(O)N(CH₃)₂ |
| AFG | —C(O)CH₂NHSO₂CH₃ | —C(O)N(CH₃)₂ |
| AFH | —(CH₂)₂C(O)NH₂ | —C(O)N(CH₃)₂ |
| AFI | —(CH₂)₂C(O)N(CH₃)₂ | —C(O)N(CH₃)₂ |
| AFJ | —C(O)(CH₂)₂NHSO₂CH₃ | —C(O)N(CH₃)₂ |
| AFK | —CH₂CO₂CH₃ | —C(O)N(CH₃)₂ |
| AFL | —CH₂CO₂CH₂CH₃ | —C(O)N(CH₃)₂ |
| AFM | —(CH₂)₂CO₂CH₃ | —C(O)N(CH₃)₂ |
| AFN | —(CH₂)₂CO₂CH₂CH₃ | —C(O)N(CH₃)₂ |
| AFO | —(CH₂)₃CO₂CH₃ | —C(O)N(CH₃)₂ |
| AFP | —(CH₂)₃CO₂CH₂CH₃ | —C(O)N(CH₃)₂ |
| AFQ | —(CH₂)₄CO₂CH₃ | —C(O)N(CH₃)₂ |
| AFR | —(CH₂)₄CO₂CH₂CH₃ | —C(O)N(CH₃)₂ |
| AFS | —CH₂SO₂NH₂ | —C(O)N(CH₃)₂ |
| AFT | —CH₂SO₂N(CH₃)₂ | —C(O)N(CH₃)₂ |
| AFU | —(CH₂)₂NHSO₂H | —C(O)N(CH₃)₂ |
| AFV | —(CH₂)₂NHSO₂CH₃ | —C(O)N(CH₃)₂ |
| AFW | —H | 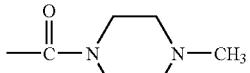 |
| AFX | —CH₂C(O)NH₂ | 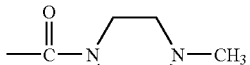 |
| AFY | —CH₂C(O)N(CH₃)₂ | 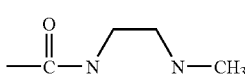 |
| AFZ | —C(O)CH₂NHSO₂CH₃ | 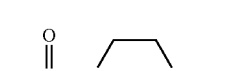 |
| AGA | —(CH₂)₂C(O)NH₂ | 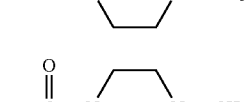 |
| AGB | —(CH₂)₂C(O)N(CH₃)₂ | 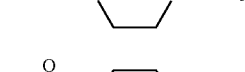 |
| AGC | —C(O)(CH₂)₂NHSO₂CH₃ | 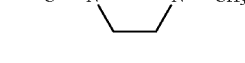 |
| AGD | —CH₂CO₂CH₃ | 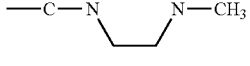 |
| AGE | —CH₂CO₂CH₂CH₃ | 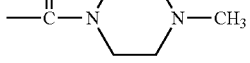 |
| AGF | —(CH₂)₂CO₂CH₃ |  |
| AGG | —(CH₂)₂CO₂CH₂CH₃ | 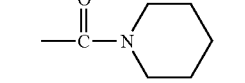 |
| AGH | —(CH₂)₃CO₂CH₃ | 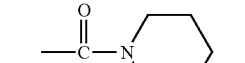 |
| AGI | —(CH₂)₃CO₂CH₂CH₃ | 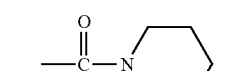 |
| AGJ | —(CH₂)₄CO₂CH₃ | 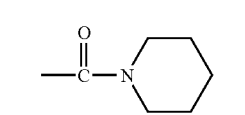 |
| AGK | —(CH₂)₄CO₂CH₂CH₃ | 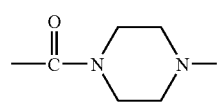 |
| AGL | —CH₂SO₂NH₂ | 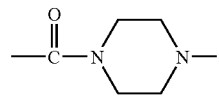 |
| AGM | —CH₂SO₂N(CH₃)₂ | 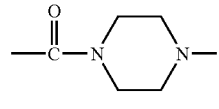 |
| AGN | —(CH₂)₂NHSO₂H | 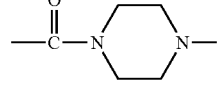 |
| AGO | —(CH₂)₂NHSO₂CH₃ | 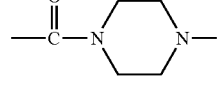 |
| AGP | —H | 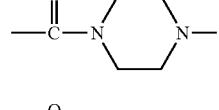 |
| AGQ | —CH₂C(O)NH₂ | 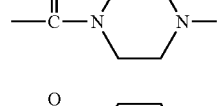 |
| AGR | —CH₂C(O)N(CH₃)₂ | 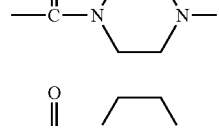 |
| AGS | —C(O)CH₂NHSO₂CH₃ | 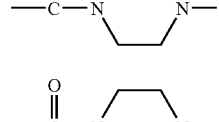 |
| AGT | —(CH₂)₂C(O)NH₂ | 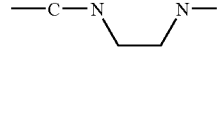 |

-continued

| Compound No.: | G: | R₁: |
|---|---|---|
| AGU | —(CH₂)₂C(O)N(CH₃)₂ | 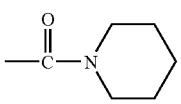 |
| AGV | —C(O)(CH₂)₂NHSO₂CH₃ | 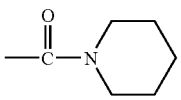 |
| AGW | —CH₂CO₂CH₃ | 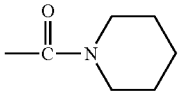 |
| AGX | —CH₂CO₂CH₂CH₃ | 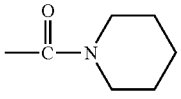 |
| AGY | —(CH₂)₂CO₂CH₃ | 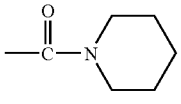 |
| AGZ | —(CH₂)₂CO₂CH₂CH₃ | 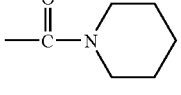 |
| AHA | —(CH₂)₃CO₂CH₃ | 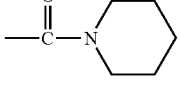 |
| AHB | —(CH₂)₃CO₂CH₂CH₃ | 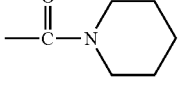 |
| AHC | —(CH₂)₄CO₂CH₃ | 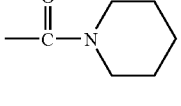 |
| AHD | —(CH₂)₄CO₂CH₂CH₃ | 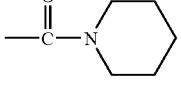 |
| AHE | —CH₂SO₂NH₂ | 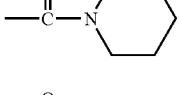 |
| AHF | —CH₂SO₂N(CH₃)₂ | 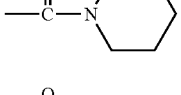 |
| AHG | —(CH₂)₂NHSO₂H | 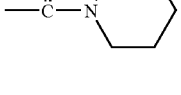 |

-continued

| Compound No.: | G: | R₁: |
|---|---|---|
| AHH | —(CH₂)₂NHSO₂CH₃ | 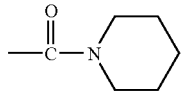 |
| AHI | —H | 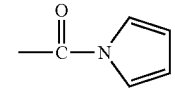 |
| AHJ | —CH₂C(O)NH₂ | 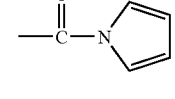 |
| AHK | —CH₂C(O)N(CH₃)₂ | 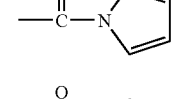 |
| AHL | —C(O)CH₂NHSO₂CH₃ | 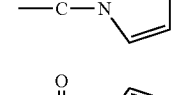 |
| ARM | —(CH₂)₂C(O)NH₂ | 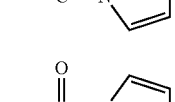 |
| ARN | —(CH₂)₂C(O)N(CH₃)₂ | 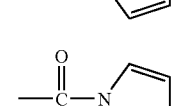 |
| AHO | —C(O)(CH₂)₂NHSO₂CH₃ | 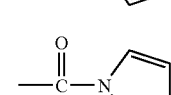 |
| AHP | —CH₂CO₂CH₃ | 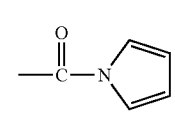 |
| AHQ | —CH₂CO₂CH₂CH₃ | 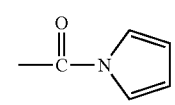 |
| AHR | —(CH₂)₂CO₂CH₃ | 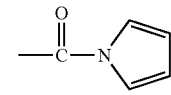 |
| AHS | —(CH₂)₂CO₂CH₂CH₃ | 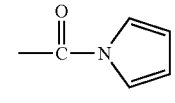 |
| AHT | —(CH₂)₃CO₂CH₃ | 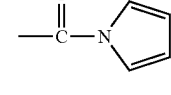 |
| AHU | —(CH₂)₃CO₂CH₂CH₃ |  |

-continued

| Compound No.: | G: | R₁: |
|---|---|---|
| AHV | —(CH₂)₄CO₂CH₃ | 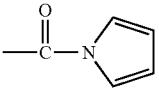 |
| AHW | —(CH₂)₄CO₂CH₂CH₃ | 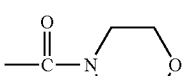 |
| AHX | —CH₂SO₂NH₂ | 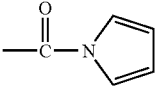 |
| AHY | —CH₂SO₂N(CH₃)₂ | 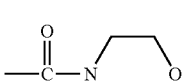 |
| AHZ | —(CH₂)₂NHSO₂H | 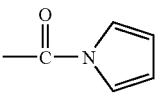 |
| AIA | —(CH₂)₂NHSO₂CH₃ | 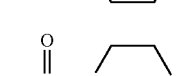 |
| AIB | —H | 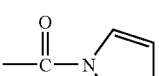 |
| AIC | —CH₂C(O)NH₂ | 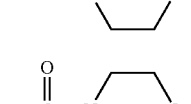 |
| AID | —CH₂C(O)N(CH₃)₂ | 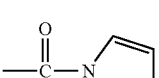 |
| AIE | —C(O)CH₂NHSO₂CH₃ | 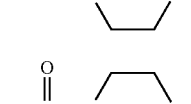 |
| AIF | —(CH₂)₂C(O)NH₂ | 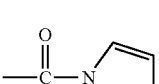 |
| AIG | —(CH₂)₂C(O)N(CH₃)₂ | 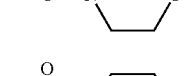 |
| AIH | —C(O)(CH₂)₂NHSO₂CH₃ | 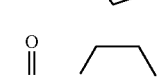 |
| AII | —CH₂CO₂CH₃ | 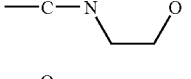 |

-continued

| Compound No.: | G: | R₁: |
|---|---|---|
| AIJ | —CH₂CO₂CH₂CH₃ | 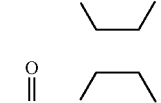 |
| AIK | —(CH₂)₂CO₂CH₃ | 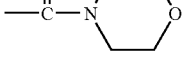 |
| AIL | —(CH₂)₂CO₂CH₂CH₃ | 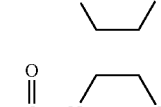 |
| AIM | —(CH₂)₃CO₂CH₃ | 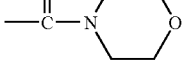 |
| AIN | —(CH₂)₃CO₂CH₂CH₃ | 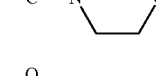 |
| AIO | —(CH₂)₄CO₂CH₃ | 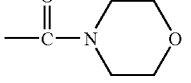 |
| AIP | —(CH₂)₄CO₂CH₂CH₃ | 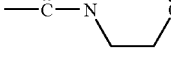 |
| AIQ | —CH₂SO₂NH₂ | 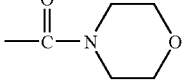 |
| AIR | —CH₂SO₂N(CH₃)₂ | 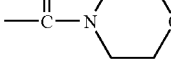 |
| AIS | —(CH₂)₂NHSO₂H | 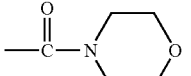 |
| AIT | —(CH₂)₂NHSO₂CH₃ | 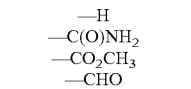 |
| AIU | —(CH₂)₃NHSO₂H | —H |
| AIV | —(CH₂)₃NHSO₂H | —C(O)NH₂ |
| AIW | —(CH₂)₃NHSO₂H | —CO₂CH₃ |
| AIX | —(CH₂)₃NHSO₂H | —CHO |
| AIY | —(CH₂)₃NHSO₂H | —CN |
| AIZ | —(CH₂)₃NHSO₂H | —CH₃ |
| AJA | —(CH₂)₃NHSO₂H | —C(O)NHCH₃ |
| AJB | —(CH₂)₃NHSO₂H | —C(O)N(CH₃)₂ |
| AJC | —(CH₂)₃NHSO₂H | 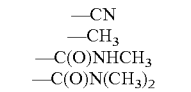 |

-continued

| Compound No.: | G: | R₁: |
|---|---|---|
| AJD | —(CH₂)₃NHSO₂H | —C(O)—N(piperidinyl) |
| AJE | —(CH₂)₃NHSO₂H | —C(O)—N(pyrrolyl) |
| AJF | —(CH₂)₃NHSO₂H | —C(O)—N(morpholinyl) |

The present invention further encompasses compounds having the formula (Ib)

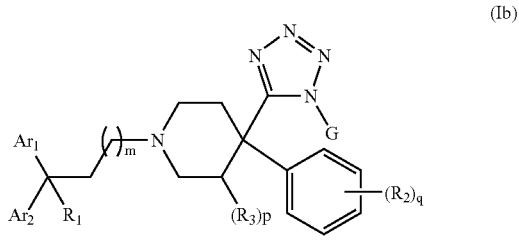

(Ib)

and pharmaceutically acceptable salts thereof, wherein $Ar_1$, $Ar_2$, $R_1$-$R_3$, G, m, p and q are as defined above.

In one embodiment, the 4-Tetrazolyl-4-phenylpiperidine Compounds of formula (Ib) are those wherein G is H.

In one embodiment, the 4-Tetrazolyl-4-phenylpiperidine Compounds of formula (Ib) are those wherein G=-L(CH₂)ₙC(O)OR₄.

In one embodiment, the 4-Tetrazolyl-4-phenylpiperidine Compounds of formula (Ib) are those wherein G=-L(CH₂)ₙC(O)OR₄ and L=—C(O)—.

In one embodiment, the 4-Tetrazolyl-4-phenylpiperidine Compounds of formula (Ib) are those wherein G=-L(CH₂)ₙC(O)OR₄ and L=—SO₂— or —SO—.

In one embodiment, the 4-Tetrazolyl-4-phenylpiperidine Compounds of formula (Ib) are those wherein G=-L(CH₂)ₙC(O)OR₄ and R₄=H.

In one embodiment, the 4-Tetrazolyl-4-phenylpiperidine Compounds of formula (Ib) are those wherein G=-L(CH₂)ₙC(O)OR₄ and R₄=—C₁-C₁₀ alkyl.

In one embodiment, the 4-Tetrazolyl-4-phenylpiperidine Compounds of formula (Ib) are those wherein G=-L(CH₂)ₙC(O)OR₄ and R₄=—CH₂O(C₁-C₄ alkyl).

In one embodiment, the 4-Tetrazolyl-4-phenylpiperidine Compounds of formula (Ib) are those wherein G=-L(CH₂)ₙC(O)OR₄ and R₄=—CH₂NH(C₁-C₄ alkyl) or —CH₂N(C₁-C₄ alkyl)₂.

In another embodiment, the 4-Tetrazolyl-4-phenylpiperidine Compounds of formula (Ib) are those wherein G=—(C₁-C₅ alkylene)R₅.

In another embodiment, the 4-Tetrazolyl-4-phenylpiperidine Compounds of formula (Ib) are those wherein G=—CH₂—R₅.

In another embodiment, the 4-Tetrazolyl-4-phenylpiperidine Compounds of formula (Ib) are those wherein G=—(CH₂)₂—R₅.

In another embodiment, the 4-Tetrazolyl-4-phenylpiperidine Compounds of formula (Ib) are those wherein G=—(CH₂)₃—R₅.

In another embodiment, the 4-Tetrazolyl-4-phenylpiperidine Compounds of formula (Ib) are those wherein G=—(CH₂)₄—R₅.

In another embodiment, the 4-Tetrazolyl-4-phenylpiperidine Compounds of formula (Ib) are those wherein G=—(CH₂)₅—R₅.

In one embodiment, the 4-Tetrazolyl-4-phenylpiperidine Compounds of formula (Ib) are those wherein G=—(C₁-C₅ alkylene)COOR₄.

In one embodiment, the 4-Tetrazolyl-4-phenylpiperidine Compounds of formula (Ib) are those wherein G=—CH₂—COOR₄.

In one embodiment, the 4-Tetrazolyl-4-phenylpiperidine Compounds of formula (Ib) are those wherein G=—(CH₂)₂—COOR₄.

In one embodiment, the 4-Tetrazolyl-4-phenylpiperidine Compounds of formula (Ib) are those wherein G=—(CH₂)₃—COOR₄.

In one embodiment, the 4-Tetrazolyl-4-phenylpiperidine Compounds of formula (Ib) are those wherein G=—(CH₂)₄—COOR₄.

In one embodiment, the 4-Tetrazolyl-4-phenylpiperidine Compounds of formula (Ib) are those wherein G=—(CH₂)₅—COOR₄.

In one embodiment, the 4-Tetrazolyl-4-phenylpiperidine Compounds of formula (Ib) are those wherein G is -L-(CH₂)ₙR₅ and R₅=—NHSO₂R₄.

In one embodiment, the 4-Tetrazolyl-4-phenylpiperidine Compounds of formula (Ib) are those wherein G is -L-(CH₂)ₙR₅ and R₅=—C(O)NH₂, —C(O)NHOH, —C(O)NH(C₁-C₄ alkyl), or —C(O)N(C₁-C₄ alkyl)₂.

In one embodiment, the 4-Tetrazolyl-4-phenylpiperidine Compounds of formula (Ib) are those wherein G is -L-(CH₂)ₙR₅ and R₅=—SO₂NH₂, —SO₂NH(C₁-C₄ alkyl), or —SO₂N(C₁-C₄ alkyl)₂.

In one embodiment, the 4-Tetrazolyl-4-phenylpiperidine Compounds of formula (Ib) are those wherein G is -L-(CH₂)ₙR₅ and R₅=—NHSO₂H.

In one embodiment, the 4-Tetrazolyl-4-phenylpiperidine Compounds of formula (Ib) are those wherein G is -L-(CH₂)ₙR₅ and L=—C(O)—.

In one embodiment, the 4-Tetrazolyl-4-phenylpiperidine Compounds of formula (Ib) are those wherein G is -L-(CH₂)ₙR₅ and L=—SO₂— or —SO—.

In one embodiment, the 4-Tetrazolyl-4-phenylpiperidine Compounds of formula (Ib) are those wherein p=0.

In another embodiment, the 4-Tetrazolyl-4-phenylpiperidine Compounds of formula (Ib) are those wherein p=1.

In another embodiment, the 4-Tetrazolyl-4-phenylpiperidine Compounds of formula (Ib) are those wherein p=1 and the carbon atom to which R₃ is attached is in the (R)-configuration.

In another embodiment, the 4-Tetrazolyl-4-phenylpiperidine Compounds of formula (Ib) are those wherein p=1 and the carbon atom to which R₃ is attached is in the (S)-configuration.

In another embodiment, the 4-Tetrazolyl-4-phenylpiperidine Compounds of formula (Ib) are those wherein p=1 and R₃ is —C₁-C₃ alkyl.

In another embodiment, the 4-Tetrazolyl-4-phenylpiperidine Compounds of formula (Ib) are those wherein p=1 and $R_3$ is —$CH_3$.

In another embodiment, the 4-Tetrazolyl-4-phenylpiperidine Compounds of formula (Ib) are those wherein p=1, $R_3$ is —$C_1$-$C_3$ alkyl, and the carbon atom to which $R_3$ is attached is in the (R) configuration.

In another embodiment, the 4-Tetrazolyl-4-phenylpiperidine Compounds of formula (Ib) are those wherein p=1, $R_3$ is —$CH_3$, and the carbon atom to which $R_3$ is attached is in the (R) configuration.

In another embodiment, the 4-Tetrazolyl-4-phenylpiperidine Compounds of formula (Ib) are those wherein p=1, $R_3$ is —$C_1$-$C_3$ alkyl, and the carbon atom to which $R_3$ is attached is in the (S) configuration.

In another embodiment, the 4-Tetrazolyl-4-phenylpiperidine Compounds of formula (Ib) are those wherein p=1, $R_3$ is —$CH_3$, and the carbon atom to which $R_3$ is attached is in the (S) configuration.

In one embodiment, the 4-Tetrazolyl-4-phenylpiperidine Compounds of formula (Ib) are those wherein q=0.

In one embodiment, the 4-Tetrazolyl-4-phenylpiperidine Compounds of formula (Ib) are those wherein m=0.

In one embodiment, the 4-Tetrazolyl-4-phenylpiperidine Compounds of formula (Ib) are those wherein m=1.

In one embodiment, the 4-Tetrazolyl-4-phenylpiperidine Compounds of formula (Ib) are those wherein m=0, and p=0.

In one embodiment, the 4-Tetrazolyl-4-phenylpiperidine Compounds of formula (Ib) are those wherein m=1 and p=0.

In one embodiment, the 4-Tetrazolyl-4-phenylpiperidine Compounds of formula (Ib) are those wherein m=0, and q=0.

In one embodiment, the 4-Tetrazolyl-4-phenylpiperidine Compounds of formula (Ib) are those wherein m=1 and q=0.

In one embodiment, the 4-Tetrazolyl-4-phenylpiperidine Compounds of formula (Ib) are those wherein m=0, p=0 and q=0.

In one embodiment, the 4-Tetrazolyl-4-phenylpiperidine Compounds of formula (Ib) are those wherein m=1, p=0 and q=0.

In one embodiment, the 4-Tetrazolyl-4-phenylpiperidine Compounds of formula (Ib) are those wherein $R_2$ is —Br, —Cl, —I, or —F.

In one embodiment, the 4-Tetrazolyl-4-phenylpiperidine Compounds of formula (Ib) are those wherein $R_2$ is —O($C_1$-$C_3$ alkyl).

In one embodiment, the 4-Tetrazolyl-4-phenylpiperidine Compounds of formula (Ib) are those wherein $R_2$ is —$C_1$-$C_3$ alkyl.

In one embodiment, the 4-Tetrazolyl-4-phenylpiperidine Compounds of formula (Ib) are those wherein $R_2$ is —NH($C_1$-$C_3$ alkyl) or —N($C_1$-$C_3$ alkyl)$_2$.

In one embodiment, the 4-Tetrazolyl-4-phenylpiperidine Compounds of formula (Ib) are those wherein $R_3$ is —Br, —Cl, —I, or —F.

In one embodiment, the 4-Tetrazolyl-4-phenylpiperidine Compounds of (Ib) are those wherein $R_3$ is —O($C_1$-$C_3$ alkyl).

In one embodiment, the 4-Tetrazolyl-4-phenylpiperidine Compounds of formula (Ib) are those wherein $R_3$ is —$C_1$-$C_3$ alkyl.

In one embodiment, the 4-Tetrazolyl-4-phenylpiperidine Compounds of formula (Ib) are those wherein $R_3$ is —NH($C_1$-$C_3$ alkyl) or —N($C_1$-$C_3$ alkyl)$_2$.

In one embodiment, the 4-Tetrazolyl-4-phenylpiperidine Compounds of formula (Ib) are those wherein $R_1$ is H.

In one embodiment, the 4-Tetrazolyl-4-phenylpiperidine Compounds of formula (Ib) are those wherein $R_1$ is —C(O)$NH_2$, —C(O)NHOH, —C(O)NH($C_1$-$C_4$ alkyl), or —C(O)N($C_1$-$C_4$ alkyl)$_2$.

In one embodiment, the 4-Tetrazolyl-4-phenylpiperidine Compounds of formula (Ib) are those wherein $R_1$ is —C(O)N($CH_3$)$_2$.

In one embodiment, the 4-Tetrazolyl-4-phenylpiperidine Compounds of formula (Ib) are those wherein $R_1$ is —C(O)N($CH_2CH_3$)$_2$.

In one embodiment, the 4-Tetrazolyl-4-phenylpiperidine Compounds of formula (Ib) are those wherein $R_1$ is —C(O)$NHCH_3$.

In one embodiment, the 4-Tetrazolyl-4-phenylpiperidine Compounds of formula (Ib) are those wherein $R_1$ is —C(O)NH($CH_2CH_3$).

In one embodiment, the 4-Tetrazolyl-4-phenylpiperidine Compounds of formula (Ib) are those wherein $R_1$ is —COOR$_4$.

In one embodiment, the 4-Tetrazolyl-4-phenylpiperidine Compounds of formula (Ib) are those wherein $R_1$ is —CHO.

In one embodiment, the 4-Tetrazolyl-4-phenylpiperidine Compounds of formula (Ib) are those wherein $R_1$ is —CN.

In one embodiment, the 4-Tetrazolyl-4-phenylpiperidine Compounds of formula (Ib) are those wherein $R_1$ is —($C_1$-$C_4$ alkyl).

In one embodiment, the 4-Tetrazolyl-4-phenylpiperidine Compounds of formula (Ib) are those wherein $R_1$ is

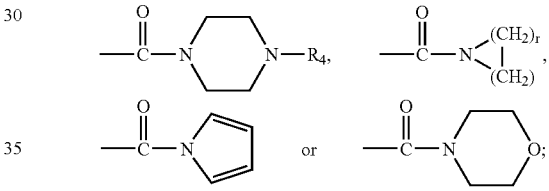

In one embodiment, the 4-Tetrazolyl-4-phenylpiperidine Compounds of formula (Ib) are those wherein $Ar_1$ is —$C_3$-$C_8$ cycloalkyl.

In one embodiment, the 4-Tetrazolyl-4-phenylpiperidine Compounds of formula (Ib) are those wherein $Ar_1$ is phenyl, naphthyl, anthryl, or phenanthryl.

In one embodiment, the 4-Tetrazolyl-4-phenylpiperidine Compounds of formula (Ib) are those wherein $Ar_1$ is -(5- to 7-membered) heteroaryl.

In one embodiment, the 4-Tetrazolyl-4-phenylpiperidine Compounds of formula (Ib) are those wherein $Ar_1$ is substituted with one or more $R_2$ groups.

In one embodiment, the 4-Tetrazolyl-4-phenylpiperidine Compounds of formula (Ib) are those wherein $Ar_2$ is phenyl, naphthyl, anthryl, or phenanthryl.

In one embodiment, the 4-Tetrazolyl-4-phenylpiperidine Compounds of formula (Ib) are those wherein $Ar_2$ is -(5- to 7-membered) heteroaryl.

In one embodiment, the 4-Tetrazolyl-4-phenylpiperidine Compounds of formula (Ib) are those wherein $Ar_2$ is substituted with one or more $R_2$ groups.

In one embodiment, the 4-Tetrazolyl-4-phenylpiperidine Compounds of formula (Ib) are those wherein $Ar_1$ and $Ar_2$ are phenyl.

In one embodiment, the 4-Tetrazolyl-4-phenylpiperidine Compounds of formula (Ib) are those wherein $Ar_1$ is cyclohexyl.

In one embodiment, the 4-Tetrazolyl-4-phenylpiperidine Compounds of formula (Ib) are those wherein $Ar_1$ is cyclohexyl and $Ar_2$ is phenyl.

In one embodiment, the 4-Tetrazolyl-4-phenylpiperidine Compounds of formula (Ib) are those wherein G=H, and p=0.

In one embodiment, the 4-Tetrazolyl-4-phenylpiperidine Compounds of formula (Ib) are those wherein G=H, and q=0.

In one embodiment, the 4-Tetrazolyl-4-phenylpiperidine Compounds of formula (Ib) are those wherein G=H, and m=0.

In one embodiment, the 4-Tetrazolyl-4-phenylpiperidine Compounds of formula (Ib) are those wherein G=H, and m=1.

In one embodiment, the 4-Tetrazolyl-4-phenylpiperidine Compounds of formula (Ib) are those wherein G=H, and $Ar_1$ and $Ar_2$ are phenyl.

In one embodiment, the 4-Tetrazolyl-4-phenylpiperidine Compounds of formula (Ib) are those wherein G=H, p=0, and q=0.

In one embodiment, the 4-Tetrazolyl-4-phenylpiperidine Compounds of formula (Ib) are those wherein G=H, p=0, and m=0.

In one embodiment, the 4-Tetrazolyl-4-phenylpiperidine Compounds of formula (Ib) are those wherein G=H, p=0, and m=1.

In one embodiment, the 4-Tetrazolyl-4-phenylpiperidine Compounds of formula (Ib) are those wherein G=H, p=0, and $Ar_1$ and $Ar_2$ are phenyl.

In one embodiment, the 4-Tetrazolyl-4-phenylpiperidine Compounds of formula (Ib) are those wherein G=H, p=0, q=0, and m=0.

In one embodiment, the 4-Tetrazolyl-4-phenylpiperidine Compounds of formula (Ib) are those wherein G=H, p=0, q=0, and m=1.

In one embodiment, the 4-Tetrazolyl-4-phenylpiperidine Compounds of formula (Ib) are those wherein G=H, p=0, q=0, and $Ar_1$ and $Ar_2$ are phenyl.

In one embodiment, the 4-Tetrazolyl-4-phenylpiperidine Compounds of formula (Ib) are those wherein G=H, p=0, q=0, m=0, and $Ar_1$ and $Ar_2$ are phenyl.

In one embodiment, the 4-Tetrazolyl-4-phenylpiperidine Compounds of formula (Ib) are those wherein G=H, p=0, q=0, m=1, and $Ar_1$ and $Ar_2$ are phenyl.

Illustrative 4-Tetrazolyl-4-phenylpiperidine Compounds of formula (Ib) have the following structure:

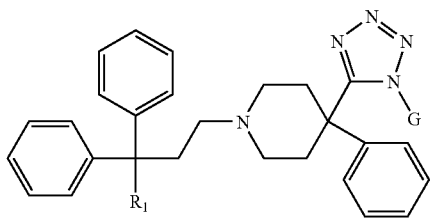

and pharmaceutically acceptable salts thereof, wherein G and $R_1$ are as follows:

| Compound No.: | G: | $R_1$: |
|---|---|---|
| BAA | —H | —H |
| BAB | —$CH_2C(O)NH_2$ | —H |
| BAC | —$CH_2C(O)N(CH_3)_2$ | —H |
| BAD | —$C(O)CH_2NHSO_2CH_3$ | —H |
| BAE | —$(CH_2)_2C(O)NH_2$ | —H |
| BAF | —$(CH_2)_2C(O)N(CH_3)_2$ | —H |
| BAG | —$C(O)(CH_2)_2NHSO_2CH_3$ | —H |
| BAH | —$CH_2CO_2CH_3$ | —H |

-continued

| Compound No.: | G: | $R_1$: |
|---|---|---|
| BAI | —$CH_2CO_2CH_2CH_3$ | —H |
| BAJ | —$(CH_2)_2CO_2CH_3$ | —H |
| BAK | —$(CH_2)_2CO_2CH_2CH_3$ | —H |
| BAL | —$(CH_2)_3CO_2CH_3$ | —H |
| BAM | —$(CH_2)_3CO_2CH_2CH_3$ | —H |
| BAN | —$(CH_2)_4CO_2CH_3$ | —H |
| BAO | —$(CH_2)_4CO_2CH_2CH_3$ | —H |
| BAP | —$CH_2SO_2NH_2$ | —H |
| BAQ | —$CH_2SO_2N(CH_3)_2$ | —H |
| BAR | —$(CH_2)_2NHSO_2H$ | —H |
| BAS | —$(CH_2)_2NHSO_2CH_3$ | —H |
| BAT | —H | —$C(O)NH_2$ |
| BAU | —$CH_2C(O)NH_2$ | —$C(O)NH_2$ |
| BAV | —$CH_2C(O)N(CH_3)_2$ | —$C(O)NH_2$ |
| BAW | —$CH_2NHSO_2CH_3$ | —$C(O)NH_2$ |
| BAX | —$(CH_2)_2C(O)NH_2$ | —$C(O)NH_2$ |
| BAY | —$(CH_2)_2C(O)N(CH_3)_2$ | —$C(O)NH_2$ |
| BAZ | —$(CH_2)_2NHSO_2CH_3$ | —$C(O)NH_2$ |
| BBA | —$CH_2CO_2CH_3$ | —$C(O)NH_2$ |
| BBB | —$CH_2CO_2CH_2CH_3$ | —$C(O)NH_2$ |
| BBC | —$(CH_2)_2CO_2CH_3$ | —$C(O)NH_2$ |
| BBD | —$(CH_2)_2CO_2CH_2CH_3$ | —$C(O)NH_2$ |
| BBE | —$(CH_2)_3CO_2CH_3$ | —$C(O)NH_2$ |
| BBF | —$(CH_2)_3CO_2CH_2CH_3$ | —$C(O)NH_2$ |
| BBG | —$(CH_2)_4CO_2CH_3$ | —$C(O)NH_2$ |
| BBH | —$(CH_2)_4CO_2CH_2CH_3$ | —$C(O)NH_2$ |
| BBI | —$CH_2SO_2NH_2$ | —$C(O)NH_2$ |
| BBJ | —$CH_2SO_2N(CH_3)_2$ | —$C(O)NH_2$ |
| BBK | —$(CH_2)_2NHSO_2H$ | —$C(O)NH_2$ |
| BBL | —$(CH_2)_2NHSO_2CH_3$ | —$C(O)NH_2$ |
| BBM | —H | —$CO_2CH_3$ |
| BBN | —$CH_2C(O)NH_2$ | —$CO_2CH_3$ |
| BBO | —$CH_2C(O)N(CH_3)_2$ | —$CO_2CH_3$ |
| BBP | —$C(O)CH_2NHSO_2CH_3$ | —$CO_2CH_3$ |
| BBQ | —$(CH_2)_2C(O)NH_2$ | —$CO_2CH_3$ |
| BBR | —$(CH_2)_2C(O)N(CH_3)_2$ | —$CO_2CH_3$ |
| BBS | —$C(O)(CH_2)_2NHSO_2CH_3$ | —$CO_2CH_3$ |
| BBT | —$CH_2CO_2CH_3$ | —$CO_2CH_3$ |
| BBU | —$CH_2CO_2CH_2CH_3$ | —$CO_2CH_3$ |
| BBV | —$(CH_2)_2CO_2CH_3$ | —$CO_2CH_3$ |
| BBW | —$(CH_2)_2CO_2CH_2CH_3$ | —$CO_2CH_3$ |
| BBX | —$(CH_2)_3CO_2CH_3$ | —$CO_2CH_3$ |
| BBY | —$(CH_2)_3CO_2CH_2CH_3$ | —$CO_2CH_3$ |
| BBZ | —$(CH_2)_4CO_2CH_3$ | —$CO_2CH_3$ |
| BCA | —$(CH_2)_4CO_2CH_2CH_3$ | —$CO_2CH_3$ |
| BCB | —$CH_2SO_2NH_2$ | —$CO_2CH_3$ |
| BCC | —$CH_2SO_2N(CH_3)_2$ | —$CO_2CH_3$ |
| BCD | —$(CH_2)_2NHSO_2H$ | —$CO_2CH_3$ |
| BCE | —$(CH_2)_2NHSO_2CH_3$ | —$CO_2CH_3$ |
| BCF | —H | —CHO |
| BCG | —$CH_2C(O)NH_2$ | —CHO |
| BCH | —$CH_2C(O)N(CH_3)_2$ | —CHO |
| BCI | —$C(O)CH_2NHSO_2CH_3$ | —CHO |
| BCJ | —$(CH_2)_2C(O)NH_2$ | —CHO |
| BCK | —$(CH_2)_2C(O)N(CH_3)_2$ | —CHO |
| BCL | —$C(O)(CH_2)_2NHSO_2CH_3$ | —CHO |
| BCM | —$CH_2CO_2CH_3$ | —CHO |
| BCN | —$CH_2CO_2CH_2CH_3$ | —CHO |
| BCO | —$(CH_2)_2CO_2CH_3$ | —CHO |
| BCP | —$(CH_2)_2CO_2CH_2CH_3$ | —CHO |
| BCQ | —$(CH_2)_3CO_2CH_3$ | —CHO |
| BCR | —$(CH_2)_3CO_2CH_2CH_3$ | —CHO |
| BCS | —$(CH_2)_4CO_2CH_3$ | —CHO |
| BCT | —$(CH_2)_4CO_2CH_2CH_3$ | —CHO |
| BCU | —$CH_2SO_2NH_2$ | —CHO |
| BCV | —$CH_2SO_2N(CH_3)_2$ | —CHO |
| BCW | —$(CH_2)_2NHSO_2H$ | —CHO |
| BCX | —$(CH_2)_2NHSO_2CH_3$ | —CHO |
| BCY | —H | —CN |
| BCZ | —$CH_2C(O)NH_2$ | —CN |
| BDA | —$CH_2C(O)N(CH_3)_2$ | —CN |
| BDB | —$C(O)CH_2NHSO_2CH_3$ | —CN |
| BDC | —$(CH_2)_2C(O)NH_2$ | —CN |
| BDD | —$(CH_2)_2C(O)N(CH_3)_2$ | —CN |
| BDE | —$C(O)(CH_2)_2NHSO_2CH_3$ | —CN |
| BDF | —$CH_2CO_2CH_3$ | —CN |

-continued

| Compound No.: | G: | R₁: |
|---|---|---|
| BDG | —CH₂CO₂CH₂CH₃ | —CN |
| BDH | —(CH₂)₂CO₂CH₃ | —CN |
| BDI | —(CH₂)₂CO₂CH₂CH₃ | —CN |
| BDJ | —(CH₂)₃CO₂CH₃ | —CN |
| BDK | —(CH₂)₃CO₂CH₂CH₃ | —CN |
| BDL | —(CH₂)₄CO₂CH₃ | —CN |
| BDM | —(CH₂)₄CO₂CH₂CH₃ | —CN |
| BDN | —CH₂SO₂NH₂ | —CN |
| BDO | —CH₂SO₂N(CH₃)₂ | —CN |
| BDP | —(CH₂)₂NHSO₂H | —CN |
| BDQ | —(CH₂)₂NHSO₂CH₃ | —CN |
| BDR | —H | —CH₃ |
| BDS | —CH₂C(O)NH₂ | —CH₃ |
| BDT | —CH₂C(O)N(CH₃)₂ | —CH₃ |
| BDU | —C(O)CH₂NHSO₂CH₃ | —CH₃ |
| BDV | —(CH₂)₂C(O)NH₂ | —CH₃ |
| BDW | —(CH₂)₂C(O)N(CH₃)₂ | —CH₃ |
| BDX | —C(O)(CH₂)₂NHSO₂CH₃ | —CH₃ |
| BDY | —CH₂CO₂CH₃ | —CH₃ |
| BDZ | —CH₂CO₂CH₂CH₃ | —CH₃ |
| BEA | —(CH₂)₂CO₂CH₃ | —CH₃ |
| BEB | —(CH₂)₂CO₂CH₂CH₃ | —CH₃ |
| BEC | —(CH₂)₃CO₂CH₃ | —CH₃ |
| BED | —(CH₂)₃CO₂CH₂CH₃ | —CH₃ |
| BEE | —(CH₂)₄CO₂CH₃ | —CH₃ |
| BEF | —(CH₂)₄CO₂CH₂CH₃ | —CH₃ |
| BEG | —CH₂SO₂NH₂ | —CH₃ |
| BEH | —CH₂SO₂N(CH₃)₂ | —CH₃ |
| BEI | —(CH₂)₂NHSO₂H | —CH₃ |
| BEJ | —(CH₂)₂NHSO₂CH₃ | —CH₃ |
| BEK | —H | —C(O)NH(CH₃) |
| BEL | —CH₂C(O)NH₂ | —C(O)NH(CH₃) |
| BEM | —CH₂C(O)N(CH₃)₂ | —C(O)NH(CH₃) |
| BEN | —C(O)CH₂NHSO₂CH₃ | —C(O)NH(CH₃) |
| BEO | —(CH₂)₂C(O)NH₂ | —C(O)NH(CH₃) |
| BEP | —(CH₂)₂C(O)N(CH₃)₂ | —C(O)NH(CH₃) |
| BEQ | —C(O)(CH₂)₂NHSO₂CH₃ | —C(O)NH(CH₃) |
| BER | —CH₂CO₂CH₃ | —C(O)NH(CH₃) |
| BES | —CH₂CO₂CH₂CH₃ | —C(O)NH(CH₃) |
| BET | —(CH₂)₂CO₂CH₃ | —C(O)NH(CH₃) |
| BEU | —(CH₂)₂CO₂CH₂CH₃ | —C(O)NH(CH₃) |
| BEV | —(CH₂)₃CO₂CH₃ | —C(O)NH(CH₃) |
| BEW | —(CH₂)₃CO₂CH₂CH₃ | —C(O)NH(CH₃) |
| BEX | —(CH₂)₄CO₂CH₃ | —C(O)NH(CH₃) |
| BEY | —(CH₂)₄CO₂CH₂CH₃ | —C(O)NH(CH₃) |
| BEZ | —CH₂SO₂NH₂ | —C(O)NH(CH₃) |
| BFA | —CH₂SO₂N(CH₃)₂ | —C(O)NH(CH₃) |
| BFB | —(CH₂)₂NHSO₂H | —C(O)NH(CH₃) |
| BFC | —(CH₂)₂NHSO₂CH₃ | —C(O)NH(CH₃) |
| BFD | —H | —C(O)N(CH₃)₂ |
| BFE | —CH₂C(O)NH₂ | —C(O)N(CH₃)₂ |
| BFF | —CH₂C(O)N(CH₃)₂ | —C(O)N(CH₃)₂ |
| BFG | —C(O)CH₂NHSO₂CH₃ | —C(O)N(CH₃)₂ |
| BFH | —(CH₂)₂C(O)NH₂ | —C(O)N(CH₃)₂ |
| BFI | —(CH₂)₂C(O)N(CH₃)₂ | —C(O)N(CH₃)₂ |
| BFJ | —C(O)(CH₂)₂NHSO₂CH₃ | —C(O)N(CH₃)₂ |
| BFK | —CH₂CO₂CH₃ | —C(O)N(CH₃)₂ |
| BFL | —CH₂CO₂CH₂CH₃ | —C(O)N(CH₃)₂ |
| BFM | —(CH₂)₂CO₂CH₃ | —C(O)N(CH₃)₂ |
| BFN | —(CH₂)₂CO₂CH₂CH₃ | —C(O)N(CH₃)₂ |
| BFO | —(CH₂)₃CO₂CH₃ | —C(O)N(CH₃)₂ |
| BFP | —(CH₂)₃CO₂CH₂CH₃ | —C(O)N(CH₃)₂ |
| BFQ | —(CH₂)₄CO₂CH₃ | —C(O)N(CH₃)₂ |
| BFR | —(CH₂)₄CO₂CH₂CH₃ | —C(O)N(CH₃)₂ |
| BFS | —CH₂SO₂NH₂ | —C(O)N(CH₃)₂ |
| BFT | —CH₂SO₂N(CH₃)₂ | —C(O)N(CH₃)₂ |
| BFU | —(CH₂)₂NHSO₂H | —C(O)N(CH₃)₂ |
| BFV | —(CH₂)₂NHSO₂CH₃ | —C(O)N(CH₃)₂ |
| BFW | —H | —C(O)-N(piperazine)N—CH₃ |
| BFX | —CH₂C(O)NH₂ | —C(O)-N(piperazine)N—CH₃ |
| BFY | —CH₂C(O)N(CH₃)₂ | —C(O)-N(piperazine)N—CH₃ |
| BFZ | —C(O)CH₂NHSO₂CH₃ | —C(O)-N(piperazine)N—CH₃ |
| BGA | —(CH₂)₂C(O)NH₂ | —C(O)-N(piperazine)N—CH₃ |
| BGB | —(CH₂)₂C(O)N(CH₃)₂ | —C(O)-N(piperazine)N—CH₃ |
| BGC | —C(O)(CH₂)₂NHSO₂CH₃ | —C(O)-N(piperazine)N—CH₃ |
| BGD | —CH₂CO₂CH₃ | —C(O)-N(piperazine)N—CH₃ |
| BGE | —CH₂CO₂CH₂CH₃ | —C(O)-N(piperazine)N—CH₃ |
| BGF | —(CH₂)₂CO₂CH₃ | —C(O)-N(piperazine)N—CH₃ |
| BGG | —(CH₂)₂CO₂CH₂CH₃ | —C(O)-N(piperazine)N—CH₃ |
| BGH | —(CH₂)₃CO₂CH₃ | —C(O)-N(piperazine)N—CH₃ |
| BGI | —(CH₂)₃CO₂CH₂CH₃ | —C(O)-N(piperazine)N—CH₃ |
| BGJ | —(CH₂)₄CO₂CH₃ | —C(O)-N(piperazine)N—CH₃ |
| BGK | —(CH₂)₄CO₂CH₂CH₃ | —C(O)-N(piperazine)N—CH₃ |

-continued

| Compound No.: | G: | R₁: |
|---|---|---|
| BGL | —CH₂SO₂NH₂ | 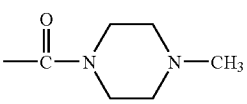 |
| BGM | —CH₂SO₂N(CH₃)₂ | 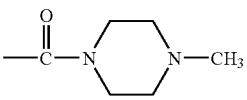 |
| BGN | —(CH₂)₂NHSO₂H | 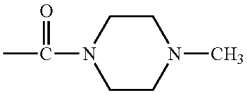 |
| BGO | —(CH₂)₂NHSO₂CH₃ | 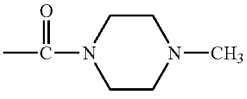 |
| BGP | —H | 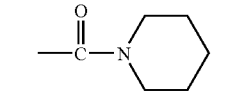 |
| BGQ | —CH₂C(O)NH₂ | 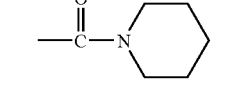 |
| BGR | —CH₂C(O)N(CH₃)₂ | 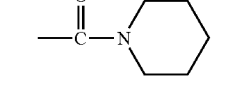 |
| BGS | —C(O)CH₂NHSO₂CH₃ | 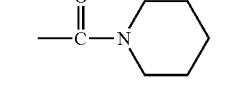 |
| BGT | —(CH₂)₂C(O)NH₂ | 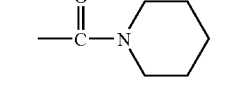 |
| BGU | —(CH₂)₂C(O)N(CH₃)₂ | 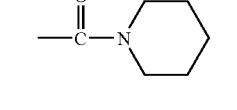 |
| BGV | —C(O)(CH₂)₂NHSO₂CH₃ | 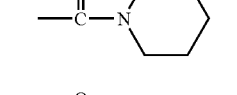 |
| BGW | —CH₂CO₂CH₃ | 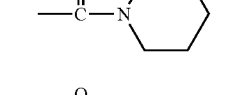 |
| BGX | —CH₂CO₂CH₂CH₃ | 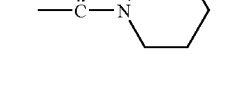 |

-continued

| Compound No.: | G: | R₁: |
|---|---|---|
| BGY | —(CH₂)₂CO₂CH₃ | 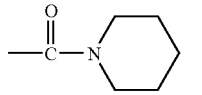 |
| BGZ | —(CH₂)₂CO₂CH₂CH₃ | 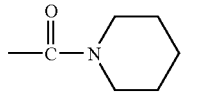 |
| BHA | —(CH₂)₃CO₂CH₃ | 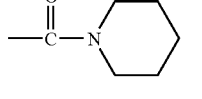 |
| BHB | —(CH₂)₃CO₂CH₂CH₃ | 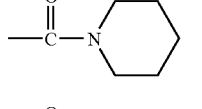 |
| BHC | —(CH₂)₄CO₂CH₃ | 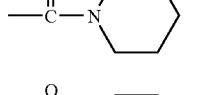 |
| BHD | —(CH₂)₄CO₂CH₂CH₃ | 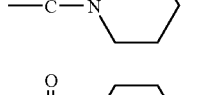 |
| BHE | —CH₂SO₂NH₂ | 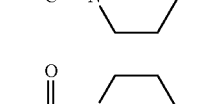 |
| BHF | —CH₂SO₂N(CH₃)₂ | 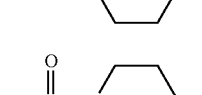 |
| BHG | —(CH₂)₂NHSO₂H | 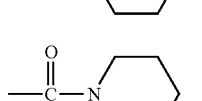 |
| BHH | —(CH₂)₂NHSO₂CH₃ | 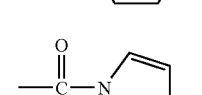 |
| BHI | —H | 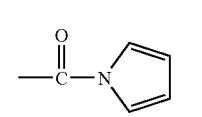 |
| BHJ | —CH₂C(O)NH₂ | 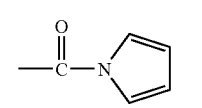 |
| BHK | —CH₂C(O)N(CH₃)₂ | 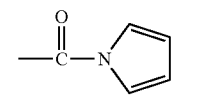 |
| BHL | —C(O)CH₂NHSO₂CH₃ |  |

-continued

| Compound No.: | G: | R₁: |
|---|---|---|
| BHM | —(CH₂)₂C(O)NH₂ | —C(O)-N-pyrrole |
| BHN | —(CH₂)₂C(O)N(CH₃)₂ | —C(O)-N-pyrrole |
| BHO | —C(O)(CH₂)₂NHSO₂CH₃ | —C(O)-N-pyrrole |
| BHP | —CH₂CO₂CH₃ | —C(O)-N-pyrrole |
| BHQ | —CH₂CO₂CH₂CH₃ | —C(O)-N-pyrrole |
| BHR | —(CH₂)₂CO₂CH₃ | —C(O)-N-pyrrole |
| BHS | —(CH₂)₂CO₂CH₂CH₃ | —C(O)-N-pyrrole |
| BHT | —(CH₂)₃CO₂CH₃ | —C(O)-N-pyrrole |
| BHU | —(CH₂)₃CO₂CH₂CH₃ | —C(O)-N-pyrrole |
| BHV | —(CH₂)₄CO₂CH₃ | —C(O)-N-pyrrole |
| BHW | —(CH₂)₄CO₂CH₂CH₃ | —C(O)-N-pyrrole |
| BHX | —CH₂SO₂NH₂ | —C(O)-N-pyrrole |
| BHY | —CH₂SO₂N(CH₃)₂ | —C(O)-N-pyrrole |
| BHZ | —(CH₂)₂NHSO₂H | —C(O)-N-pyrrole |

-continued

| Compound No.: | G: | R₁: |
|---|---|---|
| BIA | —(CH₂)₂NHSO₂CH₃ | —C(O)-N-pyrrole |
| BIB | —H | —C(O)-N-morpholine |
| BIC | —CH₂C(O)NH₂ | —C(O)-N-morpholine |
| BID | —CH₂C(O)N(CH₃)₂ | —C(O)-N-morpholine |
| BIE | —C(O)CH₂NHSO₂CH₃ | —C(O)-N-morpholine |
| BIF | —(CH₂)₂C(O)NH₂ | —C(O)-N-morpholine |
| BIG | —(CH₂)₂C(O)N(CH₃)₂ | —C(O)-N-morpholine |
| BIH | —C(O)(CH₂)₂NHSO₂CH₃ | —C(O)-N-morpholine |
| BII | —CH₂CO₂CH₃ | —C(O)-N-morpholine |
| BIJ | —CH₂CO₂CH₂CH₃ | —C(O)-N-morpholine |
| BIK | —(CH₂)₂CO₂CH₃ | —C(O)-N-morpholine |
| BIL | —(CH₂)₂CO₂CH₂CH₃ | —C(O)-N-morpholine |
| BIM | —(CH₂)₃CO₂CH₃ | —C(O)-N-morpholine |

-continued

| Compound No.: | G: | R₁: |
|---|---|---|
| BIN | —(CH₂)₃CO₂CH₂CH₃ | —C(O)—N(morpholine) |
| BIO | —(CH₂)₄CO₂CH₃ | —C(O)—N(morpholine) |
| BIP | —(CH₂)₄CO₂CH₂CH₃ | —C(O)—N(morpholine) |
| BIQ | —CH₂SO₂NH₂ | —C(O)—N(morpholine) |
| BIR | —CH₂SO₂N(CH₃)₂ | —C(O)—N(morpholine) |
| BIS | —(CH₂)₂NHSO₂H | —C(O)—N(morpholine) |
| BIT | —(CH₂)₂NHSO₂CH₃ | —C(O)—N(morpholine) |
| BIU | —(CH₂)₃NHSO₂H | —H |
| BIV | —(CH₂)₃NHSO₂H | —C(O)NH₂ |
| BIW | —(CH₂)₃NHSO₂H | —CO₂CH₃ |
| BIX | —(CH₂)₃NHSO₂H | —CHO |
| BIY | —(CH₂)₃NHSO₂H | —CN |
| BIZ | —(CH₂)₃NHSO₂H | —CH₃ |
| BJA | —(CH₂)₃NHSO₂H | —C(O)NHCH₃ |
| BJB | —(CH₂)₃NHSO₂H | —C(O)N(CH₃)₂ |
| BJC | —(CH₂)₃NHSO₂H | —C(O)—N(piperazine)—CH₃ |
| BJD | —(CH₂)₃NHSO₂H | —C(O)—N(piperidine) |
| BJE | —(CH₂)₃NHSO₂H | —C(O)—N(pyrrole) |
| BJF | —(CH₂)₃NHSO₂H | —C(O)—N(morpholine) |

The present invention further encompasses compounds having the formula (Ic):

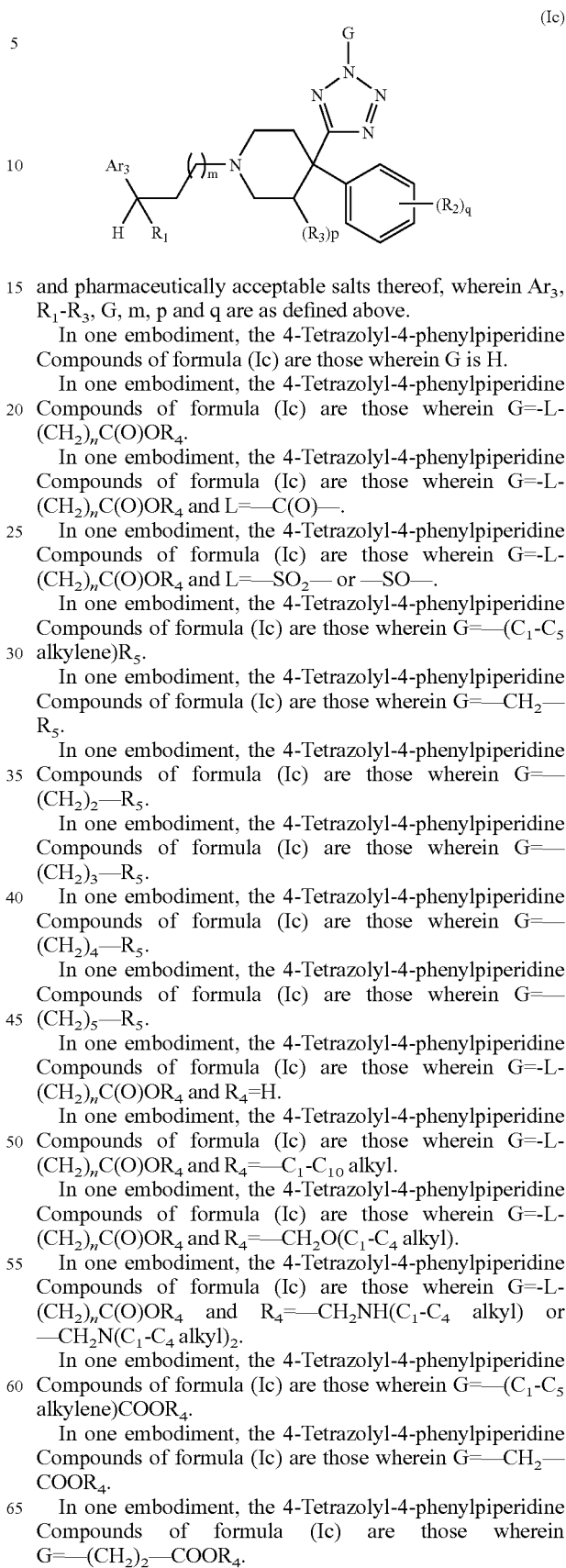

(Ic)

and pharmaceutically acceptable salts thereof, wherein $Ar_3$, $R_1$-$R_3$, G, m, p and q are as defined above.

In one embodiment, the 4-Tetrazolyl-4-phenylpiperidine Compounds of formula (Ic) are those wherein G is H.

In one embodiment, the 4-Tetrazolyl-4-phenylpiperidine Compounds of formula (Ic) are those wherein G=-L-$(CH_2)_nC(O)OR_4$.

In one embodiment, the 4-Tetrazolyl-4-phenylpiperidine Compounds of formula (Ic) are those wherein G=-L-$(CH_2)_nC(O)OR_4$ and L=—C(O)—.

In one embodiment, the 4-Tetrazolyl-4-phenylpiperidine Compounds of formula (Ic) are those wherein G=-L-$(CH_2)_nC(O)OR_4$ and L=—$SO_2$— or —SO—.

In one embodiment, the 4-Tetrazolyl-4-phenylpiperidine Compounds of formula (Ic) are those wherein G=—($C_1$-$C_5$ alkylene)$R_5$.

In one embodiment, the 4-Tetrazolyl-4-phenylpiperidine Compounds of formula (Ic) are those wherein G=—$CH_2$—$R_5$.

In one embodiment, the 4-Tetrazolyl-4-phenylpiperidine Compounds of formula (Ic) are those wherein G=—$(CH_2)_2$—$R_5$.

In one embodiment, the 4-Tetrazolyl-4-phenylpiperidine Compounds of formula (Ic) are those wherein G=—$(CH_2)_3$—$R_5$.

In one embodiment, the 4-Tetrazolyl-4-phenylpiperidine Compounds of formula (Ic) are those wherein G=—$(CH_2)_4$—$R_5$.

In one embodiment, the 4-Tetrazolyl-4-phenylpiperidine Compounds of formula (Ic) are those wherein G=—$(CH_2)_5$—$R_5$.

In one embodiment, the 4-Tetrazolyl-4-phenylpiperidine Compounds of formula (Ic) are those wherein G=-L-$(CH_2)_nC(O)OR_4$ and $R_4$=H.

In one embodiment, the 4-Tetrazolyl-4-phenylpiperidine Compounds of formula (Ic) are those wherein G=-L-$(CH_2)_nC(O)OR_4$ and $R_4$=—$C_1$-$C_{10}$ alkyl.

In one embodiment, the 4-Tetrazolyl-4-phenylpiperidine Compounds of formula (Ic) are those wherein G=-L-$(CH_2)_nC(O)OR_4$ and $R_4$=—$CH_2O(C_1$-$C_4$ alkyl).

In one embodiment, the 4-Tetrazolyl-4-phenylpiperidine Compounds of formula (Ic) are those wherein G=-L-$(CH_2)_nC(O)OR_4$ and $R_4$=—$CH_2NH(C_1$-$C_4$ alkyl) or —$CH_2N(C_1$-$C_4$ alkyl)$_2$.

In one embodiment, the 4-Tetrazolyl-4-phenylpiperidine Compounds of formula (Ic) are those wherein G=—($C_1$-$C_5$ alkylene)$COOR_4$.

In one embodiment, the 4-Tetrazolyl-4-phenylpiperidine Compounds of formula (Ic) are those wherein G=—$CH_2$—$COOR_4$.

In one embodiment, the 4-Tetrazolyl-4-phenylpiperidine Compounds of formula (Ic) are those wherein G=—$(CH_2)_2$—$COOR_4$.

In one embodiment, the 4-Tetrazolyl-4-phenylpiperidine Compounds of formula (Ic) are those wherein G=—(CH$_2$)$_3$—COOR$_4$.

In one embodiment, the 4-Tetrazolyl-4-phenylpiperidine Compounds of formula (Ic) are those wherein G=—(CH$_2$)$_4$—COOR$_4$.

In one embodiment, the 4-Tetrazolyl-4-phenylpiperidine Compounds of formula (Ic) are those wherein G=—(CH$_2$)$_5$—COOR$_4$.

In one embodiment, the 4-Tetrazolyl-4-phenylpiperidine Compounds of formula (Ic) are those wherein G=-L-(CH$_2$)$_n$R$_5$ and R$_5$=—NHSO$_2$R$_4$.

In one embodiment, the 4-Tetrazolyl-4-phenylpiperidine Compounds of formula (Ic) are those wherein G=-L-(CH$_2$)$_n$R$_5$ and R$_5$=—C(O)NH$_2$, —C(O)NHOH, —C(O)NH(C$_1$-C$_4$ alkyl), or —C(O)N(C$_1$-C$_4$ alkyl)$_2$.

In one embodiment, the 4-Tetrazolyl-4-phenylpiperidine Compounds of formula (Ic) are those wherein G=-L-(CH$_2$)$_n$R$_5$ and R$_5$=—SO$_2$NH$_2$, —SO$_2$NH(C$_1$-C$_4$ alkyl), or —SO$_2$N(C$_1$-C$_4$ alkyl)$_2$.

In one embodiment, the 4-Tetrazolyl-4-phenylpiperidine Compounds of formula (Ic) are those wherein G=-L-(CH$_2$)$_n$R$_5$ and R$_5$=—NHSO$_2$H.

In one embodiment, the 4-Tetrazolyl-4-phenylpiperidine Compounds of formula (Ic) are those wherein G=-L-(CH$_2$)$_n$R$_5$ and L=—C(O)—.

In one embodiment, the 4-Tetrazolyl-4-phenylpiperidine Compounds of formula (Ic) are those wherein G=-L-(CH$_2$)$_n$R$_5$ and L=—SO$_2$— or —SO—.

In one embodiment, the 4-Tetrazolyl-4-phenylpiperidine Compounds of formula (Ic) are those wherein G=(C$_1$-C$_5$ alkylene)R$_5$.

In one embodiment, the 4-Tetrazolyl-4-phenylpiperidine Compounds of formula (Ic) are those wherein p=0.

In another embodiment, the 4-Tetrazolyl-4-phenylpiperidine Compounds of formula (Ic) are those wherein p=1.

In another embodiment, the 4-Tetrazolyl-4-phenylpiperidine Compounds of formula (Ic) are those wherein p=1 and the carbon atom to which R$_3$ is attached is in the (R)-configuration.

In another embodiment, the 4-Tetrazolyl-4-phenylpiperidine Compounds of formula (Ic) are those wherein p=1 and the carbon atom to which R$_3$ is attached is in the (S)-configuration.

In another embodiment, the 4-Tetrazolyl-4-phenylpiperidine Compounds of formula (Ic) are those wherein p=1 and R$_3$ is —C$_1$-C$_3$ alkyl.

In another embodiment, the 4-Tetrazolyl-4-phenylpiperidine Compounds of formula (Ic) are those wherein p=1 and R$_3$ is —CH$_3$.

In another embodiment, the 4-Tetrazolyl-4-phenylpiperidine Compounds of formula (Ic) are those wherein p=1, R$_3$ is —C$_1$-C$_3$ alkyl, and the carbon atom to which R$_3$ is attached is in the (R) configuration.

In another embodiment, the 4-Tetrazolyl-4-phenylpiperidine Compounds of formula (Ic) are those wherein p=1, R$_3$ is —CH$_3$, and the carbon atom to which R$_3$ is attached is in the (R) configuration.

In another embodiment, the 4-Tetrazolyl-4-phenylpiperidine Compounds of formula (Ic) are those wherein p=1, R$_3$ is —C$_1$-C$_3$ alkyl, and the carbon atom to which R$_3$ is attached is in the (S) configuration.

In another embodiment, the 4-Tetrazolyl-4-phenylpiperidine Compounds of formula (Ic) are those wherein p=1, R$_3$ is —CH$_3$, and the carbon atom to which R$_3$ is attached is in the (S) configuration.

In one embodiment, the 4-Tetrazolyl-4-phenylpiperidine Compounds of formula (Ic) are those wherein q=0.

In one embodiment, the 4-Tetrazolyl-4-phenylpiperidine Compounds of formula (Ic) are those wherein m=0.

In one embodiment, the 4-Tetrazolyl-4-phenylpiperidine Compounds of formula (Ic) are those wherein m=1.

In one embodiment, the 4-Tetrazolyl-4-phenylpiperidine Compounds of formula (Ic) are those wherein m=0, and p=0.

In one embodiment, the 4-Tetrazolyl-4-phenylpiperidine Compounds of formula (Ic) are those wherein m=1 and p=0.

In one embodiment, the 4-Tetrazolyl-4-phenylpiperidine Compounds of formula (Ic) are those wherein m=0, and q=0.

In one embodiment, the 4-Tetrazolyl-4-phenylpiperidine Compounds of formula (Ic) are those wherein m=1 and q=0.

In one embodiment, the 4-Tetrazolyl-4-phenylpiperidine Compounds of formula (Ic) are those wherein m=0, p=0 and q=0.

In one embodiment, the 4-Tetrazolyl-4-phenylpiperidine Compounds of formula (Ic) are those wherein m=1, p=0 and q=0.

In one embodiment, the 4-Tetrazolyl-4-phenylpiperidine Compounds of formula (Ic) are those wherein R$_2$ is —Br, —Cl, —I, or —F.

In one embodiment, the 4-Tetrazolyl-4-phenylpiperidine Compounds of formula (Ic) are those wherein R$_2$ is —O(C$_1$-C$_3$ alkyl).

In one embodiment, the 4-Tetrazolyl-4-phenylpiperidine Compounds of formula (Ic) are those wherein R$_2$ is —C$_1$-C$_3$ alkyl.

In one embodiment, the 4-Tetrazolyl-4-phenylpiperidine Compounds of formula (Ic) are those wherein R$_3$ is —NH(C$_1$-C$_3$ alkyl) or —N(C$_1$-C$_3$ alkyl)$_2$.

In one embodiment, the 4-Tetrazolyl-4-phenylpiperidine Compounds of formula (Ic) are those wherein R$_3$ is —Br, —Cl, —I, or —F.

In one embodiment, the 4-Tetrazolyl-4-phenylpiperidine Compounds of formula (Ic) are those wherein R$_3$ is —O(C$_1$-C$_3$ alkyl).

In one embodiment, the 4-Tetrazolyl-4-phenylpiperidine Compounds of formula (Ic) are those wherein R$_3$ is —C$_1$-C$_3$ alkyl.

In one embodiment, the 4-Tetrazolyl-4-phenylpiperidine Compounds of formula (Ic) are those wherein R$_3$ is —NH(C$_1$-C$_3$ alkyl) or —N(C$_1$-C$_3$ alkyl)$_2$.

In one embodiment, the 4-Tetrazolyl-4-phenylpiperidine Compounds of formula (Ic) are those wherein R$_1$ is H.

In one embodiment, the 4-Tetrazolyl-4-phenylpiperidine Compounds of formula (Ic) are those wherein R$_1$ is —C(O)NH$_2$, —C(O)NHOH, —C(O)NH(C$_1$-C$_4$ alkyl), or —C(O)N(C$_1$-C$_4$ alkyl)$_2$.

In one embodiment, the 4-Tetrazolyl-4-phenylpiperidine Compounds of formula (Ic) are those wherein R$_1$ is —C(O)N(CH$_3$)$_2$.

In one embodiment, the 4-Tetrazolyl-4-phenylpiperidine Compounds of formula (Ic) are those wherein R$_1$ is —C(O)N(CH$_2$CH$_3$)$_2$.

In one embodiment, the 4-Tetrazolyl-4-phenylpiperidine Compounds of formula (Ic) are those wherein R$_1$ is —C(O)NHCH$_3$.

In one embodiment, the 4-Tetrazolyl-4-phenylpiperidine Compounds of formula (Ic) are those wherein R$_1$ is —C(O)NHCH$_2$CH$_3$.

In one embodiment, the 4-Tetrazolyl-4-phenylpiperidine Compounds of formula (Ic) are those wherein R$_1$ is —COOR$_4$.

In one embodiment, the 4-Tetrazolyl-4-phenylpiperidine Compounds of formula (Ic) are those wherein R$_1$ is —CHO.

In one embodiment, the 4-Tetrazolyl-4-phenylpiperidine Compounds of formula (Ic) are those wherein $R_1$ is —CN.

In one embodiment, the 4-Tetrazolyl-4-phenylpiperidine Compounds of formula (Ic) are those wherein $R_1$ is —($C_1$-$C_4$ alkyl).

In one embodiment, the 4-Tetrazolyl-4-phenylpiperidine Compounds of formula (Ic) are those wherein $R_1$ is

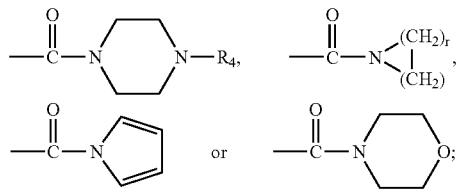

In one embodiment, the 4-Tetrazolyl-4-phenylpiperidine Compounds of formula (Ic) are those wherein $Ar_3$ is phenyl, naphthyl, anthryl, or phenanthryl.

In one embodiment, the 4-Tetrazolyl-4-phenylpiperidine Compounds of formula (Ic) are those wherein $Ar_3$ is -(5- to 7-membered) heteroaryl.

In one embodiment, the 4-Tetrazolyl-4-phenylpiperidine Compounds of formula (Ic) are those wherein $Ar_3$ is substituted with one or more $R_2$ groups. In one embodiment, the 4-Tetrazolyl-4-phenylpiperidine Compounds of formula (Ic) are those wherein G=H, and p=0.

In one embodiment, the 4-Tetrazolyl-4-phenylpiperidine Compounds of formula (Ic) are those wherein G=H, and q=0.

In one embodiment, the 4-Tetrazolyl-4-phenylpiperidine Compounds of formula (Ic) are those wherein G=H, and m=0.

In one embodiment, the 4-Tetrazolyl-4-phenylpiperidine Compounds of formula (Ic) are those wherein G=H, and m=1.

In one embodiment, the 4-Tetrazolyl-4-phenylpiperidine Compounds of formula (Ic) are those wherein G=H, and $Ar_3$ is phenyl.

In one embodiment, the 4-Tetrazolyl-4-phenylpiperidine Compounds of formula (Ic) are those wherein G=H, p=0, and q=0.

In one embodiment, the 4-Tetrazolyl-4-phenylpiperidine Compounds of formula (Ic) are those wherein G=H, p=0, and m=0.

In one embodiment, the 4-Tetrazolyl-4-phenylpiperidine Compounds of formula (Ic) are those wherein G=H, p=0, and m=1.

In one embodiment, the 4-Tetrazolyl-4-phenylpiperidine Compounds of formula (Ic) are those wherein G=H, p=0, and $Ar_3$ is phenyl.

In one embodiment, the 4-Tetrazolyl-4-phenylpiperidine Compounds of formula (Ic) are those wherein G=H, p=0, q=0, and m=0.

In one embodiment, the 4-Tetrazolyl-4-phenylpiperidine Compounds of formula (Ic) are those wherein G=H, p=0, q=0, and m=1.

In one embodiment, the 4-Tetrazolyl-4-phenylpiperidine Compounds of formula (Ic) are those wherein G=H, p=0, q=0, and $Ar_3$ is phenyl.

In one embodiment, the 4-Tetrazolyl-4-phenylpiperidine Compounds of formula (Ic) are those wherein G=H, p=0, q=0, m=0, and $Ar_3$ is phenyl.

Illustrative 4-Tetrazolyl-4-phenylpiperidine Compounds of formula (Ic) have the following structure:

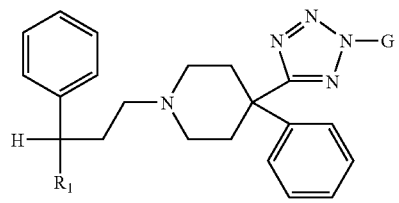

wherein G and $R_1$ are as follows:

| Compound No.: | G: | $R_1$: |
|---|---|---|
| CAA | —H | —H |
| CAB | —$CH_2C(O)NH_2$ | —H |
| CAC | —$CH_2C(O)N(CH_3)_2$ | —H |
| CAD | —$C(O)CH_2NHSO_2CH_3$ | —H |
| CAE | —$(CH_2)_2C(O)NH_2$ | —H |
| CAF | —$(CH_2)_2C(O)N(CH_3)_2$ | —H |
| CAG | —$C(O)(CH_2)_2NHSO_2CH_3$ | —H |
| CAH | —$CH_2CO_2CH_3$ | —H |
| CAI | —$CH_2CO_2CH_2CH_3$ | —H |
| CAJ | —$(CH_2)_2CO_2CH_3$ | —H |
| CAK | —$(CH_2)_2CO_2CH_2CH_3$ | —H |
| CAL | —$(CH_2)_3CO_2CH_3$ | —H |
| CAM | —$(CH_2)_3CO_2CH_2CH_3$ | —H |
| CAN | —$(CH_2)_4CO_2CH_3$ | —H |
| CAO | —$(CH_2)_4CO_2CH_2CH_3$ | —H |
| CAP | —$CH_2SO_2NH_2$ | —H |
| CAQ | —$CH_2SO_2N(CH_3)_2$ | —H |
| CAR | —$(CH_2)_2NHSO_2H$ | —H |
| CAS | —$(CH_2)_2NHSO_2CH_3$ | —H |
| CAT | —H | —$C(O)NH_2$ |
| CAU | —$CH_2C(O)NH_2$ | —$C(O)NH_2$ |
| CAV | —$CH_2C(O)N(CH_3)_2$ | —$C(O)NH_2$ |
| CAW | —$CH_2NHSO_2CH_3$ | —$C(O)NH_2$ |
| CAX | —$(CH_2)_2C(O)NH_2$ | —$C(O)NH_2$ |
| CAY | —$(CH_2)_2C(O)N(CH_3)_2$ | —$C(O)NH_2$ |
| CAZ | —$(CH_2)_2NHSO_2CH_3$ | —$C(O)NH_2$ |
| CBA | —$CH_2CO_2CH_3$ | —$C(O)NH_2$ |
| CBB | —$CH_2CO_2CH_2CH_3$ | —$C(O)NH_2$ |
| CBC | —$(CH_2)_2CO_2CH_3$ | —$C(O)NH_2$ |
| CBD | —$(CH_2)_2CO_2CH_2CH_3$ | —$C(O)NH_2$ |
| CBE | —$(CH_2)_3CO_2CH_3$ | —$C(O)NH_2$ |
| CBF | —$(CH_2)_3CO_2CH_2CH_3$ | —$C(O)NH_2$ |
| CBG | —$(CH_2)_4CO_2CH_3$ | —$C(O)NH_2$ |
| CBH | —$(CH_2)_4CO_2CH_2CH_3$ | —$C(O)NH_2$ |
| CBI | —$CH_2SO_2NH_2$ | —$C(O)NH_2$ |
| CBJ | —$CH_2SO_2N(CH_3)_2$ | —$C(O)NH_2$ |
| CBK | —$(CH_2)_2NHSO_2H$ | —$C(O)NH_2$ |
| CBL | —$(CH_2)_2NHSO_2CH_3$ | —$C(O)NH_2$ |
| CBM | —H | —$CO_2CH_3$ |
| CBN | —$CH_2C(O)NH_2$ | —$CO_2CH_3$ |
| CBO | —$CH_2C(O)N(CH_3)_2$ | —$CO_2CH_3$ |
| CBP | —$C(O)CH_2NHSO_2CH_3$ | —$CO_2CH_3$ |
| CBQ | —$(CH_2)_2C(O)NH_2$ | —$CO_2CH_3$ |
| CBR | —$(CH_2)_2C(O)N(CH_3)_2$ | —$CO_2CH_3$ |
| CBS | —$C(O)(CH_2)_2NHSO_2CH_3$ | —$CO_2CH_3$ |
| CBT | —$CH_2CO_2CH_3$ | —$CO_2CH_3$ |
| CBU | —$CH_2CO_2CH_2CH_3$ | —$CO_2CH_3$ |
| CBV | —$(CH_2)_2CO_2CH_3$ | —$CO_2CH_3$ |
| CBW | —$(CH_2)_2CO_2CH_2CH_3$ | —$CO_2CH_3$ |
| CBX | —$(CH_2)_3CO_2CH_3$ | —$CO_2CH_3$ |
| CBY | —$(CH_2)_3CO_2CH_2CH_3$ | —$CO_2CH_3$ |
| CBZ | —$(CH_2)_4CO_2CH_3$ | —$CO_2CH_3$ |
| CCA | —$(CH_2)_4CO_2CH_2CH_3$ | —$CO_2CH_3$ |
| CCB | —$CH_2SO_2NH_2$ | —$CO_2CH_3$ |
| CCC | —$CH_2SO_2N(CH_3)_2$ | —$CO_2CH_3$ |
| CCD | —$(CH_2)_2NHSO_2H$ | —$CO_2CH_3$ |
| CCE | —$(CH_2)_2NHSO_2CH_3$ | —$CO_2CH_3$ |
| CCF | —H | —CHO |
| CCG | —$CH_2C(O)NH_2$ | —CHO |
| CCH | —$CH_2C(O)N(CH_3)_2$ | —CHO |

-continued

| Compound No.: | G: | R₁: |
|---|---|---|
| CCI | —C(O)CH₂NHSO₂CH₃ | —CHO |
| CCJ | —(CH₂)₂C(O)NH₂ | —CHO |
| CCK | —(CH₂)₂C(O)N(CH₃)₂ | —CHO |
| CCL | —C(O)(CH₂)₂NHSO₂CH₃ | —CHO |
| CCM | —CH₂CO₂CH₃ | —CHO |
| CCN | —CH₂CO₂CH₂CH₃ | —CHO |
| CCO | —(CH₂)₂CO₂CH₃ | —CHO |
| CCP | —(CH₂)₂CO₂CH₂CH₃ | —CHO |
| CCQ | —(CH₂)₃CO₂CH₃ | —CHO |
| CCR | —(CH₂)₃CO₂CH₂CH₃ | —CHO |
| CCS | —(CH₂)₄CO₂CH₃ | —CHO |
| CCT | —(CH₂)₄CO₂CH₂CH₃ | —CHO |
| CCU | —CH₂SO₂NH₂ | —CHO |
| CCV | —CH₂SO₂N(CH₃)₂ | —CHO |
| CCW | —(CH₂)₂NHSO₂H | —CHO |
| CCX | —(CH₂)₂NHSO₂CH₃ | —CHO |
| CCY | —H | —CN |
| CCZ | —CH₂C(O)NH₂ | —CN |
| CDA | —CH₂C(O)N(CH₃)₂ | —CN |
| CDB | —C(O)CH₂NHSO₂CH₃ | —CN |
| CDC | —(CH₂)₂C(O)NH₂ | —CN |
| CDD | —(CH₂)₂C(O)N(CH₃)₂ | —CN |
| CDE | —C(O)(CH₂)₂NHSO₂CH₃ | —CN |
| CDF | —CH₂CO₂CH₃ | —CN |
| CDG | —CH₂CO₂CH₂CH₃ | —CN |
| CDH | —(CH₂)₂CO₂CH₃ | —CN |
| CDI | —(CH₂)₂CO₂CH₂CH₃ | —CN |
| CDJ | —(CH₂)₃CO₂CH₃ | —CN |
| CDK | —(CH₂)₃CO₂CH₂CH₃ | —CN |
| CDL | —(CH₂)₄CO₂CH₃ | —CN |
| CDM | —(CH₂)₄CO₂CH₂CH₃ | —CN |
| CDN | —CH₂SO₂NH₂ | —CN |
| CDO | —CH₂SO₂N(CH₃)₂ | —CN |
| CDP | —(CH₂)₂NHSO₂H | —CN |
| CDQ | —(CH₂)₂NHSO₂CH₃ | —CN |
| CDR | —H | —CH₃ |
| CDS | —CH₂C(O)NH₂ | —CH₃ |
| CDT | —CH₂C(O)N(CH₃)₂ | —CH₃ |
| CDU | —C(O)CH₂NHSO₂CH₃ | —CH₃ |
| CDV | —(CH₂)₂C(O)NH₂ | —CH₃ |
| CDW | —(CH₂)₂C(O)N(CH₃)₂ | —CH₃ |
| CDX | —C(O)(CH₂)₂NHSO₂CH₃ | —CH₃ |
| CDY | —CH₂CO₂CH₃ | —CH₃ |
| CDZ | —CH₂CO₂CH₂CH₃ | —CH₃ |
| CEA | —(CH₂)₂CO₂CH₃ | —CH₃ |
| CEB | —(CH₂)₂CO₂CH₂CH₃ | —CH₃ |
| CEC | —(CH₂)₃CO₂CH₃ | —CH₃ |
| CED | —(CH₂)₃CO₂CH₂CH₃ | —CH₃ |
| CEE | —(CH₂)₄CO₂CH₃ | —CH₃ |
| CEF | —(CH₂)₄CO₂CH₂CH₃ | —CH₃ |
| CEG | —CH₂SO₂NH₂ | —CH₃ |
| CEH | —CH₂SO₂N(CH₃)₂ | —CH₃ |
| CEI | —(CH₂)₂NHSO₂H | —CH₃ |
| CEJ | —(CH₂)₂NHSO₂CH₃ | —CH₃ |
| CEK | —H | —C(O)NH(CH₃) |
| CEL | —CH₂C(O)NH₂ | —C(O)NH(CH₃) |
| CEM | —CH₂C(O)N(CH₃)₂ | —C(O)NH(CH₃) |
| CEN | —C(O)CH₂NHSO₂CH₃ | —C(O)NH(CH₃) |
| CEO | —(CH₂)₂C(O)NH₂ | —C(O)NH(CH₃) |
| CEP | —(CH₂)₂C(O)N(CH₃)₂ | —C(O)NH(CH₃) |
| CEQ | —C(O)(CH₂)₂NHSO₂CH₃ | —C(O)NH(CH₃) |
| CER | —CH₂CO₂CH₃ | —C(O)NH(CH₃) |
| CES | —CH₂CO₂CH₂CH₃ | —C(O)NH(CH₃) |
| CET | —(CH₂)₂CO₂CH₃ | —C(O)NH(CH₃) |
| CEU | —(CH₂)₂CO₂CH₂CH₃ | —C(O)NH(CH₃) |
| CEV | —(CH₂)₃CO₂CH₃ | —C(O)NH(CH₃) |
| CEW | —(CH₂)₃CO₂CH₂CH₃ | —C(O)NH(CH₃) |
| CEX | —(CH₂)₄CO₂CH₃ | —C(O)NH(CH₃) |
| CEY | —(CH₂)₄CO₂CH₂CH₃ | —C(O)NH(CH₃) |
| CEZ | —CH₂SO₂NH₂ | —C(O)NH(CH₃) |
| CFA | —CH₂SO₂N(CH₃)₂ | —C(O)NH(CH₃) |
| CFB | —(CH₂)₂NHSO₂H | —C(O)NH(CH₃) |
| CFC | —(CH₂)₂NHSO₂CH₃ | —C(O)NH(CH₃) |
| CFD | —H | —C(O)N(CH₃)₂ |
| CFE | —CH₂C(O)NH₂ | —C(O)N(CH₃)₂ |
| CFF | —CH₂C(O)N(CH₃)₂ | —C(O)N(CH₃)₂ |

-continued

| Compound No.: | G: | R₁: |
|---|---|---|
| CFG | —C(O)CH₂NHSO₂CH₃ | —C(O)N(CH₃)₂ |
| CFH | —(CH₂)₂C(O)NH₂ | —C(O)N(CH₃)₂ |
| CFI | —(CH₂)₂C(O)N(CH₃)₂ | —C(O)N(CH₃)₂ |
| CFJ | —C(O)(CH₂)₂NHSO₂CH₃ | —C(O)N(CH₃)₂ |
| CFK | —CH₂CO₂CH₃ | —C(O)N(CH₃)₂ |
| CFL | —CH₂CO₂CH₂CH₃ | —C(O)N(CH₃)₂ |
| CFM | —(CH₂)₂CO₂CH₃ | —C(O)N(CH₃)₂ |
| CFN | —(CH₂)₂CO₂CH₂CH₃ | —C(O)N(CH₃)₂ |
| CFO | —(CH₂)₃CO₂CH₃ | —C(O)N(CH₃)₂ |
| CFP | —(CH₂)₃CO₂CH₂CH₃ | —C(O)N(CH₃)₂ |
| CFQ | —(CH₂)₄CO₂CH₃ | —C(O)N(CH₃)₂ |
| CFR | —(CH₂)₄CO₂CH₂CH₃ | —C(O)N(CH₃)₂ |
| CFS | —CH₂SO₂NH₂ | —C(O)N(CH₃)₂ |
| CFT | —CH₂SO₂N(CH₃)₂ | —C(O)N(CH₃)₂ |
| CFU | —(CH₂)₂NHSO₂H | —C(O)N(CH₃)₂ |
| CFV | —(CH₂)₂NHSO₂CH₃ | —C(O)N(CH₃)₂ |
| CFW | —H | 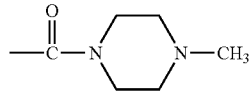 |
| CFX | —CH₂C(O)NH₂ | 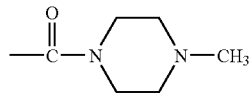 |
| CFY | —CH₂C(O)N(CH₃)₂ | |
| CFZ | —C(O)CH₂NHSO₂CH₃ | 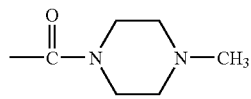 |
| CGA | —(CH₂)₂C(O)NH₂ | |
| CGB | —(CH₂)₂C(O)N(CH₃)₂ | 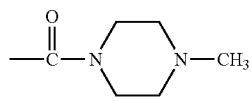 |
| CGC | —C(O)(CH₂)₂NHSO₂CH₃ | |
| CGD | —CH₂CO₂CH₃ | 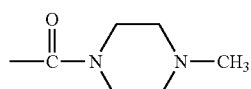 |
| CGE | —CH₂CO₂CH₂CH₃ | |
| CGF | —(CH₂)₂CO₂CH₃ | 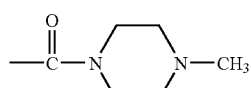 |

| Compound No.: | G: | R₁: |
|---|---|---|
| CGG | —(CH₂)₂CO₂CH₂CH₃ | 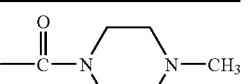 |
| CGH | —(CH₂)₃CO₂CH₃ |  |
| CGI | —(CH₂)₃CO₂CH₂CH₃ | 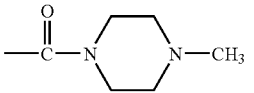 |
| CGJ | —(CH₂)₄CO₂CH₃ |  |
| CGK | —(CH₂)₄CO₂CH₂CH₃ | 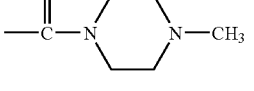 |
| CGL | —CH₂SO₂NH₂ | 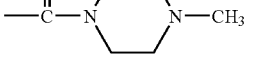 |
| CGM | —CH₂SO₂N(CH₃)₂ | 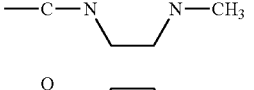 |
| CGN | —(CH₂)₂NHSO₂H | 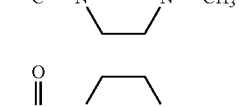 |
| CGO | —(CH₂)₂NHSO₂CH₃ | 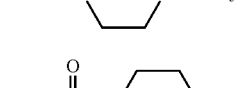 |
| CGP | —H | 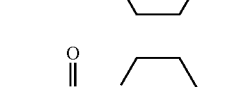 |
| CGQ | —CH₂C(O)NH₂ | 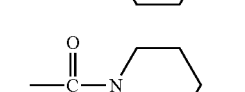 |
| CGR | —CH₂C(O)N(CH₃)₂ | 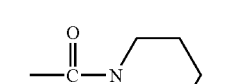 |
| CGS | —C(O)CH₂NHSO₂CH₃ | 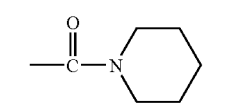 |
| CGT | —(CH₂)₂C(O)NH₂ |  |
| CGU | —(CH₂)₂C(O)N(CH₃)₂ | 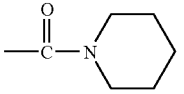 |
| CGV | —C(O)(CH₂)₂NHSO₂CH₃ | 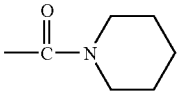 |
| CGW | —CH₂CO₂CH₃ | 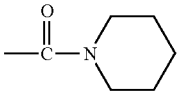 |
| CGX | —CH₂CO₂CH₂CH₃ | 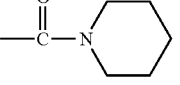 |
| CGY | —(CH₂)₂CO₂CH₃ | 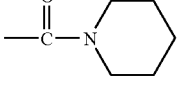 |
| CGZ | —(CH₂)₂CO₂CH₂CH₃ | 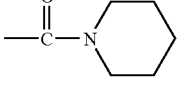 |
| CHA | —(CH₂)₃CO₂CH₃ | 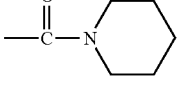 |
| CHB | —(CH₂)₃CO₂CH₂CH₃ | 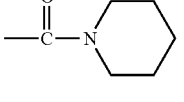 |
| CHC | —(CH₂)₄CO₂CH₃ | 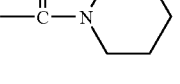 |
| CHD | —(CH₂)₄CO₂CH₂CH₃ | 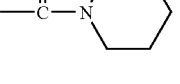 |
| CHE | —CH₂SO₂NH₂ | 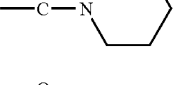 |
| CHF | —CH₂SO₂N(CH₃)₂ | 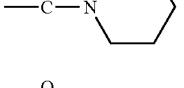 |
| CHG | —(CH₂)₂NHSO₂H | 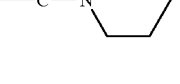 |

-continued

| Compound No.: | G: | R₁: |
|---|---|---|
| CHH | —(CH₂)₂NHSO₂CH₃ | 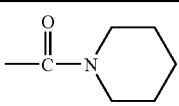 |
| CHI | —H | 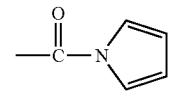 |
| CHJ | —CH₂C(O)NH₂ | 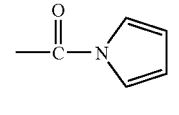 |
| CHK | —CH₂C(O)N(CH₃)₂ | 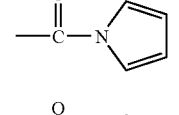 |
| CHL | —C(O)CH₂NHSO₂CH₃ | 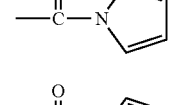 |
| CHM | —(CH₂)₂C(O)NH₂ | 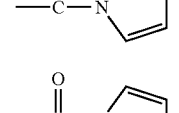 |
| CHN | —(CH₂)₂C(O)N(CH₃)₂ | 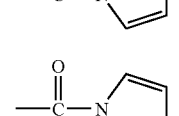 |
| CHO | —C(O)(CH₂)₂NHSO₂CH₃ | 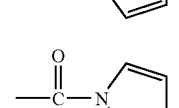 |
| CHP | —CH₂CO₂CH₃ | 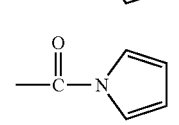 |
| CHQ | —CH₂CO₂CH₂CH₃ | 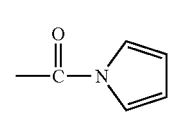 |
| CHR | —(CH₂)₂CO₂CH₃ | 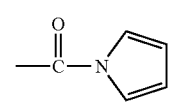 |
| CHS | —(CH₂)₂CO₂CH₂CH₃ | 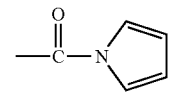 |
| CHT | —(CH₂)₃CO₂CH₃ | 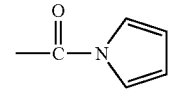 |
| CHU | —(CH₂)₃CO₂CH₂CH₃ |  |

-continued

| Compound No.: | G: | R₁: |
|---|---|---|
| CHV | —(CH₂)₄CO₂CH₃ | 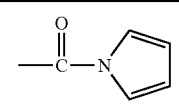 |
| CHW | —(CH₂)₄CO₂CH₂CH₃ | 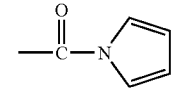 |
| CHX | —CH₂SO₂NH₂ | 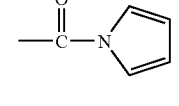 |
| CHY | —CH₂SO₂N(CH₃)₂ | 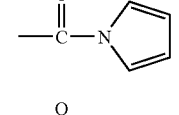 |
| CHZ | —(CH₂)₂NHSO₂H | 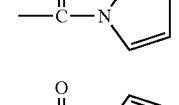 |
| CIA | —(CH₂)₂NHSO₂CH₃ | 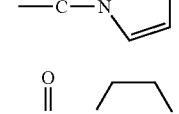 |
| CIB | —H | 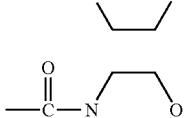 |
| CIC | —CH₂C(O)NH₂ | 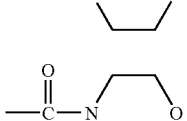 |
| CID | —CH₂C(O)N(CH₃)₂ | 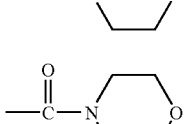 |
| CIE | —C(O)CH₂NHSO₂CH₃ | 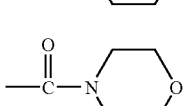 |
| CIF | —(CH₂)₂C(O)NH₂ | 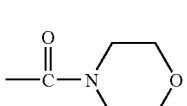 |
| CIG | —(CH₂)₂C(O)N(CH₃)₂ | 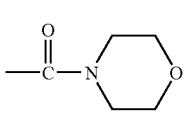 |
| CIH | —C(O)(CH₂)₂NHSO₂CH₃ | 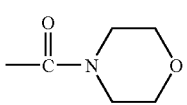 |
| CII | —CH₂CO₂CH₃ |  |

-continued

| Compound No.: | G: | R₁: |
|---|---|---|
| CIJ | —CH₂CO₂CH₂CH₃ | —C(O)-N-morpholine |
| CIK | —(CH₂)₂CO₂CH₃ | —C(O)-N-morpholine |
| CIL | —(CH₂)₂CO₂CH₂CH₃ | —C(O)-N-morpholine |
| CIM | —(CH₂)₃CO₂CH₃ | —C(O)-N-morpholine |
| CIN | —(CH₂)₃CO₂CH₂CH₃ | —C(O)-N-morpholine |
| CIO | —(CH₂)₄CO₂CH₃ | —C(O)-N-morpholine |
| CIP | —(CH₂)₄CO₂CH₂CH₃ | —C(O)-N-morpholine |
| CIQ | —CH₂SO₂NH₂ | —C(O)-N-morpholine |
| CIR | —CH₂SO₂N(CH₃)₂ | —C(O)-N-morpholine |
| CIS | —(CH₂)₂NHSO₂H | —C(O)-N-morpholine |
| CIT | —(CH₂)₂NHSO₂CH₃ | —C(O)-N-morpholine |
| CIU | —(CH₂)₃NHSO₂H | —H |
| CIV | —(CH₂)₃NHSO₂H | —C(O)NH₂ |
| CIW | —(CH₂)₃NHSO₂H | —CO₂CH₃ |
| CIX | —(CH₂)₃NHSO₂H | —CHO |
| CIY | —(CH₂)₃NHSO₂H | —CN |
| CIZ | —(CH₂)₃NHSO₂H | —CH₃ |
| CJA | —(CH₂)₃NHSO₂H | —C(O)NHCH₃ |
| CJB | —(CH₂)₃NHSO₂H | —C(O)N(CH₃)₂ |
| CJC | —(CH₂)₃NHSO₂H | —C(O)-N-methylpiperazine |
| CJD | —(CH₂)₃NHSO₂H | —C(O)-N-piperidine |
| CJE | —(CH₂)₃NHSO₂H | —C(O)-N-pyrrole |
| CJF | —(CH₂)₃NHSO₂H | —C(O)-N-morpholine |

The present invention further encompasses compounds having the formula (Id)

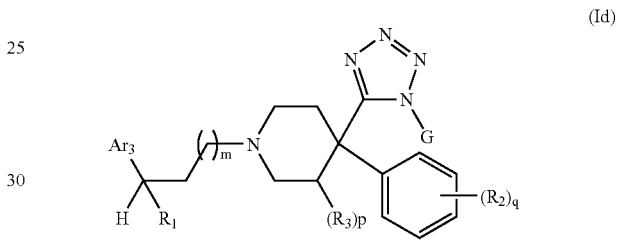

(Id)

and pharmaceutically acceptable salts thereof, wherein $Ar_3$, $R_1$-$R_3$ G, m, p, and q, are as defined above.

In one embodiment, the 4-Tetrazolyl-4-phenylpiperidine Compounds of formula (Id) are those wherein G is H.

In one embodiment, the 4-Tetrazolyl-4-phenylpiperidine Compounds of formula (Id) are those wherein G=-L-$(CH_2)_nC(O)OR_4$.

In one embodiment, the 4-Tetrazolyl-4-phenylpiperidine Compounds of formula (Id) are those wherein G=-L-$(CH_2)_nC(O)OR_4$ and L=—C(O)—.

In one embodiment, the 4-Tetrazolyl-4-phenylpiperidine Compounds of formula (Id) are those wherein G=-L-$(CH_2)_nC(O)OR_4$ and L=—SO₂— or —SO—.

In one embodiment, the 4-Tetrazolyl-4-phenylpiperidine Compounds of formula (Id) are those wherein G=-L-$(CH_2)_nC(O)OR_4$ and $R_4$=H.

In one embodiment, the 4-Tetrazolyl-4-phenylpiperidine Compounds of formula (Id) are those wherein G=-L-$(CH_2)_nC(O)OR_4$ and $R_4$=—$C_1$-$C_{10}$ alkyl.

In one embodiment, the 4-Tetrazolyl-4-phenylpiperidine Compounds of formula (Id) are those wherein G=-L-$(CH_2)_nC(O)OR_4$ and $R_4$=—$CH_2O(C_1$-$C_4$ alkyl).

In one embodiment, the 4-Tetrazolyl-4-phenylpiperidine Compounds of formula (Id) are those wherein G=-L-$(CH_2)_nC(O)OR_4$ and $R_4$=—$CH_2NH(C_1$-$C_4$ alkyl) or —$CH_2N(C_1$-$C_4$ alkyl)₂.

In one embodiment, the 4-Tetrazolyl-4-phenylpiperidine Compounds of formula (Id) are those wherein G=—($C_1$-$C_5$ alkylene)$COOR_4$.

In one embodiment, the 4-Tetrazolyl-4-phenylpiperidine Compounds of formula (Id) are those wherein G=—$CH_2$—$COOR_4$.

In one embodiment, the 4-Tetrazolyl-4-phenylpiperidine Compounds of formula (Id) are those wherein G=—(CH$_2$)$_2$—COOR$_4$.

In one embodiment, the 4-Tetrazolyl-4-phenylpiperidine Compounds of formula (Id) are those wherein G=—(CH$_2$)$_3$—COOR$_4$.

In one embodiment, the 4-Tetrazolyl-4-phenylpiperidine Compounds of formula (Id) are those wherein G=—(CH$_2$)$_4$—COOR$_4$.

In one embodiment, the 4-Tetrazolyl-4-phenylpiperidine Compounds of formula (Id) are those wherein G=—(CH$_2$)$_5$—COOR$_4$.

In one embodiment, the 4-Tetrazolyl-4-phenylpiperidine Compounds of formula (Id) are those wherein G is -L-(CH$_2$)$_n$R$_5$ and R$_5$=—NHSO$_2$R$_4$.

In one embodiment, the 4-Tetrazolyl-4-phenylpiperidine Compounds of formula (Id) are those wherein G is -L-(CH$_2$)$_n$R$_5$ and R$_5$=—C(O)NH$_2$, —C(O)NHOH, —C(O)NH(C$_1$-C$_4$ alkyl), or —C(O)N(C$_1$-C$_4$ alkyl)$_2$.

In one embodiment, the 4-Tetrazolyl-4-phenylpiperidine Compounds of formula (Id) are those wherein G is -L-(CH$_2$)$_n$R$_5$ and R$_5$=—SO$_2$NH$_2$, —SO$_2$NH(C$_1$-C$_4$ alkyl), or —SO$_2$N(C$_1$-C$_4$ alkyl)$_2$.

In one embodiment, the 4-Tetrazolyl-4-phenylpiperidine Compounds of formula (Id) are those wherein G is -L-(CH$_2$)$_n$R$_5$ and R$_5$=—NHSO$_2$H.

In one embodiment, the 4-Tetrazolyl-4-phenylpiperidine Compounds of formula (Id) are those wherein G is -L-(CH$_2$)$_n$R$_5$ and L=—C(O)—.

In one embodiment, the 4-Tetrazolyl-4-phenylpiperidine Compounds of formula (Id) are those wherein G is -L-(CH$_2$)$_n$R$_5$ and L=—SO$_2$— or —SO—.

In one embodiment, the 4-Tetrazolyl-4-phenylpiperidine Compounds of formula (Id) are those wherein G=—(C$_1$-C$_5$ alkylene)R$_5$.

In one embodiment, the 4-Tetrazolyl-4-phenylpiperidine Compounds of formula (Id) are those wherein G=—CH$_2$—R$_5$.

In one embodiment, the 4-Tetrazolyl-4-phenylpiperidine Compounds of formula (Id) are those wherein G=—(CH$_2$)$_2$—R$_5$.

In one embodiment, the 4-Tetrazolyl-4-phenylpiperidine Compounds of formula (Id) are those wherein G=—(CH$_2$)$_3$—R$_5$.

In one embodiment, the 4-Tetrazolyl-4-phenylpiperidine Compounds of formula (Id) are those wherein G=—(CH$_2$)$_4$—R$_5$.

In one embodiment, the 4-Tetrazolyl-4-phenylpiperidine Compounds of formula (Id) are those wherein G=—(CH$_2$)$_5$—R$_5$.

In one embodiment, the 4-Tetrazolyl-4-phenylpiperidine Compounds of formula (Id) are those wherein p=0.

In another embodiment, the 4-Tetrazolyl-4-phenylpiperidine Compounds of formula (Id) are those wherein p=1.

In another embodiment, the 4-Tetrazolyl-4-phenylpiperidine Compounds of formula (Id) are those wherein p=1 and the carbon atom to which R$_3$ is attached is in the (R)-configuration.

In another embodiment, the 4-Tetrazolyl-4-phenylpiperidine Compounds of formula (Id) are those wherein p=1 and the carbon atom to which R$_3$ is attached is in the (S)-configuration.

In another embodiment, the 4-Tetrazolyl-4-phenylpiperidine Compounds of formula (Id) are those wherein p=1 and R$_3$ is —C$_1$-C$_3$ alkyl.

In another embodiment, the 4-Tetrazolyl-4-phenylpiperidine Compounds of formula (Id) are those wherein p=1 and R$_3$ is —CH$_3$.

In another embodiment, the 4-Tetrazolyl-4-phenylpiperidine Compounds of formula (Id) are those wherein p=1, R$_3$ is —C$_1$-C$_3$ alkyl, and the carbon atom to which R$_3$ is attached is in the (R) configuration.

In another embodiment, the 4-Tetrazolyl-4-phenylpiperidine Compounds of formula (Id) are those wherein p=1, R$_3$ is —CH$_3$, and the carbon atom to which R$_3$ is attached is in the (R) configuration.

In another embodiment, the 4-Tetrazolyl-4-phenylpiperidine Compounds of formula (Id) are those wherein p=1, R$_3$ is —C$_1$-C$_3$ alkyl, and the carbon atom to which R$_3$ is attached is in the (S) configuration.

In another embodiment, the 4-Tetrazolyl-4-phenylpiperidine Compounds of formula (Id) are those wherein p=1, R$_3$ is —CH$_3$, and the carbon atom to which R$_3$ is attached is in the (S) configuration.

In one embodiment, the 4-Tetrazolyl-4-phenylpiperidine Compounds of formula (Id) are those wherein q=0.

In one embodiment, the 4-Tetrazolyl-4-phenylpiperidine Compounds of formula (Id) are those wherein m=0.

In one embodiment, the 4-Tetrazolyl-4-phenylpiperidine Compounds of formula (Id) are those wherein m=1.

In one embodiment, the 4-Tetrazolyl-4-phenylpiperidine Compounds of formula (Id) are those wherein m=0, and p=0.

In one embodiment, the 4-Tetrazolyl-4-phenylpiperidine Compounds of formula (Id) are those wherein m=1 and p=0.

In one embodiment, the 4-Tetrazolyl-4-phenylpiperidine Compounds of formula (Id) are those wherein m=0, and q=0.

In one embodiment, the 4-Tetrazolyl-4-phenylpiperidine Compounds of formula (Id) are those wherein m=1 and q=0.

In one embodiment, the 4-Tetrazolyl-4-phenylpiperidine Compounds of formula (Id) are those wherein m=0, p=0 and q=0.

In one embodiment, the 4-Tetrazolyl-4-phenylpiperidine Compounds of formula (Id) are those wherein m=1, p=0 and q=0.

In one embodiment, the 4-Tetrazolyl-4-phenylpiperidine Compounds of formula (Id) are those wherein R$_2$ is —Br, —Cl, —I, or —F.

In one embodiment, the 4-Tetrazolyl-4-phenylpiperidine Compounds of formula (Id) are those wherein R$_2$ is —O(C$_1$-C$_3$ alkyl).

In one embodiment, the 4-Tetrazolyl-4-phenylpiperidine Compounds of formula (Id) are those wherein R$_2$ is —C$_1$-C$_3$ alkyl.

In one embodiment, the 4-Tetrazolyl-4-phenylpiperidine Compounds of formula (Id) are those wherein R$_2$ is —NH(C$_1$-C$_3$ alkyl) or —N(C$_1$-C$_3$ alkyl)$_2$.

In one embodiment, the 4-Tetrazolyl-4-phenylpiperidine Compounds of formula (Id) are those wherein R$_3$ is —Br, —Cl, —I, or —F.

In one embodiment, the 4-Tetrazolyl-4-phenylpiperidine Compounds of formula (Id) are those wherein R$_3$ is —O(C$_1$-C$_3$ alkyl).

In one embodiment, the 4-Tetrazolyl-4-phenylpiperidine Compounds of formula (Id) are those wherein R$_3$ is —C$_1$-C$_3$ alkyl.

In one embodiment, the 4-Tetrazolyl-4-phenylpiperidine Compounds of formula (Id) are those wherein R$_3$ is —NH(C$_1$-C$_3$ alkyl) or —N(C$_1$-C$_3$ alkyl)$_2$.

In one embodiment, the 4-Tetrazolyl-4-phenylpiperidine Compounds of formula (Id) are those wherein R$_1$ is H.

In one embodiment, the 4-Tetrazolyl-4-phenylpiperidine Compounds of formula (Id) are those wherein $R_1$ is —C(O)NH$_2$, —C(O)NHOH, —C(O)NH(C$_1$-C$_4$ alkyl), or —C(O)N(C$_1$-C$_4$ alkyl)$_2$.

In one embodiment, the 4-Tetrazolyl-4-phenylpiperidine Compounds of formula (Id) are those wherein $R_1$ is —C(O)N(CH$_3$)$_2$.

In one embodiment, the 4-Tetrazolyl-4-phenylpiperidine Compounds of formula (Id) are those wherein $R_1$ is —C(O)NHCH$_3$.

In one embodiment, the 4-Tetrazolyl-4-phenylpiperidine Compounds of formula (Id) are those wherein $R_1$ is —C(O)NHCH$_2$CH$_3$.

In one embodiment, the 4-Tetrazolyl-4-phenylpiperidine Compounds of formula (Id) are those wherein $R_1$ is —C(O)N(CH$_2$CH$_3$)$_2$.

In one embodiment, the 4-Tetrazolyl-4-phenylpiperidine Compounds of formula (Id) are those wherein $R_1$ is —COOR$_4$.

In one embodiment, the 4-Tetrazolyl-4-phenylpiperidine Compounds of formula (Id) are those wherein $R_1$ is —CHO.

In one embodiment, the 4-Tetrazolyl-4-phenylpiperidine Compounds of formula (Id) are those wherein $R_1$ is —CN.

In one embodiment, the 4-Tetrazolyl-4-phenylpiperidine Compounds of formula (Id) are those wherein $R_1$ is —(C$_1$-C$_4$ alkyl).

In one embodiment, the 4-Tetrazolyl-4-phenylpiperidine Compounds of formula (Id) are those wherein $R_1$ is

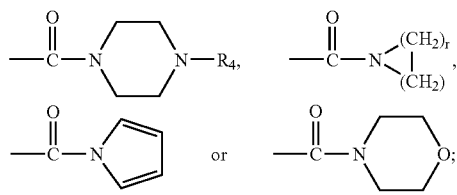

In one embodiment, the 4-Tetrazolyl-4-phenylpiperidine Compounds of formula (Id) are those wherein Ar$_3$ is phenyl, naphthyl, anthryl, or phenanthryl.

In one embodiment, the 4-Tetrazolyl-4-phenylpiperidine Compounds of formula (Id) are those wherein Ar$_3$ is -(5- to 7-membered) heteroaryl.

In one embodiment, the 4-Tetrazolyl-4-phenylpiperidine Compounds of formula (Id) are those wherein Ar$_3$ is substituted with one or more $R_2$ groups.

In one embodiment, the 4-Tetrazolyl-4-phenylpiperidine Compounds of formula (Id) are those wherein G=H, and p=0.

In one embodiment, the 4-Tetrazolyl-4-phenylpiperidine Compounds of formula (Id) are those wherein G=H, and q=0.

In one embodiment, the 4-Tetrazolyl-4-phenylpiperidine Compounds of formula (Id) are those wherein G=H, and m=0.

In one embodiment, the 4-Tetrazolyl-4-phenylpiperidine Compounds of formula (Id) are those wherein G=H, and m=1.

In one embodiment, the 4-Tetrazolyl-4-phenylpiperidine Compounds of formula (Id) are those wherein G=H, and Ar$_3$ is phenyl.

In one embodiment, the 4-Tetrazolyl-4-phenylpiperidine Compounds of formula (Id) are those wherein G=H, p=0, and q=0.

In one embodiment, the 4-Tetrazolyl-4-phenylpiperidine Compounds of formula (Id) are those wherein G=H, p=0, and m=0.

In one embodiment, the 4-Tetrazolyl-4-phenylpiperidine Compounds of formula (Id) are those wherein G=H, p=0, and m=1.

In one embodiment, the 4-Tetrazolyl-4-phenylpiperidine Compounds of formula (Id) are those wherein G=H, p=0, and Ar$_3$ is phenyl.

In one embodiment, the 4-Tetrazolyl-4-phenylpiperidine Compounds of formula (Id) are those wherein G=H, p=0, q=0, and m=0.

In one embodiment, the 4-Tetrazolyl-4-phenylpiperidine Compounds of formula (Id) are those wherein G=H, p=0, q=0, and m=1.

In one embodiment, the 4-Tetrazolyl-4-phenylpiperidine Compounds of formula (Id) are those wherein G=H, p=0, q=0, and Ar$_3$ is phenyl.

In one embodiment, the 4-Tetrazolyl-4-phenylpiperidine Compounds of formula (Id) are those wherein G=H, p=0, q=0, m=0, and Ar$_3$ is phenyl.

Illustrative 4-Tetrazolyl-4-phenylpiperidine Compounds of formula (Id) have the following structure:

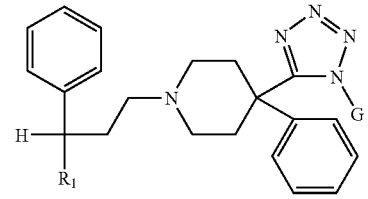

and pharmaceutically acceptable salts thereof, wherein G and $R_1$ are as follows:

| Compound No.: | G: | $R_1$: |
|---|---|---|
| DAA | —H | —H |
| DAB | —CH$_2$C(O)NH$_2$ | —H |
| DAC | —CH$_2$C(O)N(CH$_3$)$_2$ | —H |
| DAD | —C(O)CH$_2$NHSO$_2$CH$_3$ | —H |
| DAE | —(CH$_2$)$_2$C(O)NH$_2$ | —H |
| DAF | —(CH$_2$)$_2$C(O)N(CH$_3$)$_2$ | —H |
| DAG | —C(O)(CH$_2$)$_2$NHSO$_2$CH$_3$ | —H |
| DAH | —CH$_2$CO$_2$CH$_3$ | —H |
| DAI | —CH$_2$CO$_2$CH$_2$CH$_3$ | —H |
| DAJ | —(CH$_2$)$_2$CO$_2$CH$_3$ | —H |
| DAK | —(CH$_2$)$_2$CO$_2$CH$_2$CH$_3$ | —H |
| DAL | —(CH$_2$)$_3$CO$_2$CH$_3$ | —H |
| DAM | —(CH$_2$)$_3$CO$_2$CH$_2$CH$_3$ | —H |

| Compound No.: | G: | $R_1$: |
|---|---|---|
| DAN | $-(CH_2)_4CO_2CH_3$ | $-H$ |
| DAO | $-(CH_2)_4CO_2CH_2CH_3$ | $-H$ |
| DAP | $-CH_2SO_2NH_2$ | $-H$ |
| DAQ | $-CH_2SO_2N(CH_3)_2$ | $-H$ |
| DAR | $-(CH_2)_2NHSO_2H$ | $-H$ |
| DAS | $-(CH_2)_2NHSO_2CH_3$ | $-H$ |
| DAT | $-H$ | $-C(O)NH_2$ |
| DAU | $-CH_2C(O)NH_2$ | $-C(O)NH_2$ |
| DAV | $-CH_2C(O)N(CH_3)_2$ | $-C(O)NH_2$ |
| DAW | $-C(O)CH_2NHSO_2CH_3$ | $-C(O)NH_2$ |
| DAX | $-(CH_2)_2C(O)NH_2$ | $-C(O)NH_2$ |
| DAY | $-(CH_2)_2C(O)N(CH_3)_2$ | $-C(O)NH_2$ |
| DAZ | $-C(O)(CH_2)_2NHSO_2CH_3$ | $-C(O)NH_2$ |
| DBA | $-CH_2CO_2CH_3$ | $-C(O)NH_2$ |
| DBB | $-CH_2CO_2CH_2CH_3$ | $-C(O)NH_2$ |
| DBC | $-(CH_2)_2CO_2CH_3$ | $-C(O)NH_2$ |
| DBD | $-(CH_2)_2CO_2CH_2CH_3$ | $-C(O)NH_2$ |
| DBE | $-(CH_2)_3CO_2CH_3$ | $-C(O)NH_2$ |
| DBF | $-(CH_2)_3CO_2CH_2CH_3$ | $-C(O)NH_2$ |
| DBG | $-(CH_2)_4CO_2CH_3$ | $-C(O)NH_2$ |
| DBH | $-(CH_2)_4CO_2CH_2CH_3$ | $-C(O)NH_2$ |
| DBI | $-CH_2SO_2NH_2$ | $-C(O)NH_2$ |
| DBJ | $-CH_2SO_2N(CH_3)_2$ | $-C(O)NH_2$ |
| DBK | $-(CH_2)_2NHSO_2H$ | $-C(O)NH_2$ |
| DBL | $-(CH_2)_2NHSO_2CH_3$ | $-C(O)NH_2$ |
| DBM | $-H$ | $-CO_2CH_3$ |
| DBN | $-CH_2C(O)NH_2$ | $-CO_2CH_3$ |
| DBO | $-CH_2C(O)N(CH_3)_2$ | $-CO_2CH_3$ |
| DBP | $-CH_2NHSO_2CH_3$ | $-CO_2CH_3$ |
| DBQ | $-(CH_2)_2C(O)NH_2$ | $-CO_2CH_3$ |
| DBR | $-(CH_2)_2C(O)N(CH_3)_2$ | $-CO_2CH_3$ |
| DBS | $-(CH_2)_2NHSO_2CH_3$ | $-CO_2CH_3$ |
| DBT | $-CH_2CO_2CH_3$ | $-CO_2CH_3$ |
| DBU | $-CH_2CO_2CH_2CH_3$ | $-CO_2CH_3$ |
| DBV | $-(CH_2)_2CO_2CH_3$ | $-CO_2CH_3$ |
| DBW | $-(CH_2)_2CO_2CH_2CH_3$ | $-CO_2CH_3$ |
| DBX | $-(CH_2)_3CO_2CH_3$ | $-CO_2CH_3$ |
| DBY | $-(CH_2)_3CO_2CH_2CH_3$ | $-CO_2CH_3$ |
| DBZ | $-(CH_2)_4CO_2CH_3$ | $-CO_2CH_3$ |
| DCA | $-(CH_2)_4CO_2CH_2CH_3$ | $-CO_2CH_3$ |
| DCB | $-CH_2SO_2NH_2$ | $-CO_2CH_3$ |
| DCC | $-CH_2SO_2N(CH_3)_2$ | $-CO_2CH_3$ |
| DCD | $-(CH_2)_2NHSO_2H$ | $-CO_2CH_3$ |
| DCE | $-(CH_2)_2NHSO_2CH_3$ | $-CO_2CH_3$ |
| DCF | $-H$ | $-CHO$ |
| DCG | $-CH_2C(O)NH_2$ | $-CHO$ |
| DCH | $-CH_2C(O)N(CH_3)_2$ | $-CHO$ |
| DCI | $-C(O)CH_2NHSO_2CH_3$ | $-CHO$ |
| DCJ | $-(CH_2)_2C(O)NH_2$ | $-CHO$ |
| DCK | $-(CH_2)_2C(O)N(CH_3)_2$ | $-CHO$ |
| DCL | $-C(O)(CH_2)_2NHSO_2CH_3$ | $-CHO$ |
| DCM | $-CH_2CO_2CH_3$ | $-CHO$ |
| DCN | $-CH_2CO_2CH_2CH_3$ | $-CHO$ |
| DCO | $-(CH_2)_2CO_2CH_3$ | $-CHO$ |
| DCP | $-(CH_2)_2CO_2CH_2CH_3$ | $-CHO$ |
| DCQ | $-(CH_2)_3CO_2CH_3$ | $-CHO$ |
| DCR | $-(CH_2)_3CO_2CH_2CH_3$ | $-CHO$ |
| DCS | $-(CH_2)_4CO_2CH_3$ | $-CHO$ |
| DCT | $-(CH_2)_4CO_2CH_2CH_3$ | $-CHO$ |
| DCU | $-CH_2SO_2NH_2$ | $-CHO$ |
| DCV | $-CH_2SO_2N(CH_3)_2$ | $-CHO$ |
| DCW | $-(CH_2)_2NHSO_2H$ | $-CHO$ |
| DCX | $-(CH_2)_2NHSO_2CH_3$ | $-CHO$ |
| DCY | $-H$ | $-CN$ |
| DCZ | $-CH_2C(O)NH_2$ | $-CN$ |
| DDA | $-CH_2C(O)N(CH_3)_2$ | $-CN$ |
| DDB | $-C(O)CH_2NHSO_2CH_3$ | $-CN$ |
| DDC | $-(CH_2)_2C(O)NH_2$ | $-CN$ |
| DDD | $-(CH_2)_2C(O)N(CH_3)_2$ | $-CN$ |
| DDE | $-C(O)(CH_2)_2NHSO_2CH_3$ | $-CN$ |
| DDF | $-CH_2CO_2CH_3$ | $-CN$ |
| DDG | $-CH_2CO_2CH_2CH_3$ | $-CN$ |
| DDH | $-(CH_2)_2CO_2CH_3$ | $-CN$ |
| DDI | $-(CH_2)_2CO_2CH_2CH_3$ | $-CN$ |
| DDJ | $-(CH_2)_3CO_2CH_3$ | $-CN$ |
| DDK | $-(CH_2)_3CO_2CH_2CH_3$ | $-CN$ |
| DDL | $-(CH_2)_4CO_2CH_3$ | $-CN$ |

| Compound No.: | G: | R₁: |
|---|---|---|
| DDM | —(CH₂)₄CO₂CH₂CH₃ | —CN |
| DDN | —CH₂SO₂NH₂ | —CN |
| DDO | —CH₂SO₂N(CH₃)₂ | —CN |
| DDP | —(CH₂)₂NHSO₂H | —CN |
| DDQ | —(CH₂)₂NHSO₂CH₃ | —CN |
| DDR | —H | —CH₃ |
| DDS | —CH₂C(O)NH₂ | —CH₃ |
| DDT | —CH₂C(O)N(CH₃)₂ | —CH₃ |
| DDU | —C(O)CH₂NHSO₂CH₃ | —CH₃ |
| DDV | —(CH₂)₂C(O)NH₂ | —CH₃ |
| DDW | —(CH₂)₂C(O)N(CH₃)₂ | —CH₃ |
| DDX | —C(O)(CH₂)₂NHSO₂CH₃ | —CH₃ |
| DDY | —CH₂CO₂CH₃ | —CH₃ |
| DDZ | —CH₂CO₂CH₂CH₃ | —CH₃ |
| DEA | —(CH₂)₂CO₂CH₃ | —CH₃ |
| DEB | —(CH₂)₂CO₂CH₂CH₃ | —CH₃ |
| DEC | —(CH₂)₃CO₂CH₃ | —CH₃ |
| DED | —(CH₂)₃CO₂CH₂CH₃ | —CH₃ |
| DEE | —(CH₂)₄CO₂CH₃ | —CH₃ |
| DEF | —(CH₂)₄CO₂CH₂CH₃ | —CH₃ |
| DEG | —CH₂SO₂NH₂ | —CH₃ |
| DEH | —CH₂SO₂N(CH₃)₂ | —CH₃ |
| DEI | —(CH₂)₂NHSO₂H | —CH₃ |
| DEJ | —(CH₂)₂NHSO₂CH₃ | —CH₃ |
| DEK | —H | —C(O)NH(CH₃) |
| DEL | —CH₂C(O)NH₂ | —C(O)NH(CH₃) |
| DEM | —CH₂C(O)N(CH₃)₂ | —C(O)NH(CH₃) |
| DEN | —C(O)CH₂NHSO₂CH₃ | —C(O)NH(CH₃) |
| DEO | —(CH₂)₂C(O)NH₂ | —C(O)NH(CH₃) |
| DEP | —(CH₂)₂C(O)N(CH₃)₂ | —C(O)NH(CH₃) |
| DEQ | —C(O)(CH₂)₂NHSO₂CH₃ | —C(O)NH(CH₃) |
| DER | —CH₂CO₂CH₃ | —C(O)NH(CH₃) |
| DES | —CH₂CO₂CH₂CH₃ | —C(O)NH(CH₃) |
| DET | —(CH₂)₂CO₂CH₃ | —C(O)NH(CH₃) |
| DEU | —(CH₂)₂CO₂CH₂CH₃ | —C(O)NH(CH₃) |
| DEV | —(CH₂)₃CO₂CH₃ | —C(O)NH(CH₃) |
| DEW | —(CH₂)₃CO₂CH₂CH₃ | —C(O)NH(CH₃) |
| DEX | —(CH₂)₄CO₂CH₃ | —C(O)NH(CH₃) |
| DEY | —(CH₂)₄CO₂CH₂CH₃ | —C(O)NH(CH₃) |
| DEZ | —CH₂SO₂NH₂ | —C(O)NH(CH₃) |
| DFA | —CH₂SO₂N(CH₃)₂ | —C(O)NH(CH₃) |
| DFB | —(CH₂)₂NHSO₂H | —C(O)NH(CH₃) |
| DFC | —(CH₂)₂NHSO₂CH₃ | —C(O)NH(CH₃) |
| DFD | —H | —C(O)N(CH₃)₂ |
| DFE | —CH₂C(O)NH₂ | —C(O)N(CH₃)₂ |
| DFF | —CH₂C(O)N(CH₃)₂ | —C(O)N(CH₃)₂ |
| DFG | —C(O)CH₂NHSO₂CH₃ | —C(O)N(CH₃)₂ |
| DFH | —(CH₂)₂C(O)NH₂ | —C(O)N(CH₃)₂ |
| DFI | —(CH₂)₂C(O)N(CH₃)₂ | —C(O)N(CH₃)₂ |
| DFJ | —C(O)(CH₂)₂NHSO₂CH₃ | —C(O)N(CH₃)₂ |
| DFK | —CH₂CO₂CH₃ | —C(O)N(CH₃)₂ |
| DFL | —CH₂CO₂CH₂CH₃ | —C(O)N(CH₃)₂ |
| DFM | —(CH₂)₂CO₂CH₃ | —C(O)N(CH₃)₂ |
| DFN | —(CH₂)₂CO₂CH₂CH₃ | —C(O)N(CH₃)₂ |
| DFO | —(CH₂)₃CO₂CH₃ | —C(O)N(CH₃)₂ |
| DFP | —(CH₂)₃CO₂CH₂CH₃ | —C(O)N(CH₃)₂ |
| DFQ | —(CH₂)₄CO₂CH₃ | —C(O)N(CH₃)₂ |
| DFR | —(CH₂)₄CO₂CH₂CH₃ | —C(O)N(CH₃)₂ |
| DFS | —CH₂SO₂NH₂ | —C(O)N(CH₃)₂ |
| DFT | —CH₂SO₂N(CH₃)₂ | —C(O)N(CH₃)₂ |
| DFU | —(CH₂)₂NHSO₂H | —C(O)N(CH₃)₂ |
| DFV | —(CH₂)₂NHSO₂CH₃ | —C(O)N(CH₃)₂ |
| DFW | —H | 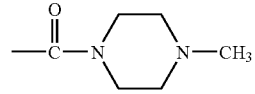 |
| DFX | —CH₂C(O)NH₂ | 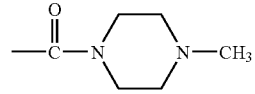 |

-continued

| Compound No.: | G: | R₁: |
|---|---|---|
| DFY | —CH₂C(O)N(CH₃)₂ | —C(O)-N(piperazine)N-CH₃ |
| DFZ | —C(O)CH₂NHSO₂CH₃ | —C(O)-N(piperazine)N-CH₃ |
| DGA | —(CH₂)₂C(O)NH₂ | —C(O)-N(piperazine)N-CH₃ |
| DGB | —(CH₂)₂C(O)N(CH₃)₂ | —C(O)-N(piperazine)N-CH₃ |
| DGC | —C(O)(CH₂)₂NHSO₂CH₃ | —C(O)-N(piperazine)N-CH₃ |
| DGD | —CH₂CO₂CH₃ | —C(O)-N(piperazine)N-CH₃ |
| DGE | —CH₂CO₂CH₂CH₃ | —C(O)-N(piperazine)N-CH₃ |
| DGF | —(CH₂)₂CO₂CH₃ | —C(O)-N(piperazine)N-CH₃ |
| DGG | —(CH₂)₂CO₂CH₂CH₃ | —C(O)-N(piperazine)N-CH₃ |
| DGH | —(CH₂)₃CO₂CH₃ | —C(O)-N(piperazine)N-CH₃ |
| DGI | —(CH₂)₃CO₂CH₂CH₃ | —C(O)-N(piperazine)N-CH₃ |
| DGJ | —(CH₂)₄CO₂CH₃ | —C(O)-N(piperazine)N-CH₃ |
| DGK | —(CH₂)₄CO₂CH₂CH₃ | —C(O)-N(piperazine)N-CH₃ |
| DGL | —CH₂SO₂NH₂ | —C(O)-N(piperazine)N-CH₃ |

-continued
| Compound No.: | G: | R₁: |
|---|---|---|
| DGM | —CH₂SO₂N(CH₃)₂ | 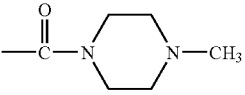 |
| DGN | —(CH₂)₂NHSO₂H | 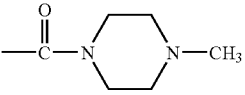 |
| DGO | —(CH₂)₂NHSO₂CH₃ | 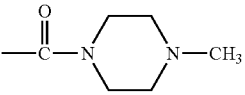 |
| DGP | —H | 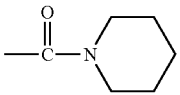 |
| DGQ | —CH₂C(O)NH₂ | 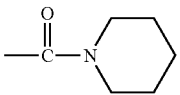 |
| DGR | —CH₂C(O)N(CH₃)₂ | 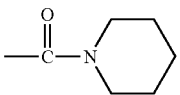 |
| DGS | —C(O)CH₂NHSO₂CH₃ | 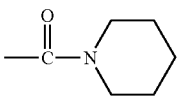 |
| DGT | —(CH₂)₂C(O)NH₂ | 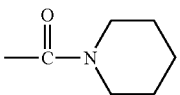 |
| DGU | —(CH₂)₂C(O)N(CH₃)₂ | 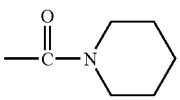 |
| DGV | —C(O)(CH₂)₂NHSO₂CH₃ | 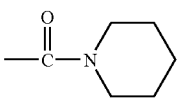 |
| DGW | —CH₂CO₂CH₃ | 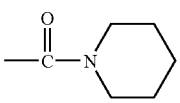 |
| DGX | —CH₂CO₂CH₂CH₃ | 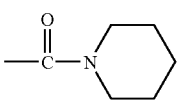 |
| DGY | —(CH₂)₂CO₂CH₃ | 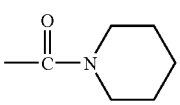 |
| DGZ | —(CH₂)₂CO₂CH₂CH₃ | 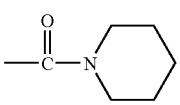 |

-continued

| Compound No.: | G: | R₁: |
|---|---|---|
| DHA | —(CH₂)₃CO₂CH₃ | —C(O)—N(piperidine) |
| DHB | —(CH₂)₃CO₂CH₂CH₃ | —C(O)—N(piperidine) |
| DHC | —(CH₂)₄CO₂CH₃ | —C(O)—N(piperidine) |
| DHD | —(CH₂)₄CO₂CH₂CH₃ | —C(O)—N(piperidine) |
| DHE | —CH₂SO₂NH₂ | —C(O)—N(piperidine) |
| DHF | —CH₂SO₂N(CH₃)₂ | —C(O)—N(piperidine) |
| DHG | —(CH₂)₂NHSO₂H | —C(O)—N(piperidine) |
| DHH | —(CH₂)₂NHSO₂CH₃ | —C(O)—N(piperidine) |
| DHI | —H | —C(O)—N(pyrrole) |
| DHJ | —CH₂C(O)NH₂ | —C(O)—N(pyrrole) |
| DHK | —CH₂C(O)N(CH₃)₂ | —C(O)—N(pyrrole) |
| DHL | —C(O)CH₂NHSO₂CH₃ | —C(O)—N(pyrrole) |
| DHM | —(CH₂)₂C(O)NH₂ | —C(O)—N(pyrrole) |
| DHN | —(CH₂)₂C(O)N(CH₃)₂ | —C(O)—N(pyrrole) |

-continued

| Compound No.: | G: | R₁: |
|---|---|---|
| DHO | —C(O)(CH₂)₂NHSO₂CH₃ | —C(O)-N-pyrrole |
| DHP | —CH₂CO₂CH₃ | —C(O)-N-pyrrole |
| DHQ | —CH₂CO₂CH₂CH₃ | —C(O)-N-pyrrole |
| DHR | —(CH₂)₂CO₂CH₃ | —C(O)-N-pyrrole |
| DHS | —(CH₂)₂CO₂CH₂CH₃ | —C(O)-N-pyrrole |
| DHT | —(CH₂)₃CO₂CH₃ | —C(O)-N-pyrrole |
| DHU | —(CH₂)₃CO₂CH₂CH₃ | —C(O)-N-pyrrole |
| DHV | —(CH₂)₄CO₂CH₃ | —C(O)-N-pyrrole |
| DHW | —(CH₂)₄CO₂CH₂CH₃ | —C(O)-N-pyrrole |
| DHX | —CH₂SO₂NH₂ | —C(O)-N-pyrrole |
| DHY | —CH₂SO₂N(CH₃)₂ | —C(O)-N-pyrrole |
| DHZ | —(CH₂)₂NHSO₂H | —C(O)-N-pyrrole |
| DIA | —(CH₂)₂NHSO₂CH₃ | —C(O)-N-pyrrole |
| DIB | —H | —C(O)-N-morpholine |

-continued
| Compound No.: | G: | R₁: |
|---|---|---|
| DIC | —CH$_2$C(O)NH$_2$ | 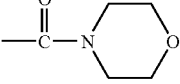 |
| DID | —CH$_2$C(O)N(CH$_3$)$_2$ | 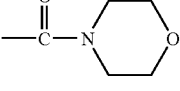 |
| DIE | —C(O)CH$_2$NHSO$_2$CH$_3$ | 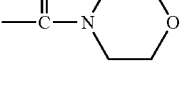 |
| DIF | —(CH$_2$)$_2$C(O)NH$_2$ | 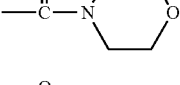 |
| DIG | —(CH$_2$)$_2$C(O)N(CH$_3$)$_2$ | 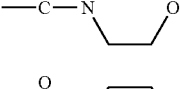 |
| DIH | —C(O)(CH$_2$)$_2$NHSO$_2$CH$_3$ | 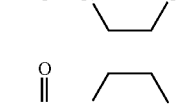 |
| DII | —CH$_2$CO$_2$CH$_3$ | 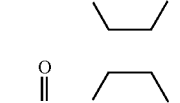 |
| DIJ | —CH$_2$CO$_2$CH$_2$CH$_3$ | 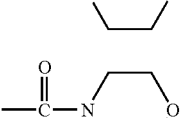 |
| DIK | —(CH$_2$)$_2$CO$_2$CH$_3$ | 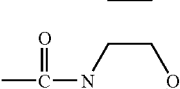 |
| DIL | —(CH$_2$)$_2$CO$_2$CH$_2$CH$_3$ | 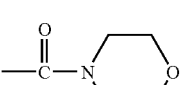 |
| DIM | —(CH$_2$)$_3$CO$_2$CH$_3$ | 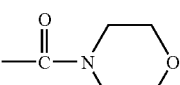 |
| DIN | —(CH$_2$)$_3$CO$_2$CH$_2$CH$_3$ | 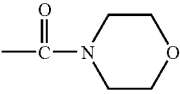 |
| DIO | —(CH$_2$)$_4$CO$_2$CH$_3$ | 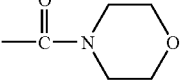 |
| DIP | —(CH$_2$)$_4$CO$_2$CH$_2$CH$_3$ |  |

| Compound No.: | G: | $R_1$: |
|---|---|---|
| DIQ | —$CH_2SO_2NH_2$ | —C(O)—N(morpholinyl) |
| DIR | —$CH_2SO_2N(CH_3)_2$ | —C(O)—N(morpholinyl) |
| DIS | —$(CH_2)_2NHSO_2H$ | —C(O)—N(morpholinyl) |
| DIT | —$(CH_2)_2NHSO_2CH_3$ | —C(O)—N(morpholinyl) |
| DIU | —$(CH_2)_3NHSO_2H$ | —H |
| DIV | —$(CH_2)_3NHSO_2H$ | —C(O)$NH_2$ |
| DIW | —$(CH_2)_3NHSO_2H$ | —$CO_2CH_3$ |
| DIX | —$(CH_2)_3NHSO_2H$ | —CHO |
| DIY | —$(CH_2)_3NHSO_2H$ | —CN |
| DIZ | —$(CH_2)_3NHSO_2H$ | —$CH_3$ |
| DJA | —$(CH_2)_3NHSO_2H$ | —C(O)$NHCH_3$ |
| DJB | —$(CH_2)_3NHSO_2H$ | —C(O)$N(CH_3)_2$ |
| DJC | —$(CH_2)_3NHSO_2H$ | —C(O)—N(4-methylpiperazinyl)—$CH_3$ |
| DJD | —$(CH_2)_3NHSO_2H$ | —C(O)—N(piperidinyl) |
| DJE | —$(CH_2)_3NHSO_2H$ | —C(O)—N(pyrrolyl) |
| DJF | —$(CH_2)_3NHSO_2H$ | —C(O)—N(morpholinyl) |

4.3 Methods for Making the 4-Tetrazolyl 4 Phenylpiperidine Compounds

The 4-Tetrazolyl-4-phenylpiperidine Compounds of the present invention can be made using conventional organic syntheses and by the following illustrative methods:

Scheme 1 depicts methods for making 4-Tetrazolyl-4-phenylpiperidine Compounds where $R_1$ is —C(O)$NZ_2$, where each Z is a —($C_1$-$C_4$ alkyl) group or both Z groups and the nitrogen atom to which they are attached are taken together to form N-(4-$R_4$)—N'-1-piperazinyl, aziridyl, azetidyl, pyrrolidyl, piperidyl, homopiperidyl, pyrrolyl or morpholinyl. Bromoacids 1 are converted to bromoacid chlorides 2 using thionylchloride (J. S. Pizey, *Synthetic Reactions* 2: 65 (1974)). Bromoacid chlorides 2 are reacted with $Z_2NH$, optionally in the presence of base such as $Na_2CO_3$, to provide reactive intermediates 3, which are treated with 4-cyano-4-phenylpiperidines 4 (Scheme 10) to provide cyanophenyl compounds 5. Cyanophenyl compounds 5 are treated with $Me_3SnN_3$ or $Me_3SiN_3$ and tin oxide (S. J. Wittenberg et al., *J. Org. Chem.* 58:4134-4141 (1993)) to provide 4-Tetrazolyl-4-phenylpiperide Compounds 6, wherein $R_1$ is —C(O)$NZ_2$ and G is —H, Compounds 6 are reacted with $G_1$-X, wherein $G_1$ is all G, defined above, except hydrogen, and X is a leaving group such as halogen, trifluoromethane sulfonate, methanesulfonate or tolunesulfonate, to provide a mixture of 4-Tetrazolyl-4-phenylpiperidine Compounds 7 and 8. Compounds 7 and 8 are separable using conventional means, such as silica gel chromatography, high-performance liquid chromatography or recrystallization. Compounds of the formula $G_1$-X can be obtained commercially or made using conventional organic synthesis methods.

Scheme 1

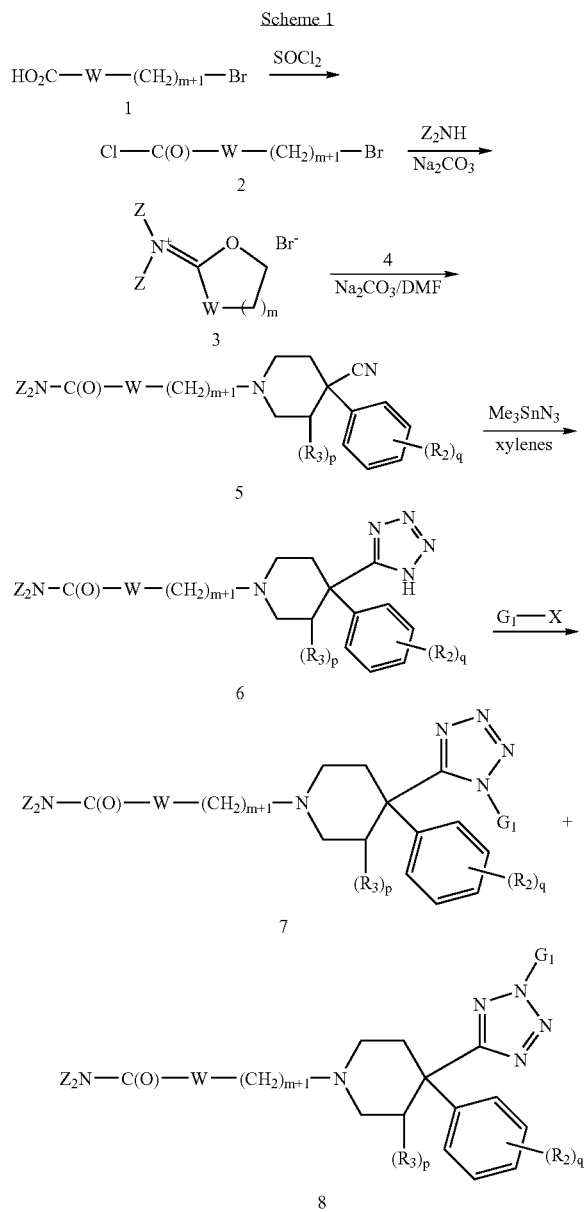

m, p, q, $R_2$ and $R_3$ are as defined above and —W— is —$C(Ar_1)(Ar_2)$— or —$C(H)(Ar_3)$—.

Scheme 2 depicts methods for making 4-Tetrazolyl-4-phenylpiperidine Compounds where $R_1$ is —$CO_2R_4$. Bromoacid chlorides 2 (Scheme 1) are reacted with $R_4OH$, optionally in the presence of a base such as pyridine, 4-dimethylaminopyridine, triethylamine or Hünig's base, to provide bromoesters 9. Bromoesters 9 are reacted with 4-cyano-4-phenylpiperidines 4 (Scheme 10) to provide cyanophenyl compounds 10, which are treated with $Me_3SnN_3$ or $Me_3SiN_3$ and tin oxide (S. J. Wittenberg et al., J. Org. Chem. 58:4139-4141 (1993)) to provide 4-Tetrazolyl-4-phenylpiperidine Compounds 11, where $R_1$ is $R_4OC(O)$— and G is —H, Compounds 11 are reacted with $G_1X$, wherein $G_1$ and X are as defined above, to provide a mixture of 4-Tetrazolyl-4-phenylpiperidine Compounds 12 and 13, Compounds 12 and 13 are separable using conventional means described above.

Scheme 2

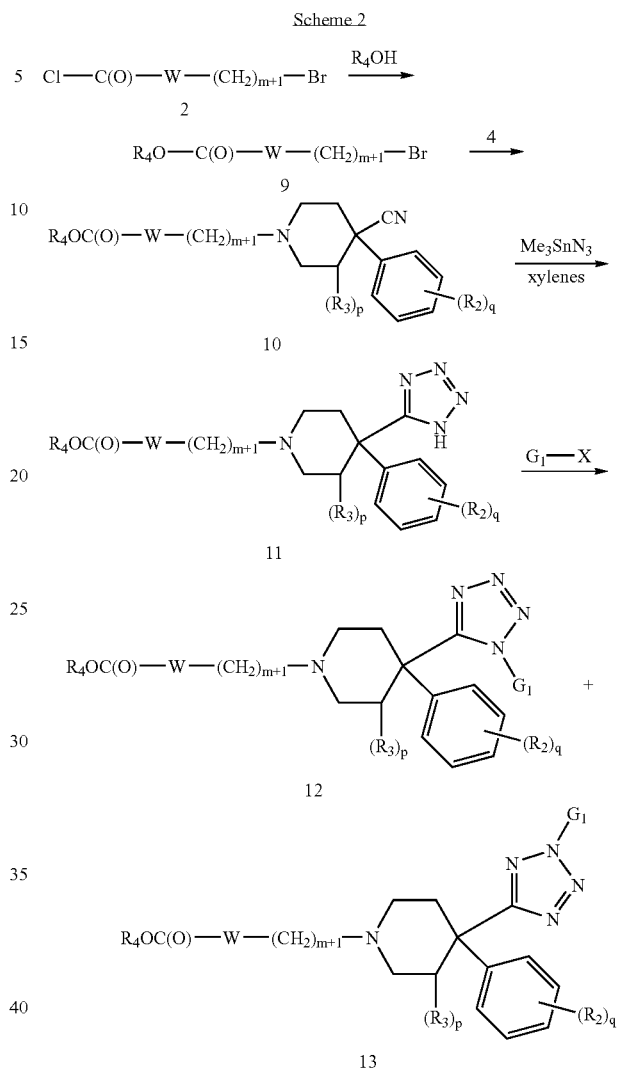

m, p, q, $R_2$ and $R_3$ are as defined above and —W— is —$C(Ar_1)(Ar_2)$— or —$C(H)(Ar_3)$—.

Scheme 3 depicts methods for making 4-Tetrazolyl-4-phenylpiperidine Compounds where $R_1$ is —$C(O)NH(C_1-C_4$ alkyl). Compounds 11 (Scheme 2) are protected with a base-stable protecting group such as a mesitylenesulfonamide; cyclohexylcarbamate; 1,1-dimethyl-2,2,2-trichloroethylcarbamate; N-(1-ethoxy)ethyl group; or a similar protecting group (See T. W. Greene et al., Protective Groups in Organic Synthesis 615-631 (1999)) to provide protected compounds 14. Compounds 14 are hydrolyzed using hydroxide base, optionally in the presence of methanol, to provide after work up acids 15, which are amidated using $(C_1-C_4)NH_2$ to provide protected compounds 16. Compounds 16 are deprotected using a strong acid (Greene at 615-631) to provide 4-Tetrazolyl-4-phenylpiperidine Compounds 17 where $R_1$ is —$C(O)NH(C_1-C_4$ alkyl) and G is —H, Compounds 17 are reacted with $G_1$-X, wherein $G_1$ and X are as defined above, to provide a mixture of 4-Tetrazolyl-4-phenylpiperidine Compounds 18 and 19. Compounds 18 and 19 are separable using conventional means described above.

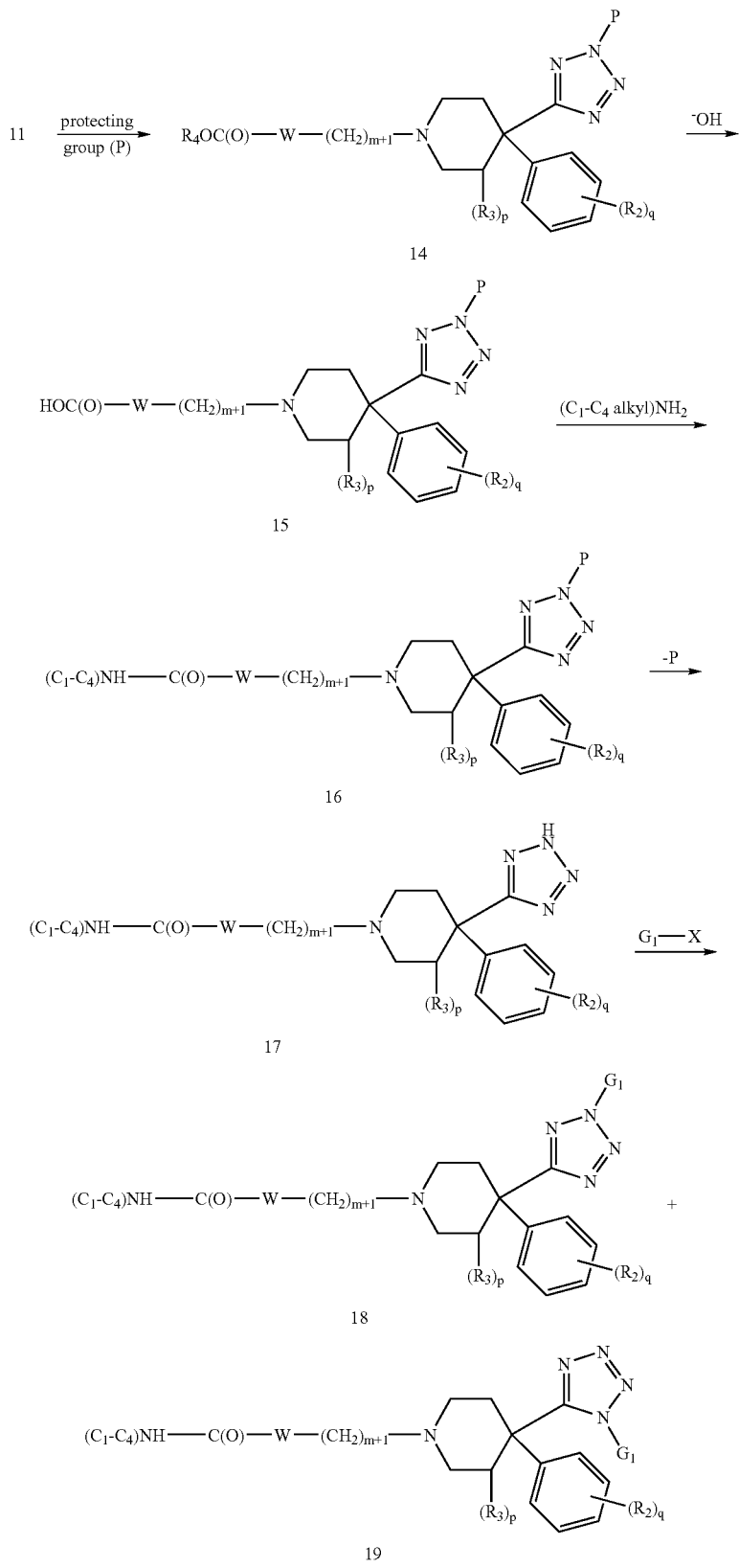

m, p, q, $R_2$ and $R_3$ are as defined above and —W— is —C($Ar_1$)($Ar_2$)— or —C(H)($Ar_3$)—.

Scheme 4 depicts methods for making 4-Tetrazolyl-4-phenylpiperidine Compounds where $R_1$ is —C(O)NHOH. Acids 15 (Scheme 3) are treated with $NH_2OH$ to provide protected compounds 20, which are deprotected using strong acid (Greene at 615-631) to provide 4-Tetrazolyl-4-phenylpiperidine Compounds 21 where $R_1$ is —C(O)NHOH and G is —H. Compounds 21 are reacted with $G_1$-X, wherein $G_1$ and X are as defined above, to provide a mixture of 4-Tetrazolyl-4-phenylpiperidine Compounds 22 and 23. Compounds 22 and 23 are separable using conventional means described above.

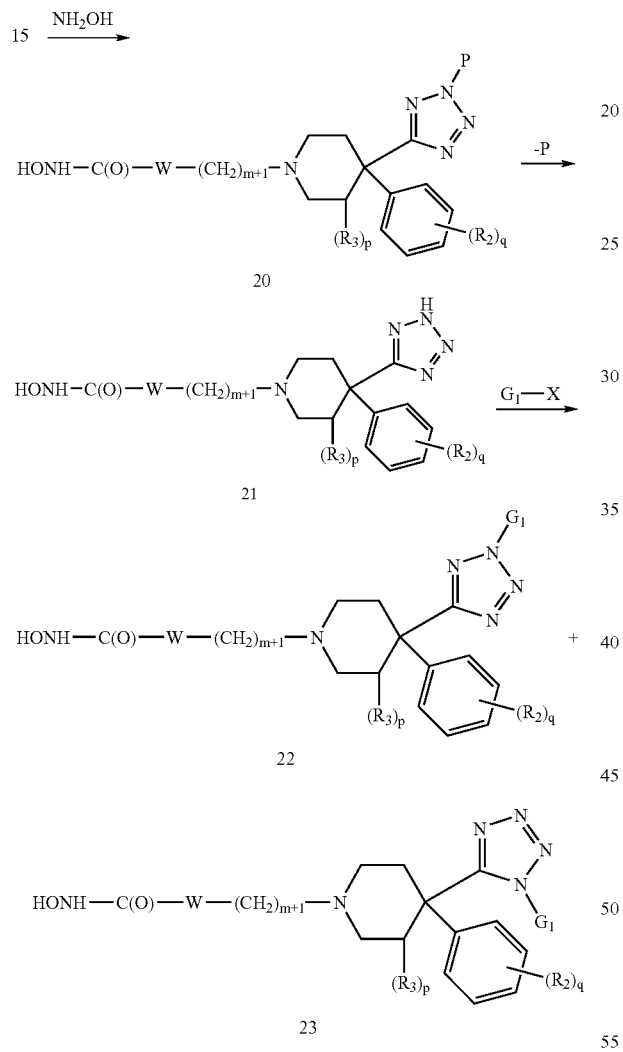

m, p, q, $R_2$ and $R_3$ are as defined above and —W— is —C($Ar_1$)($Ar_2$)— or —C(H)($Ar_3$)—.

Scheme 5 depicts methods for making 4-Tetrazolyl-4-phenylpiperidine Compounds where $R_1$ is —H. Bromides 24 are treated with 4-cyano-4-phenylpiperidines 4 to provide cyanophenyl intermediates 25, which are reacted with $Me_3SnN_3$ or $Me_3SiN_3$ and tin oxide (S. J. Wittenberg et al., *J. Org. Chem.* 58:4139-4141 (1993)) to provide 4-tetrazolyl-4-phenylpiperidine Compounds 26 where $R_1$ and -G are —H, Compounds 26 are reacted with $G_1$-X, wherein $G_1$ and X are as defined above, to provide a mixture of 4-Tetrazolyl-4-phenylpiperidine Compounds 27 and 28. Compounds 27 and 28 are separable using conventional means described above.

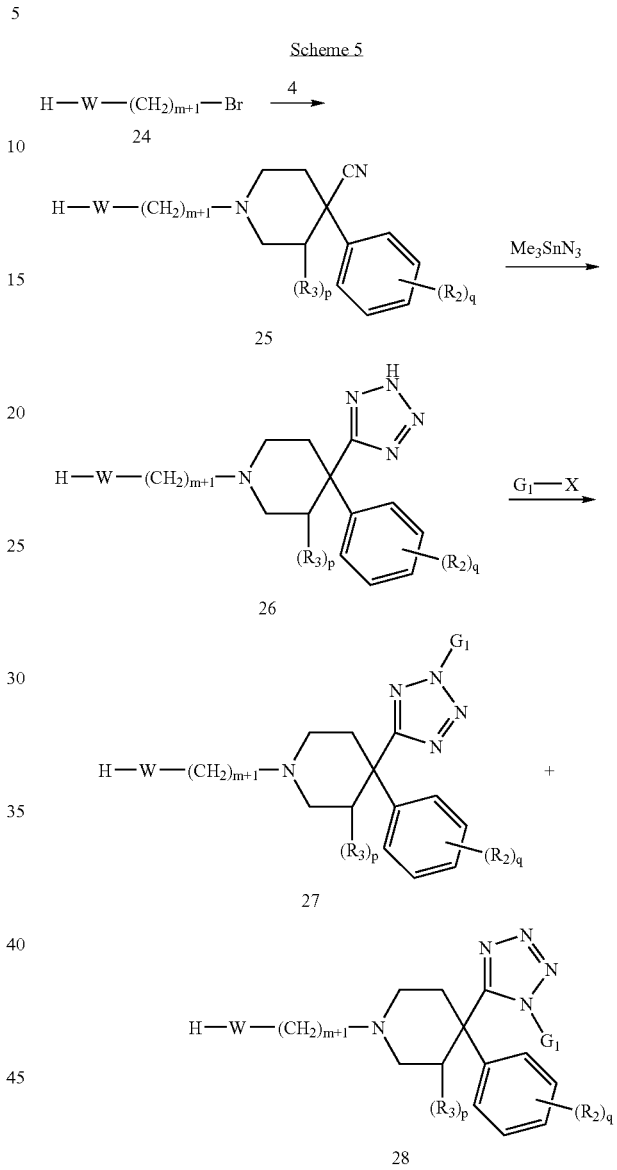

m, p, q, $R_2$ and $R_3$ are as defined above and —W— is —C($Ar_1$)($Ar_2$)— or —C(H)($Ar_3$)—.

Scheme 6 depicts methods for making 4-Tetrazolyl-4-phenylpiperidine Compounds where $R_1$ is —CHO. 4-Tetrazolyl-4-phenylpiperidine Compounds 27 (Scheme 5) are treated with a strong base such as $NaNH_2$ and quenched with dimethylformamide (see U. T. Mueller-Westerhoff et al., *Synlett* 975 (1994)) to provide after work up protected aldehydes 28. Protected aldehydes 28 are deprotected (Greene at 615-631) to provide 4-Tetrazolyl-4-phenylpiperidine Compounds 29 where $R_1$— is —CHO and -G is —H, Compounds 29 are reacted with $G_1$-X, wherein $G_1$ and X are as defined above, to provide a mixture of 4-Tetrazolyl-4-phenylpiperidine Compounds 30 and 31, which are separable using conventional means described above.

Scheme 6

27 $\xrightarrow{\text{NaNH}_2}{\text{DMF}}$

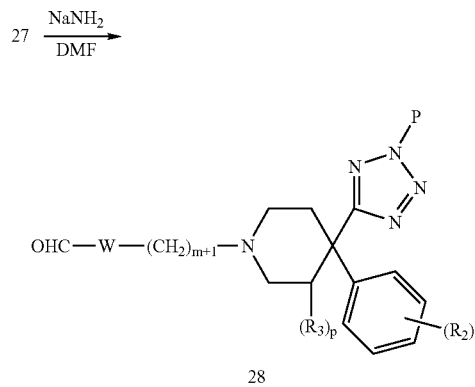

28

↓ -P

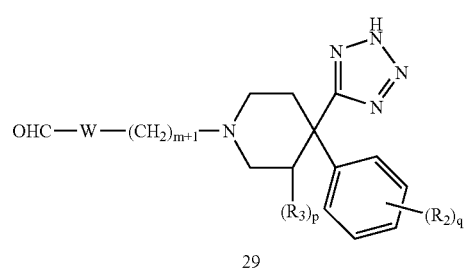

29

↓ G₁—X

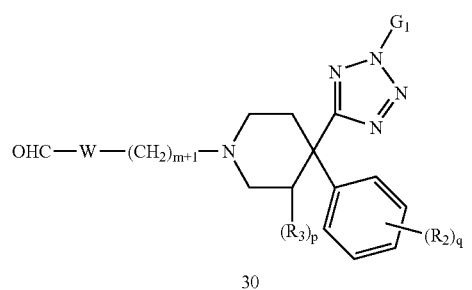

30

+

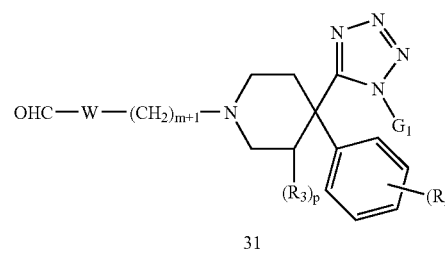

31

Scheme 7

27 $\xrightarrow{\text{NaNH}_2}{(C_1\text{-}C_4\text{ alkyl})\text{-}X}$

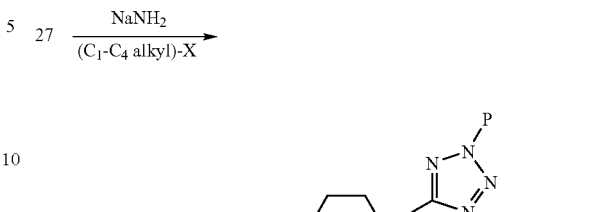

32

↓ -P

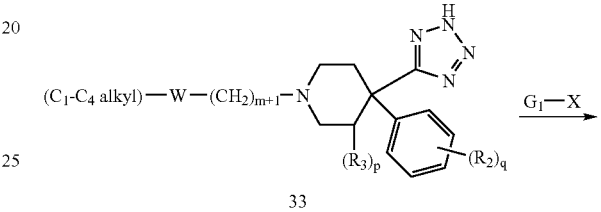

33

↓ G₁—X

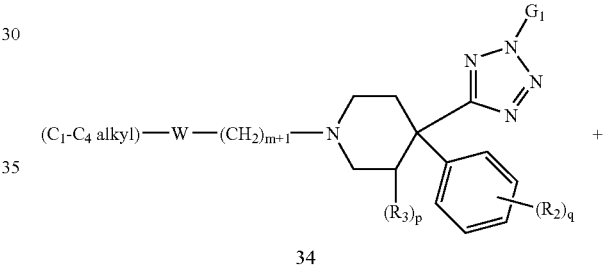

34

+

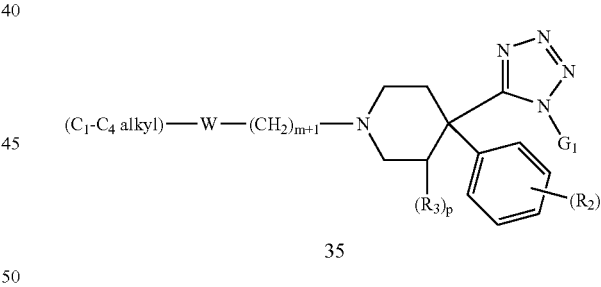

35 m, p, q, R₂ and R₃ are as defined above and —W— is —C(Ar₁)(Ar₂)— or —C(H)(Ar₃)—.

Scheme 7 depicts methods for making 4-Tetrazolyl-4-phenylpiperidine Compounds where R₁ is —(C₁-C₄ alkyl). Compounds 27 (Scheme 5) are treated with a strong base such as NaNH₂ and quenched with (C₁-C₄ alkyl)-X, where X is defined above, to provide protected Compounds 32. Compounds 32 are deprotected (Greene at 615-631) to provide 4-Tetrazolyl-4-phenylpiperdine Compounds 33 where R₁ is —(C₁-C₄ alkyl) and G is H. Compounds 33 are reacted with G₁—X, wherein G₁ and X are as defined above, to provide a mixture of 4-Tetrazolyl-4-phenylpiperidine Compounds 34 and 35, which are separable using conventional means described above.

m, p, q, R₂ and R₃ are as defined above and —W— is —C(Ar₁)(Ar₂)— or —C(H)(Ar₃)—.

Scheme 8 depicts methods for making 4-Tetrazolyl-4-phenylpiperdine Compounds where R₁ is —C(O)NH₂. Protected esters 14 (Scheme 3) are treated with NH₃ (See M. B. Smith et al., *March's Advanced Organic Chemistry: Reactions, Mechanisms, and Structure* 510-511 (2001)) to provide protected amides 36, which are deprotected (Greene at 615-631) to provide 4-Tetrazolyl-4-phenylpiperidine Compounds 37 where R₁ is —C(O)NH₂ and -G is —H. Compound 37 are reacted with G₁-X, wherein G₁ and X are as defined above, to provide a mixture of 4-Tetrazolyl-4-phenylpiperidine Compounds 38 and 39, which are separable using conventional means defined above.

Scheme 8

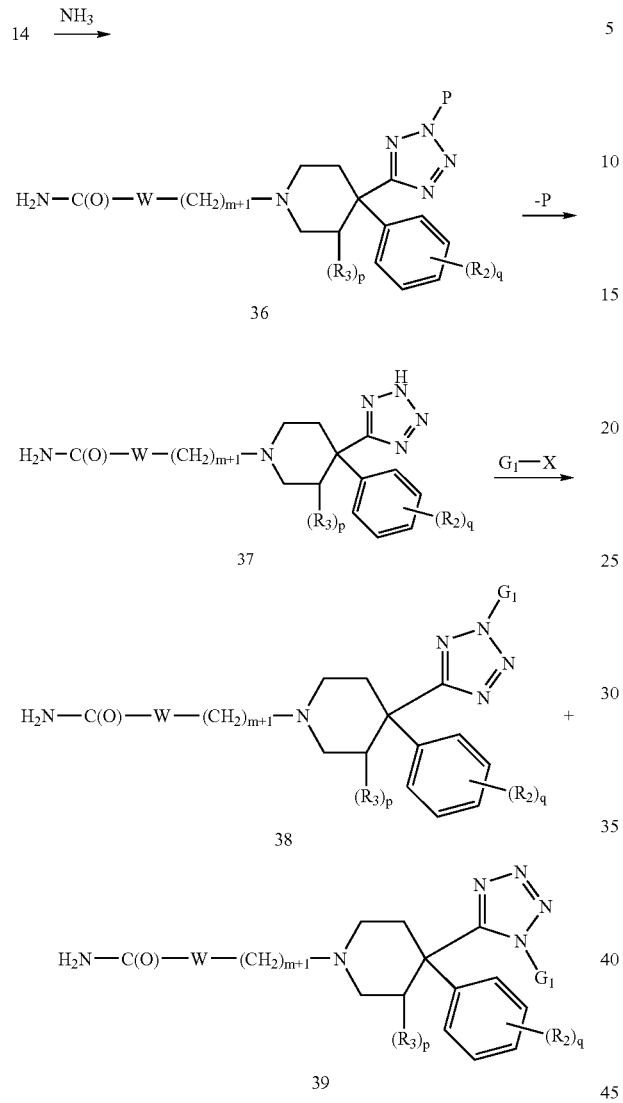

m, p, q, $R_2$ and $R_3$ are as defined above —W— is —C($Ar_1$)($Ar_2$)— or —C(H)($Ar_3$)—.

Scheme 9 depicts methods for making 4-Tetrazolyl-4-phenylpiperidine Compounds wherein $R_1$ is —CN. 4-Tetrazolyl-4-phenylpiperidine Compounds 37 (Scheme 8) are treated with $Ph_3P$ and $CCl_4$ (W. J. Rogers, *Synthesis* 41 (1997)) to provide 4-Tetrazolyl-4-phenylpiperidine Compounds 40 wherein $R_1$ is —CN and G is —H, Compounds 40 are reacted with $G_1$-X, wherein $G_1$ and X are as defined above, to provide a mixture of 4-Tetrazolyl-4-phenylpiperidine Compounds 41 and 42, which are separable using conventional means described above.

Scheme 9

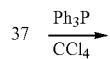

m, p, q, and $R_2$ and $R_3$ are as defined above and —W— is —C($Ar_1$)($Ar_2$)— or —C(H)($Ar_3$)—.

Scheme 10 depicts methods for making 4-cyano-4-phenylpiperidines 4. ($R_3$)p-Substituted aminodiols 43 are N-alkylated using benzyl chloride 44 in $NaHCO_3/H_2O$ to provide N-benzyl diols 45, which are chlorinated using $SOCl_2$ to provide dichlorides 46. Dichlorides 46 are condensed with deprotonated ($NaNH_2$ in toluene) benzyl cyanides 47 to provide benzyl compounds 48, which are debenzylated using $H_2$ and Pd/C (95% EtOH) to provide 4-cyano-4-phenylpiperides 4.

Scheme 10

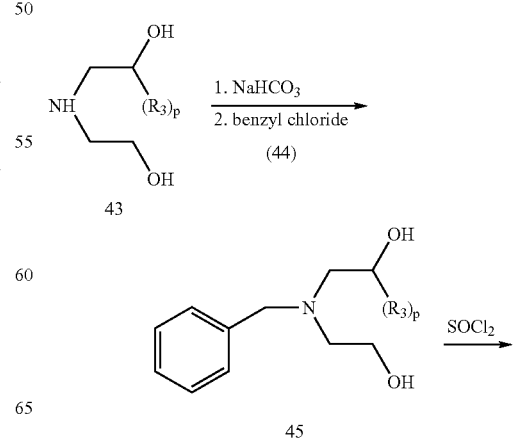

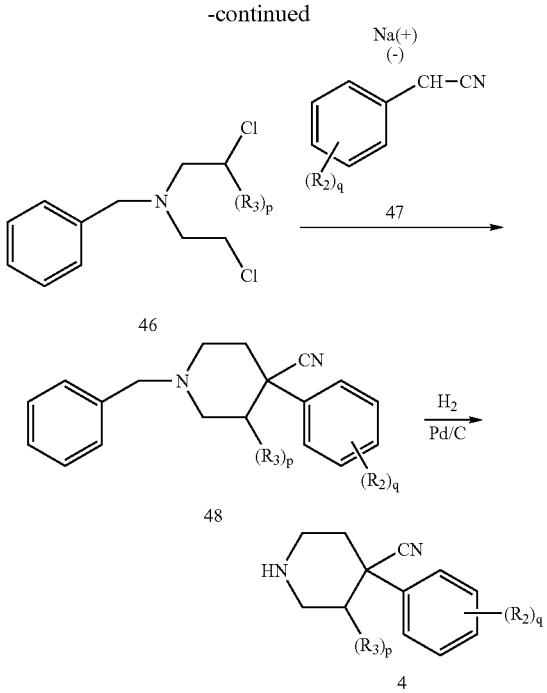

Certain 4-Tetrazolyl-4-phenylpiperidine Compounds can have asymmetric centers and therefore exist in different enantiomeric and diastereomeric forms. A 4-Tetrazolyl-4-phenylpiperidine Compound can be in the form of an optical isomer or a diastereomer. Accordingly, the invention encompasses 4-Tetrazolyl-4-phenylpiperidine Compounds and their uses as described herein in the form of their individual optical isomers, diasteriomers, and mixtures thereof, including a racemic mixture.

In addition, certain 4-Tetrazolyl-4-phenylpiperidine Compounds can exist as tautomers. For example, where G=H, certain 4-Tetrazolyl-4-phenylpiperidine Compounds of Formula I (a) and Formula I (b) (e.g. structures AAT and BAT), and certain 4-Tetrazolyl-4-phenylpiperidine Compounds of Formula I (c) and Formula I (d) (e.g. structures CAT and DAT), are tautomers of each other. Each structure depicted herein is intended to encompass all tautomers thereof, each of which is understood to be included in the present invention, whether specifically disclosed or not, and whether or not the tautomer depicted herein represents a tautomer in excess relative to any other tautomer thereof. Accordingly, the invention also encompasses 4-Tetrazolyl-4-phenylpiperidine Compounds and their uses as described herein in the form of their individual tautomers.

In addition, one or more hydrogen, carbon or other atoms of a 4-Tetrazolyl-4-phenylpiperidine Compound can be replaced by an isotope of the hydrogen, carbon or other atoms. Such compounds, which are encompassed by the present invention, are useful as research and diagnostic tools in metabolism pharmacokinetic studies and in binding assays.

4.4 Therapeutic Uses of the 4-Tetrazolyl-4-phenylpiperidine Compounds

In accordance with the invention, the 4-Tetrazolyl-4-phenylpiperidine Compounds are administered to an animal, in one embodiment a mammal, in another embodiment a human, for the treatment or prevention of pain. The 4-Tetrazolyl-4-phenylpiperidine Compounds can be used to treat or prevent acute or chronic pain. For example, the 4-Tetrazolyl-4-phenylpiperidine Compounds can be used for, but are not limited to, treating or preventing cancer pain, central pain, labor pain, myocardial infarction pain, pancreatic pain, colic pain, post operative pain, headache pain, muscle pain, and pain associated with intensive care.

The 4-Tetrazolyl-4-phenylpiperidine Compounds can also be used for inhibiting, preventing, or treating pain associated with inflammation or with an inflammatory disease in an animal. The pain to be inhibited, treated or prevented may be associated with inflammation associated with an inflammatory disease, which can arise where there is an inflammation of the body tissue, and which can be a local inflammatory response and/or a systemic inflammation. For example, the 4-Tetrazolyl-4-phenylpiperidine Compounds can be used to inhibit, treat, or prevent pain associated with inflammatory diseases including, but not limited to: organ transplant rejection; reoxygenation injury resulting from organ transplantation (see Grupp et al. *J. Mol. Cell. Cardiol.* 31:297 303 (1999)) including, but not limited to, transplantation of the heart, lung, liver, or kidney; chronic inflammatory diseases of the joints, including arthritis, rheumatoid arthritis, osteoarthritis and bone diseases associated with increased bone resorption; inflammatory bowel diseases, such as ileitis, ulcerative colitis, Barrett's syndrome, and Crohn's disease; inflammatory lung diseases, such as asthma, adult respiratory distress syndrome, and chronic obstructive airway disease; inflammatory diseases of the eye, including corneal dystrophy, trachoma, onchocerciasis, uveitis, sympathetic ophthalmitis and endophthalmitis; chronic inflammatory diseases of the gum, including gingivitis and periodontitis; tuberculosis; leprosy; inflammatory diseases of the kidney, including uremic complications, glomerulonephritis and nephrosis; inflammatory diseases of the skin, including sclerodermatitis, psoriasis and eczema; inflammatory diseases of the central nervous system, including chronic demyelinating diseases of the nervous system, multiple sclerosis, AIDS-related neurodegeneration and Alzheimer s disease, infectious meningitis, encephalomyelitis, Parkinson's disease, Huntington's disease, amyotrophic lateral sclerosis, and viral or autoimmune encephalitis; autoimmune diseases, including Type I and Type II diabetes mellitus; diabetic complications, including, but not limited to, diabetic cataract, glaucoma, retinopathy, nephropathy (such as microaluminuria and progressive diabetic nephropathy), polyneuropathy, mononeuropathies, autonomic neuropathy, gangrene of the feet, atherosclerotic coronary arterial disease, peripheral arterial disease, nonketotic hyperglycemic hyperosmolar coma, foot ulcers, joint problems, and a skin or mucous membrane complication (such as an infection, a shin spot, a candidal infection or necrobiosis lipoidica diabeticorum); immune-complex vasculitis, systemic lupus erythematosus (SLE); inflammatory diseases of the heart, such as cardiomyopathy, ischemic heart disease hypercholesterolemia, and atherosclerosis; as well as various other diseases that can have significant inflammatory components, including preeclampsia, chronic liver failure, brain and spinal cord trauma, and cancer. The 4-Tetrazolyl-4-phenylpiperidine Compounds can also be used for inhibiting, treating, or preventing pain associated with inflammatory disease that can, for example, be a systemic inflammation of the body, exemplified by gram-positive or gram negative shock, hemorrhagic or anaphylactic shock, or shock induced by cancer chemotherapy in response to pro-inflammatory cytokines, e.g., shock associated with pro-inflammatory cytokines. Such shock can be induced, e.g., by a chemotherapeutic agent that is adminstered as a treatment for cancer.

In another embodiment, the 4-Tetrazolyl-4-phenylpiperidine Compounds are administered to an animal, in one embodiment a mammal, in another embodiment a human, for the treatment or prevention of diarrhea. The 4-Tetrazolyl-4-phenylpiperidine Compounds can be used to treat or prevent acute or chronic diarrhea. For example, the 4-Tetrazolyl-4-phenylpiperidine Compounds can be used for, but are not limited to, treating or preventing acute diarrhea caused by a virus, such as but not limited to Norwalk-virus, Norwalk-like virus, Rotavirus, and Cytomegaloviurs: protozoa, such as but not limited to *Girardia lamlia, Crpytosporidium* and *Entamoeba histolytica*; and bacteria, including but not limited to *Stapylococcus aureus, Bacillus cereus, Clostridium perfringens*, enterotoxigenic *E. coli, Vibrio cholera*, enterohemmorrhagic *E. coli* O157:H5, *Vibrio parahaemolyticus, Clostridium difficile, Campylobacter jejuni, Salmonella*, enteroinvasive *E. coli, Aeromonas, Plesiomonas, Yersinia enterocolitica, Chlamydia, Nisseria gonorrhoeae*, and *Listeria monocytogenes*. For example, the 4-Tetrazolyl-4-phenylpiperidine Compounds can be used for treating or preventing chronic diarrhea classified as that including, but not limited to, osmotic diarrhea, secretory diarrhea, or resulting from an inflammatory condition, a malabsorption syndrome, a motility disorder, and a chronic infection.

Applicants believe that unlike traditional opioid agonists and nonsteroidal anti-inflammatory agents, the 4-Tetrazolyl-4-phenylpiperidine Compounds do not significantly cross the blood-brain barrier. Accordingly, Applicants believe that the administration of an effective amount of a 4-Tetrazolyl-4-phenylpiperidine Compound to an animal results in fewer side effects, including respiratory depression, unwanted euphoria, sedation, constipation, increased drug tolerance, and increased drug dependence, that can result from the administration of traditional opioid agonists or nonsteroidal anti-inflammatory agents. In one embodiment, the administration of an effective amount of a 4-Tetrazolyl-4-phenylpiperidine Compound to an animal results in none of the aforementioned side effects. Therefore, in certain embodiments, the present methods encompass treating or preventing pain, while reducing or eliminating one or more of the aforementioned side effects.

Without wishing to be bound by theory, it is believed that the 4-Tetrazolyl-4-phenylpiperidine Compounds are agonists for and, accordingly, are capable of stimulating an opioid receptor.

The invention also relates to methods for stimulating opioid-receptor function in a cell comprising contacting a cell capable of expressing an opioid receptor with an effective amount of a 4-Tetrazolyl-4-phenylpiperidine Compound. The method is also useful for stimulating opioid receptor function in a cell in vivo, in an animal, in one embodiment a human, by contacting a cell capable of expressing an opioid receptor, in an animal, with an effective amount of a 4-Tetrazolyl-4-phenylpiperidine Compound. In one embodiment, the method is useful for treating or preventing pain or diarrhea in an animal. Brain tissue, spinal chord tissue, immune cells, cells of the gastrointestinal tract, and primary afferent nerve cells are examples of tissues and/or cells that are capable of expressing an opioid receptor. This method can be used in vitro, for example, as an assay to select cells that express an opioid receptor.

4.4.1 Therapeutic/Prophylactic Administration and Compositions of the Invention Due to their activity, the 4-Tetrazolyl-4-phenylpiperidine Compounds are advantageously useful in veterinary and human medicine. As described above, the 4-Tetrazolyl-4-phenylpiperidine Compounds are useful for treating or preventing pain or diarrhea in an animal in need thereof.

When administered to an animal, the 4-Tetrazolyl-4-phenylpiperidine Compounds can be administered as a component of a pharmaceutical composition that comprises a pharmaceutically acceptable carrier or excipient. The present compositions, which comprise a 4-Tetrazolyl-4-phenylpiperidine Compound, are in one embodiment administered orally. The compositions of the invention can also be administered by any other convenient route, for example, by infusion or bolus injection, by absorption through epithelial or mucocutaneous linings (e.g., oral mucosa, rectal, and intestinal mucosa, etc.) and can be administered together with another therapeutic agent. Administration can be systemic or local. Various delivery systems are known, e.g., encapsulation in liposomes, microparticles, microcapsules, capsules, etc., and can be used to administer the 4-Tetrazolyl-4 phenylpiperidine Compounds.

Methods of administration include but are not limited to intradermal, intramuscular, intraperitoneal, intravenous, subcutaneous, intranasal, epidural, oral, sublingual, intracerebral, intravaginal, transdermal, rectal, by inhalation, or topical, particularly to the ears, nose, eyes, or skin. The mode of administration is left to the discretion of the practitioner. In most instances, administration will result in the release of the 4-Tetrazolyl-4-phenylpiperidine Compounds into the bloodstream.

In specific embodiments, it may be desirable to administer the 4-Tetrazolyl-4-phenylpiperidine Compounds locally. This may be achieved, for example, and not by way of limitation, by local infusion during surgery, topical application, e.g., in conjunction with a wound dressing after surgery, by injection, by means of a catheter, by means of a suppository, or by means of an implant, said implant being of a porous, non porous, or gelatinous material, including membranes, such as sialastic membranes, or fibers.

Pulmonary administration can also be employed, e.g., by use of an inhaler or nebulizer, and formulation with an aerosolizing agent, or via perfusion in a fluorocarbon or synthetic pulmonary surfactant. In certain embodiments, the 4-Tetrazolyl-4-phenylpiperidine Compounds can be formulated as a suppository, with traditional binders and excipients such as triglycerides.

In another embodiment, the 4-Tetrazolyl-4-sphenylpiperidine Compounds can be delivered in a vesicle, in particular a liposome (see Langer, *Science* 249:1527-1533 (1990) and Treat et al., *Liposomes in the Therapy of Infectious Disease and Cancer* 317-327 and 353-365 (1989).

In yet another embodiment, the 4-Tetrazolyl-4-phenylpiperidine Compounds can be delivered in a controlled-release system (see, e.g., Goodson, in *Medical Applications of Controlled Release*, supra, vol. 2, pp. 115-138 (1984)). Other controlled release systems discussed in the review by Langer, *Science* 249:1527-1533 (1990) may be used. In one embodiment, a pump may be used (Langer, *Science* 249:1527-1533 (1990); Sefton, *CRC Crit. Ref. Biomed. Eng.* 14:201 (1987); Buchwald et al., *Surgery* 88:507 (1980); and Saudek et al., *N. Engl. J. Med.* 321:574 (1989)). In another embodiment, polymeric materials can be used (see *Medical Applications of Controlled Release* (Langer and Wise eds., 1974); *Controlled Drug Bioavailability, Drug Product Design and Performance*

(Smolen and Ball eds., 1984); Ranger and Peppas, *J. Macromol. Sci. Rev. Macromol. Chem.* 23:61 (1983); Levy et al., *Science* 228:190 (1985); During et al., *Ann. Neurol.* 25:351 (1989); and Howard et al., *J. Neurosurg.* 71:105 (1989)). In yet another embodiment, a controlled release system can be placed in proximity of a target of a 4-Tetrazolyl-4-phenylpiperidine Compound thus requiring only a fraction of the systemic dose.

The present compositions can optionally comprise a suitable amount of a pharmaceutically acceptable excipient so as to provide the form for proper administration to the animal.

Such pharmaceutical excipients can be liquids, such as water and oils, including those of petroleum, animal, vegetable, or synthetic origin, such as peanut oil, soybean oil, mineral oil, sesame oil and the like. The pharmaceutical excipients can be saline, gum acacia, gelatin, starch paste, talc, keratin, colloidal silica, urea, and the like. In addition, auxiliary, stabilizing, thickening, lubricating, and coloring agents may be used. When administered to an animal, the pharmaceutically acceptable excipients can be sterile. Water is a particularly useful excipient when the 4-Tetrazolyl-4-phenylpiperidine Compound is administered intravenously. Saline solutions and aqueous dextrose and glycerol solutions can also be employed as liquid excipients, particularly for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The present compositions, if desired, can also contain minor amounts of wetting or emulsifying agents, or pH buffering agents.

Suitable pharmaceutically acceptable carriers or excipients for intravenous administration of the 4-Tetrazolyl-4-phenylpiperidine Compounds include, but are not limited to, normal (about 0.9%) saline, about 25 to about 30% polyethylene glycol ("PEG") diluted with saline or water, and about 2 to about 30% hydroxypropyl β-cyclodextrin diluted with water.

Suitable pharmaceutically acceptable carriers or excipients for intraperitoneal administration of the 4-Tetrazolyl-4-phenylpiperidine Compounds include, but are not limited to, normal (about 0.9%) saline, about 25 to about 30% PEG diluted with saline or water, about 25 to about 30% propylene glycol (PG) diluted with saline or water, and about 2 to about 30% hydroxypropyl β-cyclodextrin diluted with water.

Suitable pharmaceutically acceptable carriers or excipients for subcutaneous and intramuscular administration of the 4-Tetrazolyl-4-phenylpiperidine Compounds include, but are not limited to, water, normal (about 0.9%) saline, about 25 to about 30% PEG diluted with saline or water, and about 25 to about 30% PG diluted with saline or water.

Suitable pharmaceutically acceptable carriers or excipients for oral administration of the 4-Tetrazolyl-4-phenylpiperidine Compounds include, but are not limited to, water, normal (about 0.9%) saline, about 25 to about 30% polyethylene glycol PEG diluted with saline or water, about 2 to about 30% hydroxypropyl β-cyclodextrin diluted with water, about 25 to about 30% PG diluted with saline or water, and about 1 to about 5% methylcellulose diluted with water.

Suitable pharmaceutically acceptable carriers or excipients for intracerebroventricular and intrathecal administration of the 4-Tetrazolyl-4-phenylpiperidine Compounds include, but are not limited to, normal (about 0.9%) saline.

The present compositions can take the form of solutions, suspensions, emulsion, tablets, pills, pellets, capsules, capsules containing liquids, powders, sustained release formulations, suppositories, aerosols, sprays, suspensions, or any other form suitable for use. In one embodiment, the composition is in the form of a capsule (see e.g., U.S. Pat. No. 5,698,155). Other examples of suitable pharmaceutical excipients are described in *Remington's Pharmaceutical Sciences* 1447-1676 (Alfonso R. Gennaro ed., 19th ed. 1995), incorporated herein by reference.

In one embodiment, the 4-Tetrazolyl-4-phenylpiperidine Compounds are formulated in accordance with routine procedures as a composition adapted for oral administration to an animal, particularly a human being. Compositions for oral delivery may be in the form of tablets, lozenges, aqueous or oily suspensions, granules, powders, emulsions, capsules, syrups, or elixirs, for example. Orally administered compositions can contain preserving agents, coloring agents, and one or more agents, for example, sweetening agents such as fructose, aspartame or saccharin and flavoring agents such as peppermint, oil of wintergreen, or cherry, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving compound are also suitable for orally administered compositions. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate-release formulations. A time delay material such as glycerol monostearate or glycerol stearate may also be used. Oral compositions can include standard excipients such as mannitol, lactose, starch, magnesium stearate, sodium saccharin, cellulose and magnesium carbonate. In one embodiment, such excipients are of pharmaceutical grade.

In another embodiment, the 4-Tetrazolyl-4-phenylpiperidine Compounds can be formulated for intravenous administration. In one embodiment, compositions for intravenous administration comprise the compound dissolved in sterile isotonic aqueous buffer. Where necessary, the compositions may also include a solubilizing agent. Compositions for intravenous administration can optionally include a local anesthetic such as lignocaine to lessen pain at the site of the injection. Generally, the ingredients are supplied either separately or mixed together in unit dosage form, for example, as a dry lyophilized powder or water-free concentrate in a hermetically sealed container such as an ampoule or sachette indicating the quantity of active agent. Where the 4-Tetrazolyl-4-phenylpiperidine Compounds are to be administered by infusion, they can be dispensed, for example, from an infusion bottle containing sterile pharmaceutical grade water or saline. Where the 4-Tetrazolyl-4-phenylpiperidine Compounds are administered by injection, an ampoule of sterile water for injection or saline can be provided so that the ingredients may be mixed prior to administration.

The 4-Tetrazolyl-4-phenylpiperidine Compounds can be administered by controlled-release means or by delivery devices that are well known to those of ordinary skill in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,566, each of which is incorporated herein by reference. Such dosage forms can be used to provide slow or controlled release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled release formulations known to those of ordinary skill in the art, including those described herein, can be readily selected for use with the 4-Tetrazolyl-4-phenylpiperidine Compounds. The invention thus encompasses single unit dosage forms suitable for oral administration such as, but not limited to, tablets, capsules, gelcaps, and caplets that are adapted for controlled release.

Controlled release pharmaceutical compositions can have a common goal of improving drug therapy over that achieved by their non controlled counterparts. In one embodiment a controlled-release composition comprises a minimal amount of a 4-Tetrazolyl-4-phenylpiperidine Compound to cure or control the condition in a minimum amount of time. Advantages of controlled release compositions include extended activity of the drug, reduced dosage frequency, and increased patient compliance. In addition, controlled release compositions can favorably affect the time of onset of action or other characteristics, such as blood levels of the 4-Tetrazolyl-4-phenylpiperidine Compound, and can thus reduce the occurrence of side (e.g., adverse) effects.

In one embodiment, controlled release compositions can initially release an amount of a 4-Tetrazolyl-4-phenylpiperidine Compound that promptly treats or prevents pain or diarrhea, and gradually and continually release other amounts of the 4-Tetrazolyl-4-phenylpiperidine Compound to maintain this level of therapeutic or prophylactic effect over an extended period of time. To maintain this constant level of the 4-Tetrazolyl-4-phenylpiperidine Compound in the body, the 4-Tetrazolyl-4-phenylpiperidine Compound can be released from the dosage form at a rate that will replace the amount of 4-Tetrazolyl-4-phenylpiperidine Compound being metabolized and excreted from the body. Controlled release of an active ingredient can be stimulated by various conditions including, but not limited to, changes in pH, changes in temperature, concentration or availability of enzymes, concentration or availability of water, or other physiological conditions or compounds.

The amount of the 4-Tetrazolyl-4-phenylpiperidine Compounds that is effective in the treatment or prevention of pain or diarrhea can depend on the nature or severity of the disorder or condition causing the pain and can be determined by standard clinical techniques. In addition, in vitro or in vivo assays can optionally be employed to help identify optimal effective dosage amounts. The precise dose to be employed can also depend on the intended route of administration, and the degree or severity of the pain or diarrhea and should be decided according to the judgment of the practitioner and each patient's circumstances in view of published clinical studies. Suitable effective dosage amounts, however, range from about 10 micrograms to about 2500 milligrams about every 4 h, although typically about 100 mg or less. In one embodiment, the effective dosage amount ranges from about 0.01 milligrams to about 100 milligrams of a 4-Tetrazolyl-4-phenylpiperidine Compound about every 4 h, in another embodiment about 0.020 milligrams to about 50 milligrams about every 4 h, and in another embodiment about 0.025 milligrams to about 20 milligrams about every 4 h. The dosage amounts described herein refer to total amounts administered; that is, if more than one 4-Tetrazolyl-4-phenylpiperidine Compound is administered, the effective dosage amounts correspond to the total amount administered.

Where a cell capable of expressing an opioid receptor is contacted with a 4-Tetrazolyl-4-phenylpiperidine Compound in vitro, the effective amount will typically range from about 0.01 mg to about 100 mg/L, in one embodiment from about 0.1 mg to about 50 mg/L, and in another embodiment from about 1 mg to about 20 mg/L, of a solution or suspension of a pharmaceutically acceptable carrier or excipient.

Where a cell capable of expressing an opioid receptor is contacted with a 4-Tetrazolyl-4-phenylpiperidine Compound in vivo, the effective amount will typically range from about 0.01 mg to about 100 mg/kg of body weight per day, in one embodiment from about 0.1 mg to about 50 mg/kg body weight per day, and in another embodiment from about 1 mg to about 20 mg/kg of body weight per day.

The 4-Tetrazolyl-4-phenylpiperidine Compounds can be assayed in vitro or in vivo for its their ability to treat or prevent pain or diarrhea prior to use in humans. Animal model systems can be used to demonstrate the 4-Tetrazolyl-4-phenylpiperidine Compounds' safety or efficacy.

The present methods for treating or preventing pain or diarrhea in an animal can further comprise administering to the animal an effective amount of another therapeutic agent.

The present methods for stimulating opioid-receptor function in a cell can further comprise contacting the cell with an effective amount of another therapeutic agent.

Examples of other therapeutic agents include, but are not limited to, an opioid agonist, a non-opioid analgesic, a non-steroid antiinflammatory agent, an antimigraine agent, a Cox-II inhibitor, an antiemetic, a β-adrenergic blocker, an anticonvulsant, an antidepressant, a Ca2+-channel blocker, an anticancer agent, an anti-anxiety agent, an agent for treating or preventing an addictive disorder and mixtures thereof.

Effective amounts of the other therapeutic agents are well known to those skilled in the art. However, it is well within the skilled artisan's purview to determine the other therapeutic agent's optimal effective-amount range. In one embodiment of the invention, where another therapeutic agent is administered to an animal, the effective amount of the 4-Tetrazolyl-4-phenylpiperidine Compound is less than its effective amount would be where the other therapeutic agent is not administered. In this case, without being bound by theory, it is believed that the 4-Tetrazolyl-4-phenylpiperidine Compound and the other therapeutic agent act synergistically to treat or prevent pain or diarrhea.

Examples of useful opioid agonists include, but are not limited to, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, proheptazine, promedol, properidine, propiram, propoxyphene, sufentanil, tilidine, tramadol, pharmaceutically acceptable salts thereof, and mixtures thereof.

In certain embodiments, the opioid agonist is selected from codeine, hydromorphone, hydrocodone, oxycodone, dihydrocodeine, dihydromorphine, morphine, tramadol, oxymorphone, pharmaceutically acceptable salts thereof, and mixtures thereof.

Examples of useful non opioid analgesics include non steroidal anti-inflammatory agents, such as aspirin, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam, isoxicam, and pharmaceutically acceptable salts thereof, and mixtures thereof. Examples of other suitable non opioid analgesics include the following, non limiting, chemical classes of analgesic, antipyretic, nonsteroidal antiinflammatory drugs: salicylic acid derivatives, including aspirin, sodium salicylate, choline magnesium trisalicylate, salsalate, diflunisal, salicylsalicylic acid, sulfasalazine, and olsalazin; para aminophennol derivatives including acetaminophen and phenacetin; indole and indene acetic acids, including indomethacin, sulindac, and etodolac; heteroaryl acetic acids, including tolmetin, diclofenac, and ketorolac; anthranilic acids (fenamates), including mefenamic acid, and meclofenamic acid; enolic acids, including oxicams (piroxicam, tenoxicam), and pyrazolidinediones (phenylbutazone, oxyphenthartazone); and alkanones, including nabumetone. For a more detailed description of the NSAIDs, see Paul A. Insel, *Analgesic Antipyretic and Antiinflammatory Agents and Drugs Employed in the Treatment of Gout*, in Goodman & Gilman's *The Pharmacological Basis of Therapeutics* 617-57 (Perry B. Molinhoff and Raymond W. Ruddon eds., 9th ed 1996) and Glen R. Hanson, *Analgesic, Antipyretic and Anti Inflammatory Drugs* in Remington: *The Science and Practice of Pharmacy* Vol II 1196-1221 (A. R. Gennaro ed. 19th ed. 1995) which are hereby incorporated by reference in their entireties. Suitable Cox-II inhibitors and 5-lipoxygenase inhibitors, as well as combinations thereof, are described in U.S. Pat. No. 6,136,839. Cox II inhibitors include, but are not limited to, rofecoxib and celecoxib.

Examples of useful antimigraine agents include, but are not limited to, alpiropride, dihydroergotamine, dolasetron, ergocomine, ergocorninine, ergocryptine, ergot, ergotamine, flumedroxone acetate, fonazine, lisuride, lomerizine, methysergide oxetorone, pizotyline, and mixtures thereof.

The other therapeutic agent can also be an antiemetic agent. Useful antiemetic agents include, but are not limited to, metoclopromide, domperidone, prochlorperazine, promethazine, chlorpromazine, trimethobenzamide, ondansetron, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxypemdyl, pipamazine, scopolamine, sulpiride, tetrahydrocannabinol, thiethylperazine, thioproperazine, tropisetron, and mixtures thereof.

Examples of useful β-adrenergic blockers include, but are not limited to, acebutolol, alprenolol, amosulabol, arotinolol, atenolol, befunolol, betaxolol, bevantolol, bisoprolol, bopindolol, bucumolol, bufetolol, bufuralol, bunitrolol, bupranolol, butidrine hydrochloride, butofilolol, carazolol, carteolol, carvedilol, celiprolol, cetamolol, cloranolol, dilevalol, epanolol, esmolol, indenolol, labetalol, levobunolol, mepindolol, metipranolol, metoprolol, moprolol, nadolol, nadoxolol, nebivalol, nifenalol, nipradilol, oxprenolol, penbutolol, pindolol, practolol, pronethalol, propranolol, sotalol, sulfinalol, talinolol, tertatolol, tilisolol, timolol, toliprolol, and xibenolol.

Examples of useful anticonvulsants include, but are not limited to, acetylpheneturide, albutoin, aloxidone, aminoglutethimide, 4-amino-3-hydroxybutyric acid, atrolactamide, beclamide, buramate, calcium bromide, carbamazepine, cinromide, clomethiazole, clonazepam, decimemide, diethadione, dimethadione, doxenitroin, eterobarb, ethadione, ethosuximide, ethotoin, felbamate, fluoresone, gabapentin, 5-hydroxytryptophan, lamotrigine, magnesium bromide, magnesium sulfate, mephenyloin, mephobarbital, metharbital, methetoin, methsuximide, 5-methyl-5-(3-phenanthryl)-hydantoin, 3-methyl-5-phenylhydantoin, narcobarbital, nimetazepam, nitrazepam, oxcarbazepine, paramethadione, phenacemide, phenetharbital, pheneturide, phenobarbital, phensuximide, phenylmethylbarbituric acid, phenyloin, phethenylate sodium, potassium bromide, pregabaline, primidone, progabide, sodium bromide, solanum, strontium bromide, suclofenide, sulthiame, tetrantoin, tiagabine, topiramate, trimethadione, valproic acid, valpromide, vigabatrin, and zonisamide.

Examples of useful antidepressants include, but are not limited to, binedaline, caroxazone, citalopram, (S)-citalopram, dimethazan, fencamine, indalpine, indeloxazine hydrocholoride, nefopam, nomifensine, oxitriptan, oxypertine, paroxetine, sertraline, thiazesim, trazodone, bemnoxine, iproclozide, iproniazid, isocarboxazid, nialamide, octamoxin, phenelzine, cotinine, rolicyprine, rolipram, maprotiline, metralindole, mianserin, mirtazepine, adinazolam, amitriptyline, amitriptylinoxide, amoxapine, butriptyline, clomipramine, demexiptiline, desipramine, dibenzepin, dimetacrine, dothiepin, doxepin, fluacizine, imipramine, imipramine N-oxide, iprindole, lofepramine, melitracen, metapramine, nortriptyline, noxiptilin, opipramol, pizotyline, propizepine, protriptyline, quinupramine, tianeptine, trimipramine, adrafinil, benactyzine, bupropion, butacetin, dioxadrol, duloxetine, etoperidone, febarbamate, femoxetine, fenpentadiol, fluoxetine, fluvoxamine, hematoporphyrin, hypericin, levophacetoperane, medifoxamine, milnacipran, minaprine, moclobemide, nefazodone, oxaflozane, piberaline, prolintane, pyrisuccideanol, ritanserin, roxindole, rubidium chloride, sulpiride, tandospirone, thozalinone, tofenacin, toloxatone, tranylcypromine, L-tryptophan, venlafaxine, viloxazine, and zimeldine.

Examples of useful Ca2+-channel blockers include, but are not limited to, bepridil, clentiazem, diltiazem, fendiline, gallopamil, mibefradil, prenylamine, semotiadil, terodiline, verapamil, amlodipine, aranidipine, barnidipine, benidipine, cilnidipine, efonidipine, elgodipine, felodipine, isradipine, lacidipine, lercanidipine, manidipine, nicardipine, nifedipine, nilvadipine, nimodipine, nisoldipine, nitrendipine, cinnarizine, flunarizine, lidoflazine, lomerizine, bencyclane, etafenone, fantofarone, and perhexiline.

Examples of useful anticancer agents include, but are not limited to, acivicin, aclarubicin, acodazole hydrochloride, acronine, adozelesin, aldesleukin, altretamine, ambomycin, ametantrone acetate, aminoglutethimide, amsacrine, anastrozole, anthramycin, asparaginase, asperlin, azacitidine, azetepa, azotomycin, batimastat, benzodepa, bicalutamide, bisantrene hydrochloride, bisnafide dimesylate, bizelesin, bleomycin sulfate, brequinar sodium, bropirimine, busulfan, cactinomycin, calusterone, caracemide, carbetimer, carboplatin, carmustine, carubicin hydrochloride, carzelesin, cedefingol, chlorambucil, cirolemycin, cisplatin, cladribine, crisnatol mesylate, cyclophosphamide, cytarabine, dacarbazine, dactinomycin, daunorubicin hydrochloride, decitabine, dexormaplatin, dezaguanine, dezaguanine mesylate, diaziquone, docetaxel, doxorubicin, doxorubicin hydrochloride, droloxifene, droloxifene citrate, dromostanolone propionate, duazomycin, edatrexate, eflornithine hydrochloride, elsamitrucin, enloplatin, enpromate, epipropidine, epirubicin hydrochloride, erbulozole, esorubicin hydrochloride, estramustine, estramustine phosphate sodium, etanidazole, etoposide, etoposide phosphate, etoprine, fadrozole hydrochloride, fazarabine, fenretinide, floxuridine, fludarabine phosphate, fluorouracil, flurocitabine, fosquidone, fostriecin sodium, gemcitabine, gemcitabine hydrochloride, hydroxyurea, idarubicin hydrochloride, ifosfamide, ilmofosine, interleukin II (including recombinant interleukin II or rIL2), interferon alfa-2a, interferon alfa-2b, interferon alfa-n1, interferon alfa-n3, interferon beta-I a, interferon gamma-I b, iproplatin, irinotecan hydrochloride, lanreotide acetate, letrozole, leuprolide acetate, liarozole hydrochloride, lometrexol sodium, lomustine, losoxantrone hydrochloride, masoprocol, maytansine, mechlorethamine hydrochloride, megestrol acetate, melengestrol acetate, melphalan, menogaril, mercaptopurine, methotrexate, methotrexate sodium, metoprine, meturedepa, mitindomide, mitocarcin, mitocromin, mitogillin, mitomalcin, mitomycin, mitosper, mitotane, mitoxantrone hydrochloride, mycophenolic acid, nocodazole, nogalamycin, ormaplatin, oxisuran, paclitaxel, pegaspargase, peliomycin, pentamustine, peplomycin sulfate, perfosfamide, pipobroman, piposulfan, piroxantrone hydrochloride, plicamycin, plomestane, porfimer sodium, porfiromycin, prednimustine, procarbazine hydrochloride, puromycin, puromycin hydrochloride, pyrazofurin, riboprine, rogletimide, safingol, safingol hydrochloride, semustine, simtrazene, sparfosate sodium, sparsomycin, spirogermanium hydrochloride, spiromustine, spiroplatin, streptonigrin, streptozocin, sulofenur, talisomycin, tecogalan sodium, tegafur, teloxantrone hydrochloride, temoporfin, teniposide, teroxirone, testolactone, thiamiprine, thioguanine, thiotepa, tiazofurin, tirapazamine, toremifene citrate, trestolone acetate, triciribine phosphate, trimetrexate, trimetrexate glucuronate, triptorelin, tubulozole hydrochloride, uracil mustard, uredepa, vapreotide, verteporfin, vinblastine sulfate, vincristine sulfate, vindesine, vindesine sulfate, vinepidine sulfate, vinglycinate sulfate, vinleurosine sulfate, vinorelbine tartrate, vinrosidine sulfate, vinzolidine sulfate, vorozole, zeniplatin, zinostatin, zorubicin hydrochloride.

Examples of other anti cancer drugs include, but are not limited to, 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol; 9-dioxamycin; diphenyl spiromustine; docetaxel; docosanol; dolasetron; doxifluridine; droloxifene; dronabinol; duocarmycin SA; ebselen; ecomustine; edelfosine; edrecolomab; eflomithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; 4-ipomeanol; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor-1 based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide;

rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Therapeutic agents useful for treating or preventing an addictive disorder include, but are not limited to, methadone, desipramine, amantadine, fluoxetine, buprenorphine, an opiate agonist, 3-phenoxypyridine, or a serotonin antagonist.

Examples of useful anti-anxiety agents include, but are not limited to, benzodiazepines, such as alprazolam, chlordiazepoxide, clonazepam, clorazepate, diazepam, halazepam, lorazepam, oxazepam, and prazepam; non-benzodiazepine agents, such as buspirone; and tranquilizers, such as barbiturates.

Examples of useful anti-diarrheal agents include, but are not limited to, loperamide, diphenoxylate with atropine, clonidine, octreotide, and cholestyramine.

A 4-Tetrazolyl-4-phenylpiperidine Compound and the other therapeutic agent can act additively or, in one embodiment, synergistically. In one embodiment, a 4-Tetrazolyl-4-phenylpiperidine Compound is administered concurrently with another therapeutic agent; for example, a composition comprising an effective amount of a 4-Tetrazolyl-4-phenylpiperidine Compound, an effective amount of another therapeutic agent can be administered. Alternatively, a composition comprising an effective amount of a 4-Tetrazolyl-4-phenylpiperidine Compound and a different composition comprising an effective amount of another therapeutic agent can be concurrently administered. In another embodiment, an effective amount of a 4-Tetrazolyl-4-phenylpiperidine Compound is administered prior or subsequent to administration of an effective amount of another therapeutic agent. In this embodiment, the 4-Tetrazolyl-4-phenylpiperidine Compound is administered while the other therapeutic agent exerts its therapeutic effect, or the other therapeutic agent is administered while the 4-Tetrazolyl-4-phenylpiperidine Compound exerts its preventive or therapeutic effect for treating or preventing pain or diarrhea.

A composition of the invention is prepared by a method comprising admixing a 4-Tetrazolyl-4-phenylpiperidine Compound or a pharmaceutically acceptable salt thereof and a pharmaceutically acceptable carrier or excipient. Admixing can be accomplished using methods known for admixing a compound (or salt) and a pharmaceutically acceptable carrier or excipient. In one emobodiment the composition is prepared such that the 4-Tetrazolyl-4-phenylpiperidine Compound is present in the composition in an effective amount.

4.4.2 Kits

The invention encompasses kits that can simplify the administration of a 4-Tetrazolyl-4-phenylpiperidine Compound to an animal.

A typical kit of the invention comprises a unit dosage form of a 4-Tetrazolyl-4-phenylpiperidine Compound. In one embodiment, the unit dosage form is a container, in one embodiment a sterile container, containing an effective amount of a 4-Tetrazolyl-4-phenylpiperidine Compound and a pharmaceutically acceptable carrier or excipient. The kit can further comprise a label or printed instructions instructing the use of the 4-Tetrazolyl-4-phenylpiperidine Compound to treat or prevent pain or diarrhea. The kit can also further comprise a unit dosage form of another therapeutic agent, for example, a container containing an effective amount of the other therapeutic agent. In one embodiment, the kit comprises a container containing an effective amount of a 4-Tetrazolyl-4-phenylpiperidine Compound and an effective amount of another therapeutic agent. Examples of other therapeutic agents include, but are not limited to, those listed above.

Kits of the invention can further comprise a device that is useful for administering the unit dosage forms. Examples of such devices include, but are not limited to, syringes, drip bags, patches, enema bags, and inhalers.

The following examples are set forth to assist in understanding the invention and should not, of course, be construed as specifically limiting the invention described and claimed herein. Such variations of the invention, including the substitution of all equivalents now known or later developed, which would be within the purview of those skilled in the art, and changes in formulation or minor changes in experimental design, are to be considered to fall within the scope of the invention incorporated herein.

5. EXAMPLES

Examples 1-7 relate to the synthesis of illustrative 4-Tetrazolyl-4-phenylpiperidine Compounds of the present invention.

5.1 Example 1

Synthesis of Compound AAA

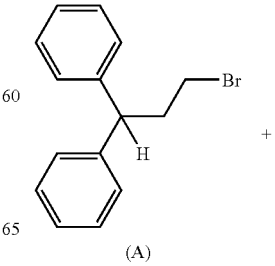

(A)

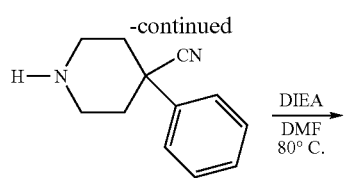

(B)

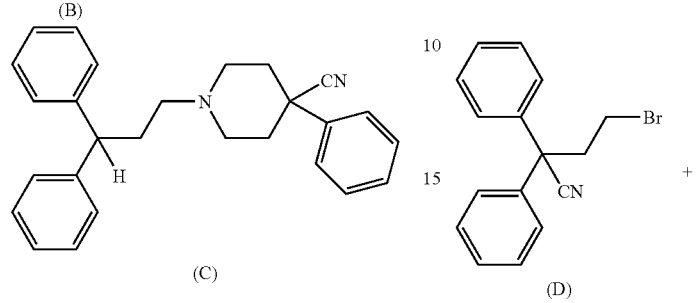

(C)

To a solution of (A) (3.0 mmol) and (B) (3.0 mmol) in 10 ml DMF were added 1.2 equivalents of DIEA. The mixture was stirred at 80° C. overnight. The reaction mixture was cooled, diluted with ethyl acetate, and washed with water (20 ml×2). The aqueous layer was extracted once with ethyl acetate (25 ml). The combined organic phases were dried ($Na_2SO_4$) and the solvent was removed on a rotoevaporator. The residue was purified by column chromatography (5% $NEt_3$/25% EtOAc/70% hexane) to give the desired product (C) as a colorless solid. Compound (C): Yield: 85%, purity (HPLC)>97%; MS: m/z 381.3; $^1H$ NMR ($CDCl_3$): δ 2.05-2.15 (m, 4H), 2.25-2.35 (m, 2H), 2.4-2.5 (m, 4H), 2.95-3.05 (m, 2H), 4.0 (t, 1H), 7.1-7.4 (m, 11H), 7.4-7.5 (m, 2H), 7.5-7.55 (m, 2H).

Scheme 12

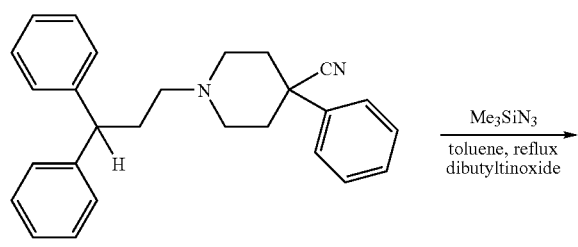

(C)

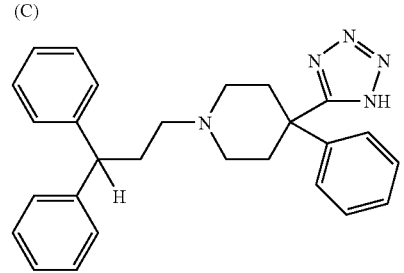

AAA

To a solution of (C) (0.5 mmol) in 10 ml toluene were added 2 equivalents of $Me_3SiN_3$ and 0.1 eq of dibutyl tinoxide. The mixture was stirred at reflux under an argon atmosphere for 24 hours. LC/MS indicated a complete reaction. The solvent was evaporated in vacuo. The crude materials was dissolved in $CHCl_3$ and loaded onto the column which was loaded with 5 g of silica gel. Flash chromatography was carried out eluting with 5% $Et_3N$, 25% ethyl acetate and 70% Hexane, then 10% $Et_3N$, 40% EtOAc, 50% Hexane. Finally eluting with 2% $NH_3/H_2O$, 15% methanol, and 83% $CH_2Cl_2$. This gave the compound (AAA) as a solid. Compound (AAA): Yield 30%; Purity (HPLC)>97%; MS: m/z 424.2; $^1H$ NMR (MeOD): δ 2.3-2.5 (m, 4H), 2.8-3.1 (m, 6H), 3.4-3.5 (m, 2H), 3.9 (t, 1H), 7.1-7.3 (m, 15H).

5.2 Example 2

Synthesis of Compound ACY

Scheme 13

(D) +

(B)

(E)

To a solution of (D) (3.0 mmol) and (B) (3.0 mmol) in 10 ml DMF were added 1.2 equivalents of DIEA. The mixture was stirred at 80° C. overnight. The reaction mixture was cooled, diluted with ethyl acetate, and washed with water (20 ml×2). The aqueous layer was extracted once with ethyl acetate (25 ml). The combined organic phases were dried ($Na_2SO_4$) and the solvent was removed on rotoevaporator. The residue was purified by column chromatography (5% $NEt_3$/25% EtOAc/70% hexane) to give the desired product (E) as a colorless solid. Compound (E): Yield: 80%; purity (HPLC)>97%; MS: m/z 406.2; $^1H$ NMR ($CDCl_3$): δ 2.0-2.1 (m, 4H), 2.5-2.7 (m, 6H), 2.9-3.0 (m, 2H), 7.3-7.5 (m, 15H).

Scheme 14

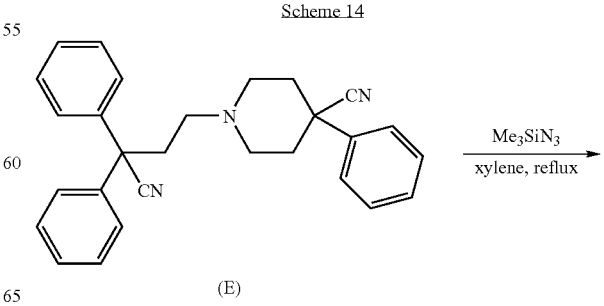

(E)

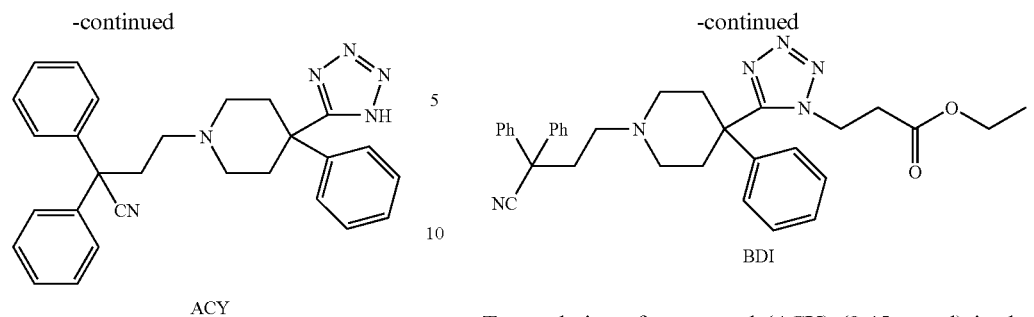

ACY

To a solution of (E) (4.0 mmol) in 15 ml p-xylene were added 1.1 equivalents of $Me_3SnN_3$. The mixture was stirred at reflux under an argon atmosphere for 36 hours. The reaction mixture was cooled and poured into 150 ml 1M NaOH. Diethyl ether (150 ml) was added and this solution was allowed to stir at room temperature for 1 hour. The layers were separated and the aqueous layer extracted with diethyl ether (150 ml×1). The aqueous layer was acidified to pH 6.3 with acetic acid/ammonium acetate. The solid was filtered, washed with water (100 ml), and triturated with cold methanol to give the product as a white solid. Flash chromatography eluting with ethyl acetate, then ethyl acetate:methanol (70: 30), gave compound (ACY) as a white solid. Compound (ACY) (5.0 g, 11.14 mmol) was suspended in boiling methanol (200 mL) with stirring. Sulfamic acid (1.08 g 11.14 mmol) in hot water (5 mL) was added to form a clear solution. This was allowed to cool slowly for several hours, then filtered to provide the sulfamate salt of compound (ACY) (4.46 g, 73%) as white needles. Compound (ACY) (sulfamate salt): purity >97% (HPLC); MS: m/z 449.2; $^1$H NMR (DMSO-d6): δ 2.25-2.4 (m, 2H), 2.4-2.5 (m, 2H), 2.55-2.65 (m, 2H), 2.7-2.85 (m, 4H), 3.1-3.25 (m, 2H), 3.3-3.4 (bs, 2H), 7.2-7.3 (m, 3H), 7.3-7.4 (m, 4H), 7.4-7.5 (m, 8H).

5.3 Example 3

Synthesis of Compound ADI and BDI

To a solution of compound (ACY) (0.45 mmol) in dry DMF was added triethylamine (0.54 mmol), followed by the alkylating agent Br $(CH_2)_2C(O)O(CH_2CH_3)$ (0.54 mmol). The resulting mixture was stirred at 80° C. overnight. After completion of the reaction, the cooled mixture was partitioned between ether and brine, and the organic phase was separated, dried ($MgSO_4$), and the solvent was removed at the rotary evaporator to yield a colorless to pale yellow gum. Trituration with ether/hexanes or ether/ethylacetate (1:1, 10 mL) precipitated compound (ADI) as a white solid from the mother liquor: yield: 24%; purity (HPLC)>97%; MS: m/z 549.3 (M+1); $^1$H NMR (DMSO d6): δ 2.2-2.6 (m, 6H), 2.7-2.9 (m, 4H), 3.05 (t, 3H), 3.2-3.4 (m, 4H), 3.95 (q, 2H), 4.9 (t, 2H), 7.1-8.1 (m, 17H).

The mother liquor comprises compound (ADI) and compound (BDI), which are separated using conventional separation methods.

5.4 Example 4

Synthesis of Compound ADQ and BDQ

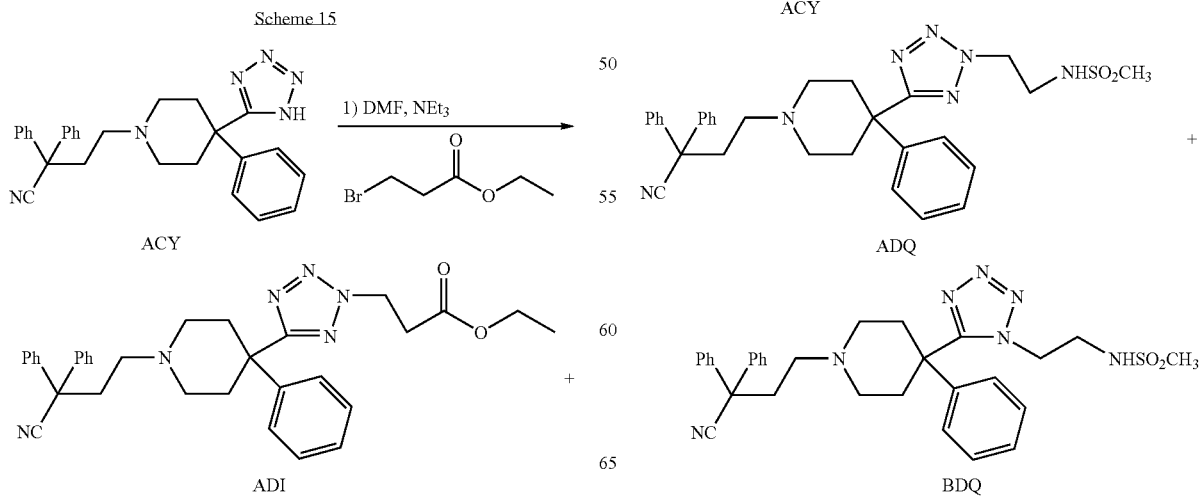

To a solution of compound (ACY) (0.45 mmol) in dry DMF was added triethylamine (0.54 mmol), followed by the alkylating agent (Br (CH$_2$)$_2$NHSO$_2$CH$_3$) (0.54 mmol). The resulting mixture was stirred at 80° C. overnight. After completion of the reaction, the cooled mixture was partitioned between ether and brine, and the organic phase was separated, dried (MgSO$_4$), and the solvent was removed at the rotary evaporator to yield a colorless to pale yellow gum. Trituration with ether/hexanes or ether/ethylacetate (1:1, 10 mL) precipitated compound (ADQ) as a white solid from the mother liquor: yield: 59%; purity (HPLC)>97%; MS: m/z 570.2 (M+1); $^1$H NMR (CD$_3$OD): δ 2.1-2.3 (m, 6H), 2.6-2.7 (m, 2H), 2.75 (s, 3H) 2.85 (d, 4H), 3.25-3.35 (m, 1H), 3.6 (t, 2H), 4.65 (t, 2H), 7.15-7.2 (m, 1H), 7.25-7.35 (m, 6H), 7.38-7.45 (m, 8H).

The mother liquor comprises compound comprises compound (ADQ) and compound (BDQ), which are separated using conventional separation methods.

5.5 Example 5

Synthesis of Compounds ACZ and BCZ

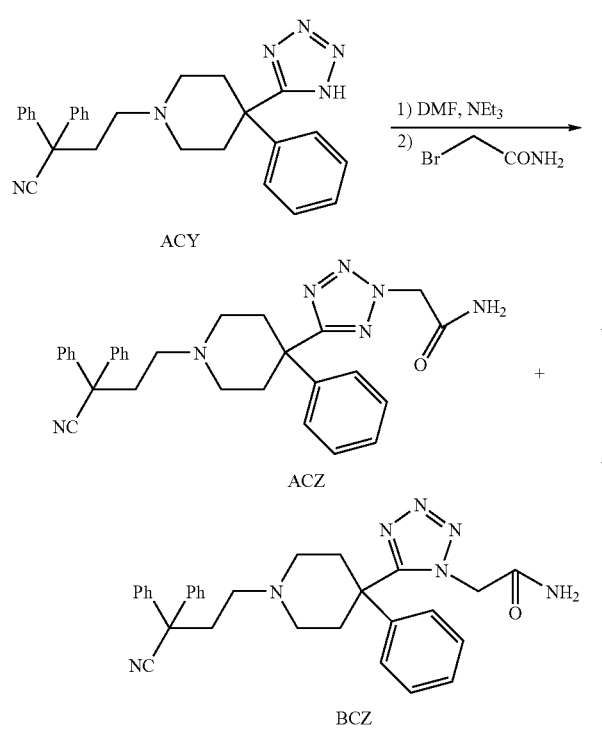

To a solution of (ACY) (0.78 mmol) in dry DMF (5 mL) was added triethylamine (0.94 mmol), followed by 2-bromoacetamide (0.27 mmol). The resulting mixture was heated at 80° C. overnight. After completion of the reaction, the cooled mixture was partitioned between ether and brine, and the organic phase was separated, dried (MgSO$_4$), and the solvent removed at the rotary evaporator to yield a pale yellow gum. Flash chromatography (SiO$_2$, ether:methanol:ammonium hydroxide (1000:4:1)) gave compound (ACZ) as a white solid. (48% yield). Compound (ACZ): purity >97% (HPLC); MS: m/z 506.2 (M+1); $^1$H NMR (DMSO d6): δ 1.8 (m, 2H), 2.2 (m, 4H), 2.6-2.8 (m, 6H), 5.35 (s, 2H), 7.0-7.5 (m, 16H), 7.7 (m, 1H).

Further chromotography provides compound (BCZ).

5.6 Example 6

Synthesis of Compound AFD

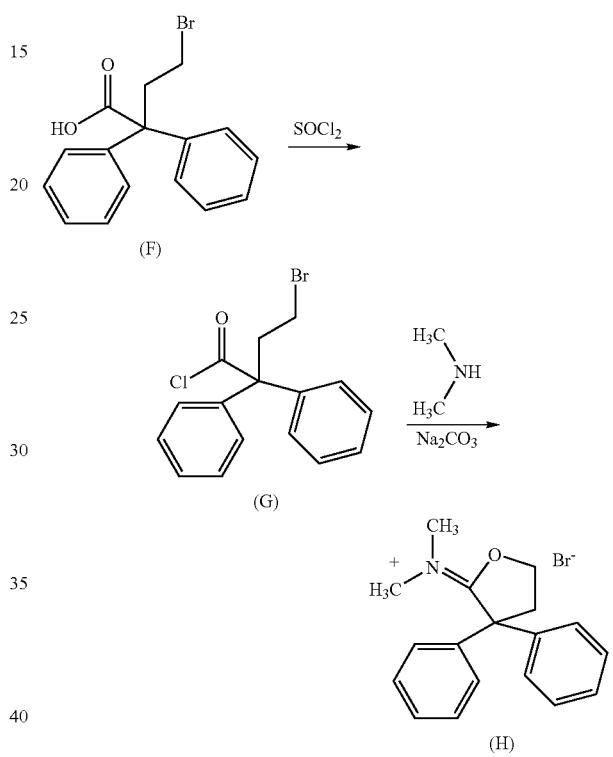

4-Bromo-2,2-diphenylbutyric acid (compound (F), 23 g, 72 mmol) was suspended in 150 mL of chloroform, and 20 mL of thionyl chloride (270 mmol) was added dropwise. After addition of the thionyl chloride, 0.2 mL of dimethylformamide was added, and the resulting solution heated at reflux for about 4 hours. The reaction mixture was then concentrated under reduced pressure to provide 4-bromo-2,2-diphenylbutyric acid chloride (compound (G) as a pale yellow oil that was used in the following step without further purification.

To 100 mL of saturated aqueous Na$_2$CO$_3$ was added 50 mL of a 2M solution of dimethylamine in tetrahydrofuran. The resulting solution was cooled to 0° C. and a solution of compound (G), prepared as described above, dissolved in 100 mL of toluene was added dropwise. The resulting mixture was allowed to stir for about 12 hours. The organic and aqueous layers of the reaction mixture were separated and the aqueous layer was extracted with 30 mL of toluene and then extracted 3 times with 100 mL of chloroform and the organics were combined. The combined organic extracts were washed with water (30 mL), dried (K$_2$CO$_3$), and the solvent was removed under reduced pressure to provide a residue that was crystallized from methyl isobutyl ketone to provide 12 g (53% yield) of dimethyl(tetrahydro-3,3-diphenyl-2-furylidene)ammonium bromide (compound (H)).

Scheme 19

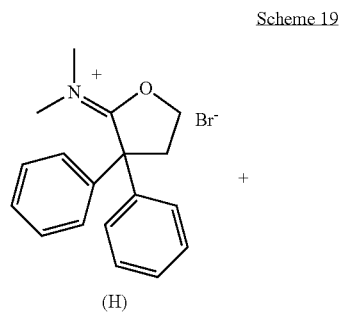

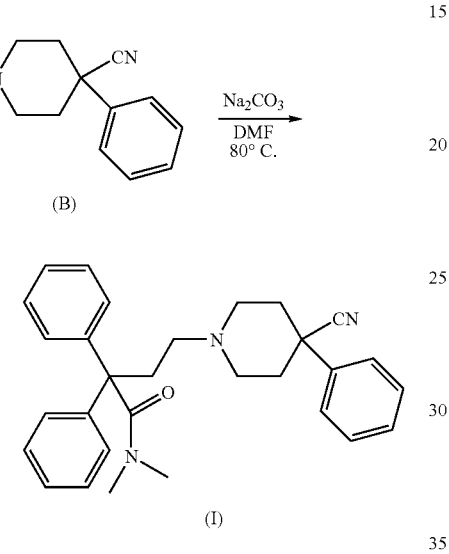

To a solution of compound (H) (3.0 mmol) and (B) (3.0 mmol) in 10 ml DMF were added 3 equivalents of Na$_2$CO$_3$. The mixture was stirred at 80° C. for 3 hours. The reaction mixture was cooled, diluted with ethyl acetate, and washed with water (20 ml×2). The aqueous layer was extracted once with ethyl acetate (25 ml). The combined organics were dried (Na$_2$SO$_4$) and the solvent was removed on a rotoevaporator. The residue was purified by column chromatography (5% NEt$_3$/25% EtOAc/70% hexane) to give product compound (I) as colorless crystals: (yield: 81%); purity (HPLC): >97%; MS: m/z 452.2; $^1$H NMR (CDCl$_3$): δ 2.0-2.1 (m, 4H), 2.2 (m, 2H), 2.3-2.4 (m, 5H), 2.4-2.5 (m, 2H), 2.9 (m, 2H), 3.0 (bs, 3H), 7.2-7.3 (m, 3H), 7.3-7.5 (m, 12H).

Scheme 20

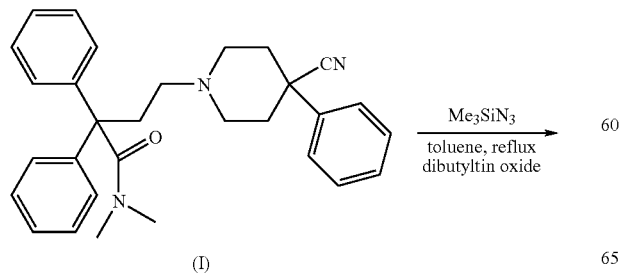

To a solution of compound (I) (0.5 mmol) in 10 ml toluene were added 2 equivalents of Me$_3$SiN$_3$ and 0.1 eq of dibutyl tinoxide. The mixture was stirred at reflux under an argon atmosphere for 24 hours. LC/MS indicated the reaction was complete. The solvent was evaporated under reduced pressure. The crude product was dissolved in CHCl$_3$ and loaded onto the column containing 5 g of silica gel. Flash chromatography was carried out eluting with 5% Et$_3$N, 25% ethyl acetate and 70% hexane, then 10% Et$_3$N, 40% EtOAc, 50% hexane, and finally eluting with 2% NH$_3$/H$_2$O, 15% methanol and 83% CH$_2$Cl$_2$. Compound (AFD) was obtained as a solid (yield: 35%); purity >97% (HPLC); MS: m/z 495.2; $^1$H NMR (DMSO d6): δ 2.2 (bs, 3H), 2.3-2.4 (m, 2H), 2.5 (m, 3H), 2.6-2.7 (m, 2H), 2.7-2.8 (m, 2H), 2.9 (bs, 3H), 3.3-3.4 (bs, 3H), 7.2-7.3 (m, 3H), 7.3-7.4 (m, 4H), 7.4-7.5 (m, 8H).

5.7 Example 7

Synthesis of Compounds AFE and BFE

Scheme 21

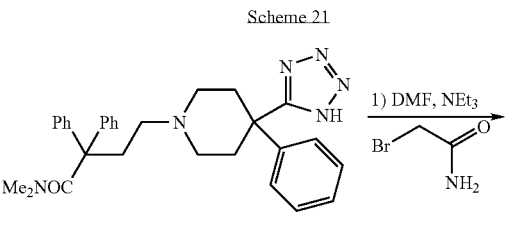

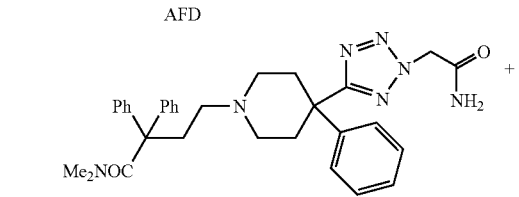

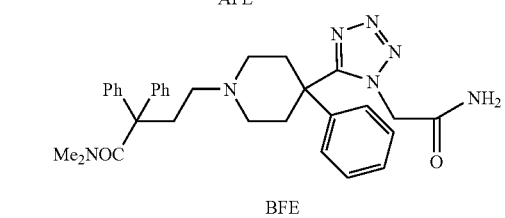

To a solution of compound (AFD) (0.40 mmol) in dry DMF was added triethylamine (0.45), followed by the alkylating agent Br (CH$_2$)C(O)NH$_2$ (0.45 mmol). The resulting mixture was stirred at 80° C. overnight. After completion of the reaction, the cooled mixture was poured into 1M NaOH (150 mL) and extracted with ethyl acetate (2×100 mL). The organic extracts were dried (MgSO$_4$) and the solvent evaporated at the rotary evaporator to leave a gum. Flash chromatography of the residue (SiO$_2$, ether:methanol:ammonium hydroxide (200:10:1)) provided compound (AFE) as a colorless gum: (yield 69%); purity >97% (HPLC); MS: m/z 552.3 (M+1); $^1$H NMR (DMSO d6): δ 2.2-2.3 (br s, 3H), 2.35-3.0 (m, 11H), 3.3-3.4 (m, 4H), 5.35 (s, 2H), 7.15-7.5 (m, 16H), 7.8 (br s, 1H).

Further chromatography provides compound (BFE).

5.8 Example 8

Synthesis of Compounds AFV and BFV

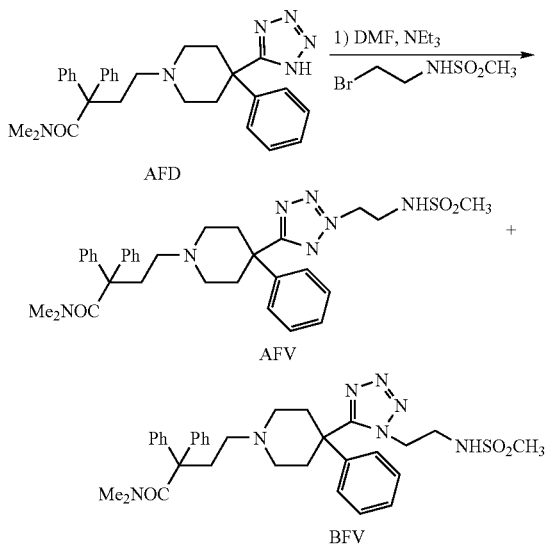

To a solution of compound (AFD) (0.40 mmol) in dry DMF was added triethylamine (0.45), followed by the alkylating agent Br(CH$_2$)$_2$NHSO$_2$CH$_3$ (0.45 mmol). The resulting mixture was stirred at 80° C. overnight. After completion of the reaction, the cooled mixture was poured into 1M NaOH (150 mL) and extracted with ethyl acetate (2×100 mL). The organic extracts were dried (MgSO$_4$) and the solvent evaporated at the rotary evaporator to leave a gum. Flash chromatography of the residue (SiO$_2$, ether:methanol:ammonium hydroxide (200:10:1)) provided compound (AFV) as a colorless gum: (yield: 26%); purity >97% (HPLC); MS: m/z 616.3 (M+1); $^1$H NMR (DMSO d6): δ 2.1-2.2 (br s, 3H), 2.3-2.4 (m, 5H), 2.75 (s, 3H) 2.9-2.10 (br s, 3H), 3.3-3.4 (m, 6H), 3.5 (m, 3H), 4.65 (m, 2H), 7.15-7.5 (m, 16H).

Further chromatography provides compound (BFV).

5.9 Example 22

μ- and ORL-1-Receptor-Binding Affinity Assays

The following example will demonstrate that 4-Tetrazolyl-4-phenylpiperidine Compounds bind to μ- or ORL-1-receptors and, accordingly, are useful for treating or preventing pain or diarrhea.

5.9.1 Materials and Methods

ORL-1 Receptor Membrane Preparation

All reagents are obtained from Sigma (St. Louis, Mo.) unless noted otherwise. Membranes from recombinant HEK-293 cells expressing the human opioid receptor-like (ORL-1) receptor (Perkin Elmer, Boston, Mass.) are prepared by lysing cells in ice-cold hypotonic buffer (2.5 mM MgCl$_2$, 50 mM HEPES, pH 7.4) (10 mL/10 cm dish), followed by homogenization with a tissue grinder/teflon pestle. Membranes are collected by centrifugation at 30,000×g for 15 min at 4° C., and pellets are resuspended in hypotonic buffer to a final concentration of 1-3 mg/mL. Protein concentrations are determined using the BioRad (Hercules, Calif.) protein assay reagent with bovine serum albumen as standard. Aliquots of the ORL-1 receptor membranes are stored at −80° C.

μ- and ORL-1-Receptor-Binding-Assay Procedures

Radioligand dose-displacement binding assays for ORL-1 and μ receptors use 0.1 nM [$^3$H]-nociceptin or 0.2 nM [$^3$H]-diprenorphine (NEN, Boston, Mass.), respectively, with 5-20 mg membrane protein/well in a final volume of 500 ml binding buffer (10 mM MgCl$_2$, 1 mM EDTA, 5% DMSO, 50 mM HEPES, pH 7.4). Reactions are carried out in the absence or presence of increasing concentrations of unlabeled nociceptin (American Peptide Company, Sunnyvale, Calif.) or naloxone, for ORL-1 and μ, respectively. All reactions are conducted in 96-deep well polypropylene plates for 1-2 h at room temperature. Binding reactions are terminated by rapid filtration onto 96-well Unifilter GF/C filter plates (Packard, Meriden, Conn.) presoaked in 0.5% polyethylenimine using a 96-well tissue harvester (Brandel, Gaithersburg, Md.) followed performing by three filtration washes with 500 μL of ice-cold binding buffer. Filter plates are subsequently dried at 50° C. for 2-3 h. BetaScint scintillation cocktail (Wallac, Turku, Finland) is added (50 μl/well), and plates are counted using a Packard Top-Count for 1 min/well. The data are analyzed using the one-site competition curve fitting functions in GraphPad PRISM v. 3.0 (San Diego, Calif.).

5.9.2 μ-Receptor-Binding Data

Generally, the lower the Ki value, the more effective the 4-Tetrazolyl-4-phenylpiperidine Compounds are at treating or preventing pain or diarrhea. Typically, the 4-Tetrazolyl-4-phenylpiperidine Compounds will have a Ki (nM) of about 300 or less for binding to μ-opioid receptors. In one embodiment, the 4-Tetrazolyl-4-phenylpiperidine compounds will have a Ki (nM) of about 100 or less. In another embodiment, the 4-Tetrazolyl-4-phenylpiperidine Compounds of the present invention will have a Ki (nM) of about 10 or less. In still another embodiment, the 4-Tetrazolyl-4-phenylpiperidine Compounds will have a Ki (nM) of about 1 or less. In still another embodiment, the 4-Tetrazolyl-4-phenylpiperidine Compounds will have a Ki (nM) of about 0.1 or less. Compound AFD, an illustrative 4-Tetrazolyl-4-phenylpiperidine Compound, has a Ki (nM) of 3.2 for binding to μ-opioid receptors.

5.9.3 ORL-1-Receptor-Binding Data

Generally, the lower the Ki value, the more effective the 4-Tetrazolyl-4-phenylpiperidine Compounds are at treating or preventing pain or diarrhea. Typically, the 4-Tetrazolyl-4-phenylpiperidine Compounds will have a Ki (nM) of about 10,000 or less for ORL-1 receptors. In one embodiment, the 4-Tetrazolyl-4-phenylpiperidine Compounds will have a Ki (nM) of about 2000 or less. In another embodiment, the 4-Tetrazolyl-4-phenylpiperidine Compounds will have a Ki (nM) of about 1000 or less. In still another embodiment, the 4-Tetrazolyl-4-phenylpiperidine Compounds will have a Ki (nM) of about 100 or less. In still another embodiment, the 4-Tetrazolyl-4-phenylpiperidine Compounds will have a Ki (nM) of about 10 or less.

5.10 Example 23

μ- and ORL-1-Opioid Receptor γS Functional Activity

The following example will demonstrate that 4-Tetrazolyl-4-phenylpiperidine Compounds stimulate μ- or ORL-1-receptor function and, accordingly, are useful for treating or preventing pain or diarrhea.

5.10.1 Materials and Methods

[$^{35}$S]GTPγS functional assays are conducted using freshly thawed ORL-1 or -receptor membranes, as appropriate. Assay reactions are prepared by sequentially adding the following reagents to binding buffer (100 mM NaCl, 10 mM MgCl$_2$, 20 mM HEPES, pH 7.4) on ice (final concentrations indicated): membrane protein (0.066 mg/mL for ORL-1 receptor and 0.026 mg/mL for μ-receptor), saponin (10 mg/ml), GDP (3 mM) and [$^{35}$S]GTPγS (0.20 nM; NEN). The prepared membrane solution (190 μL/well) is transferred to 96-shallow well polypropylene plates containing 10 μL of 20× concentrated stock solutions of the agonist nociceptin prepared in dimethyl sulfoxide ("DMSO"). Plates are incubated for 30 min at room temperature with shaking. Reactions are terminated by rapid filtration onto 96-well Unifilter GF/B filter plates (Packard, Meriden, Conn.) using a 96-well tissue harvester (Brandel, Gaithersburg, Md.) followed by three filtration washes with 200 μL of ice-cold binding buffer (10 mM NaH$_2$PO$_4$, 10 mM Na$_2$HPO$_4$, pH 7.4). Filter plates are subsequently dried at 50° C. for 2-3 h. BetaScint scintillation cocktail (Wallac, Turku, Finland) is added (50 μL/well) and plates are counted using a Packard Top-Count for 1 min/well. Data are analyzed using the sigmoidal dose-response curve fitting functions in GraphPad PRISM, v. 3.0.

5.10.2 μ-Receptor Function Data

μ GTP EC$_{50}$ is the concentration of a compound providing 50% of the maximal response for the compound at a μ receptor. 4-Tetrazolyl-4-phenylpiperidine Compounds typically having a μ GTP EC$_{50}$ (nM) of about 5000 or less stimulate μ opioid receptor function. In one embodiment, the 4-Tetrazolyl-4-phenylpiperidine Compounds will have a μ GTP EC$_{50}$ (nM) of about 1000 or less. In still another embodiment, the 4-Tetrazolyl-4-phenylpiperidine Compounds will have a μ GTP EC$_{50}$ (nM) of about 100 or less. In still another embodiment, the 4-Tetrazolyl-4-phenylpiperidine Compounds will have a μ GTP EC$_{50}$ (nM) of about 10 or less. In still another embodiment, the 4-Tetrazolyl-4-phenylpiperidine Compounds will have a μ GTP EC$_{50}$ (nM) of about 1 or less. In still another embodiment, the 4-Tetrazolyl-4-phenylpiperidine Compounds will have a μ GTP EC$_{50}$ (nM) of about 0.1 or less.

μ GTP Emax % is the maximal effect elicited by a compound relative to the effect elicited by [D-Ala2, N-methyl-Phe4, Gly-ol5]-enkephalin ("DAMGO"), a standard 1 agonist. Generally, the μ GTP Emax (%) value measures the efficacy of a compound to treat or prevent pain or diarrhea. Typically the 4-Tetrazolyl-4-phenylpiperidine Compounds will have a μ GTP Emax (%) of greater than 50%. In one embodiment the 4-Tetrazolyl-4-phenylpiperidine Compounds will have a μ GTP Emax (%) of greater than 75%. In still another embodiment the 4-Tetrazolyl-4-phenylpiperidine Compounds will have a μ GTP Emax (%) of greater than 88%. In still another embodiment the 4-Tetrazolyl-4-phenylpiperidine Compounds will have a μ GTP Emax (%) of greater than 100%.

5.10.3 ORL-1-Receptor Function Data

ORL-1 GTP EC$_{50}$ is the concentration of a compound providing 50% of the maximal response for the compound at an ORL-1 receptor. 4-Tetrazolyl-4-phenylpiperidine Compounds having a ORL-1 GTP EC$_{50}$ (nM) of about 10,000 or less stimulate ORL-1 opioid-receptor function. In one embodiment, the 4-Tetrazolyl-4-phenylpiperidine Compounds will have a ORL-1 GTP EC$_{50}$ (nM) of about 1000 or less. In still another embodiment, the 4-Tetrazolyl-4-phenylpiperidine Compounds will have a ORL-1 GTP EC$_{50}$ (nM) of about 100 or less. In still another embodiment, the 4-Tetrazolyl-4-phenylpiperidine Compounds will have a ORL-1 GTP EC$_{50}$ (nM) of about 50 or less. In still another embodiment, the 4-Tetrazolyl-4-phenylpiperidine Compounds will have a ORL-1 GTP EC$_{50}$ (nM) of about 10 or less.

ORL-1 GTP Emax % is the maximal effect elicited by a compound relative to the effect elicited by nociceptin, a standard ORL-1 agonist. Generally, the ORL-1 GTP Emax (%) value measures the efficacy of a compound to treat or prevent pain or diarrhea. Typically the 4-Tetrazolyl-4-phenylpiperidine Compounds have a ORL-1 GTP Emax (%) of greater than 50%. In one embodiment the 4-Tetrazolyl-4-phenylpiperidine Compounds will have a ORL-1 GTP Emax (%) of greater than 75%. In still another embodiment the 4-Tetrazolyl-4-phenylpiperidine Compounds will have a ORL-1 GTP Emax (%) of greater than 88%. In still another embodiment the 4-Tetrazolyl-4-phenylpiperidine Compounds will have a ORL-1 GTP Emax (%) of greater than 100%.

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited, the entire disclosures of which are incorporated herein by reference.

What is claimed is:

1. A method of treating pain in an animal, comprising administering to an animal in need thereof an effective amount of a compound or a pharmaceutically acceptable salt of a compound of formula (Ia):

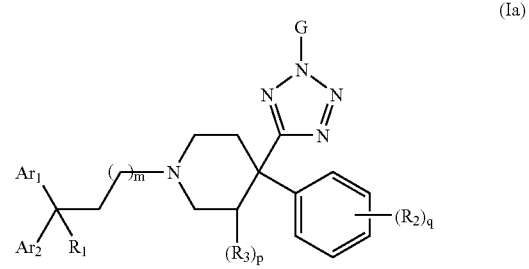

(Ia)

wherein
- Ar₁ is $C_3$-$C_8$ cycloalkyl, phenyl, naphthyl, anthryl, phenanthryl or -(5- to 7-membered) heteroaryl, each being unsubstituted or substituted with one or more $R_2$ groups;
- Ar₂ is phenyl, naphthyl, anthryl, phenanthryl or -(5- to 7-membered) heteroaryl, each being unsubstituted or substituted with one or more $R_2$ groups;
- G is —H, -L-$(CH_2)_n CO_2R_4$, -L-$(CH_2)_n R_5$, —$(C_1$-$C_5$ alkylene)$CO_2R_4$, or —$(C_1$-$C_5$ alkylene)$R_5$;
- L=—C(O)—, —SO₂— or —SO—;
- R₁=H, —C(O)NH₂, —C(O)NHOH, —CO₂R₄, —CHO, —CN, —($C_1$-$C_4$ alkyl), —C(O)NH($C_1$-$C_4$ alkyl), or —C(O)N($C_1$-$C_4$ alkyl)₂;
- R₂ and R₃ are each independently -halogen, —$C_1$-$C_3$ alkyl, —O($C_1$-$C_3$ alkyl), —NH($C_1$-$C_3$ alkyl) or —N($C_1$-$C_3$ alkyl)₂;
- R₄=—H, —$C_1$-$C_{10}$ alkyl, —$CH_2O$($C_1$-$C_4$ alkyl), —$CH_2N$($C_1$-$C_4$ alkyl)₂, or —$CH_2NH$($C_1$-$C_4$ alkyl);
- R₅=—NH₂, —NHSO₂R₄, —C(O)NH₂, —C(O)NHOH, —SO₂NH₂, —C(O)NH($C_1$-$C_4$ alkyl), —C(O)N($C_1$-$C_4$ alkyl)₂, —SO₂NH($C_1$-$C_4$ alkyl), —SO₂N($C_1$-$C_4$ alkyl)₂, —H, —OH, —CN, —$C_3$-$C_8$ cycloalkyl, phenyl, naphthyl, anthryl, phenanthryl, or -(5- to 7-membered) heteroaryl, each being unsubstituted or substituted with one or more $R_2$ groups;
- m=an integer ranging from 0 to 4;
- n=an integer ranging from 1 to 4;
- p=0 or 1; and
- q=an integer ranging from 0 to 3.

2. The method of claim 1, further comprising administering an effective amount of an opioid analgesic.

3. The method of claim 1, further comprising administering an effective amount of a non-opioid analgesic.

4. The method of claim 1, further comprising administering an effective amount of an anti-emetic agent.

5. A method for stimulating opioid-receptor function in a cell comprising contacting a cell capable of expressing an opioid receptor with an effective amount of a compound or a pharmaceutically acceptable salt of a compound of formula (Ia):

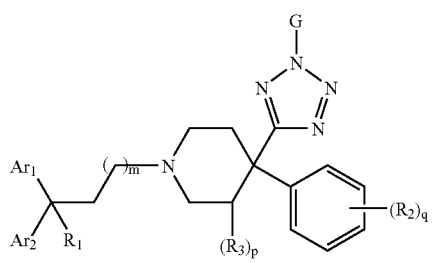

(Ia)

wherein
- Ar₁ is $C_3$-$C_8$ cycloalkyl, phenyl, naphthyl, anthryl, phenanthryl or -(5- to 7-membered) heteroaryl, each being unsubstituted or substituted with one or more $R_2$ groups;
- Ar₂ is phenyl, naphthyl, anthryl, phenanthryl or -(5- to 7-membered) heteroaryl, each being unsubstituted or substituted with one or more $R_2$ groups;
- G is —H, -L-$(CH_2)_n CO_2R_4$, -L-$(CH_2)_n R_5$, —$(C_1$-$C_5$ alkylene)$CO_2R_4$, or —$(C_1$-$C_5$ alkylene)$R_5$;
- L=—C(O)—, —SO₂— or —SO—;
- R₁=H, —C(O)NH₂, —C(O)NHOH, —CO₂R₄, —CHO, —CN, —($C_1$-$C_4$ alkyl), —C(O)NH($C_1$-$C_4$ alkyl), or —C(O)N($C_1$-$C_4$ alkyl)₂;
- R₂ and R₃ are each independently -halogen, —$C_1$-$C_3$ alkyl, —O($C_1$-$C_3$ alkyl), —NH($C_1$-$C_3$ alkyl) or —N($C_1$-$C_3$ alkyl)₂;
- R₄=—H, —$C_1$-$C_{10}$ alkyl, —$CH_2O$($C_1$-$C_4$ alkyl), —$CH_2N$($C_1$-$C_4$ alkyl)₂, or —$CH_2NH$($C_1$-$C_4$ alkyl);
- R₅=—NH₂, —NHSO₂R₄, —C(O)NH₂, —C(O)NHOH, —SO₂NH₂, —C(O)NH($C_1$-$C_4$ alkyl), —C(O)N($C_1$-$C_4$ alkyl)₂, —SO₂NH($C_1$-$C_4$ alkyl), —SO₂N($C_1$-$C_4$ alkyl)₂, —H, —OH, —CN, —$C_3$-$C_8$ cycloalkyl, phenyl, naphthyl, anthryl, phenanthryl, or -(5- to 7-membered) heteroaryl, each being unsubstituted or substituted with one or more $R_2$ groups;
- m=an integer ranging from 0 to 4;
- n=an integer ranging from 1 to 4;
- p=0 or 1; and
- q=an integer ranging from 0 to 3.

6. The method of claim 5, wherein the receptor is selected from the group consisting of a κ-opioid receptor, a μ-opioid receptor, a δ-opioid receptor, and an ORL-1 receptor.

7. A method of treating diarrhea in an animal, comprising administering to an animal in need thereof an effective amount of a compound or a pharmaceutically acceptable salt of a compound of formula (Ia):

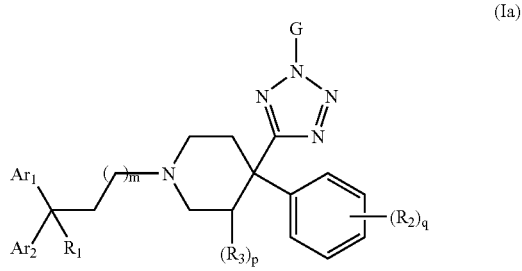

(Ia)

wherein
- Ar₁ is —$C_3$-$C_8$ cycloalkyl, phenyl, naphthyl, anthryl, phenanthryl or -(5- to 7-membered) heteroaryl, each being unsubstituted or substituted with one or more $R_2$ groups;
- Ar₂ is phenyl, naphthyl, anthryl, phenanthryl or -(5- to 7-membered) heteroaryl, each being unsubstituted or substituted with one or more $R_2$ groups;
- G is —H, -L-$(CH_2)_n CO_2R_4$, -L-$(CH_2)_n R_5$, —$(C_1$-$C_5$ alkylene)$CO_2R_4$, or —$(C_1$-$C_5$ alkylene)$R_5$;
- L=—C(O)—, —SO₂— or —O—; R₁=H, —C(O)NH₂, —C(O)NHOH, —CO₂R₄, —CHO, —CN, —($C_1$-$C_4$ alkyl), —C(O)NH($C_1$-$C_4$ alkyl), or —C(O)N($C_1$-$C_4$ alkyl)₂;
- R₂ and R₃ are each independently -halogen, —$C_1$-$C_3$ alkyl, —O($C_1$-$C_3$ alkyl), —NH($C_1$-$C_3$ alkyl) or —N($C_1$-$C_3$ alkyl)₂;
- R₄=—H, —$C_1$-$C_{10}$ alkyl, —$CH_2O$($C_1$-$C_4$ alkyl), —$CH_2N$($C_1$-$C_4$ alkyl)₂, or $CH_2NH$($C_1$-$C_4$ alkyl);
- R₅=—NH₂, —NHSO₂R₄, —C(O)NH₂, —C(O)NHOH, —SO₂NH₂, —C(O)NH($C_1$-$C_4$ alkyl), —C(O)N($C_1$-$C_4$ alkyl)₂, —SO₂NH($C_1$-$C_4$ alkyl), —SO₂N($C_1$-$C_4$ alkyl)₂, —H, —OH, —CN, —$C_3$-$C_8$ cycloalkyl, phenyl, naphthyl, anthryl, phenanthryl, or -(5 to 7-membered) heteroaryl, each being unsubstituted or substituted with one or more $R_2$ groups;
- m=an integer ranging from 0 to 4;

n=an integer ranging from 1 to 4;
p=0 or 1; and
q=an integer ranging from 0 to 3.

8. The method of claim 7, further comprising administering an effective amount of an opioid analgesic.

9. The method of claim 7, further comprising administering an effective amount of a non-opioid analgesic.

10. The method of claim 7, further comprising administering an effective amount of an anti-emetic agent.

11. A method of treating pain in an animal, comprising administering to an animal in need thereof an effective amount of a compound or a pharmaceutically acceptable salt of a compound of formula (Ib):

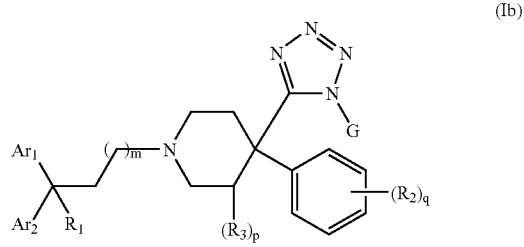

(Ib)

wherein
$Ar_1$ is —$C_3$-$C_8$ cycloalkyl, phenyl, naphthyl, anthryl, phenanthryl or -(5- to 7-membered) heteroaryl, each being unsubstituted or substituted with one or more $R_2$ groups;
$Ar_2$ is phenyl, naphthyl, anthryl, phenanthryl or -(5- to 7-membered) heteroaryl, each being unsubstituted or substituted with one or more $R_2$ groups;
G is —H, -L-$(CH_2)_n CO_2 R_4$, -L-$(CH_2)_n R_5$, —$(C_1$-$C_5$ alkylene)$CO_2 R_4$, or $(C_1$-$C_5$ alkylene)$R_5$;
L=—C(O)—, —$SO_2$— or —SO—;
$R_1$=H, —C(O)$NH_2$, —C(O)NHOH, —$CO_2 R_4$, —CHO, —CN, —($C_1$-$C_4$ alkyl), —C(O)NH($C_1$-$C_4$ alkyl), or —C(O)N($C_1$-$C_4$ alkyl)$_2$;
$R_2$ and $R_3$ are each independently -halogen, —$C_1$-$C_3$ alkyl, —O($C_1$-$C_3$ alkyl), —NH($C_1$-$C_3$ alkyl) or —N($C_1$-$C_3$ alkyl)$_2$;
$R_4$=—H, —$C_1$-$C_{10}$ alkyl, —$CH_2$O($C_1$-$C_4$ alkyl), —$CH_2$N($C_1$-$C_4$ alkyl)$_2$, or —$CH_2$NH($C_1$-$C_4$ alkyl);
$R_5$=—$NH_2$, —$NHSO_2 R_4$, —C(O)$NH_2$, —C(O)NHOH, —$SO_2 NH_2$, —C(O)NH($C_1$-$C_4$ alkyl), —C(O)N($C_1$-$C_4$ alkyl)$_2$, —$SO_2$NH($C_1$-$C_4$ alkyl), —$SO_2$N($C_1$-$C_4$ alkyl)$_2$, —H, —OH, —CN, —$C_3$-$C_8$ cycloalkyl, phenyl, naphthyl, anthryl, phenanthryl, or -(5- to 7-membered) heteroaryl, each being unsubstituted or substituted with one or more $R_2$ groups;
m=an integer ranging from 0 to 4;
n=an integer ranging from 1 to 4;
p=0 or 1; and
q=an integer ranging from 0 to 3.

12. The method of claim 11, further comprising administering an effective amount of an opioid analgesic.

13. The method of claim 11, further comprising administering an effective amount of a non-opioid analgesic.

14. The method of claim 11, further comprising administering an effective amount of an anti-emetic agent.

15. A method for stimulating opioid-receptor function in a cell comprising contacting a cell capable of expressing an opioid receptor with an effective amount of a compound or a pharmaceutically acceptable salt of a compound of formula (Ib):

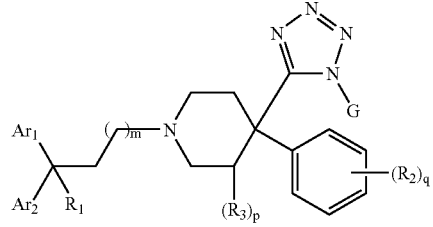

(Ib)

wherein
$Ar_1$ is —$C_3$-$C_8$ cycloalkyl, phenyl, naphthyl, anthryl, phenanthryl or -(5- to 7-membered) heteroaryl, each being unsubstituted or substituted with one or more $R_2$ groups;
$Ar_2$ is phenyl, naphthyl, anthryl, phenanthryl or -(5- to 7-membered) heteroaryl, each being unsubstituted or substituted with one or more $R_2$ groups;
G is —H, -L-$(CH_2)_n CO_2 R_4$, -L-$(CH_2)_n R_5$, —$(C_1$-$C_5$ alkylene)$CO_2 R_4$, or $(C_1$-$C_5$ alkylene)$R_5$;
L=—C(O)—, —$SO_2$— or —SO—;
$R_1$=H, —C(O)$NH_2$, —C(O)NHOH, —$CO_2 R_4$, —CHO, —CN, —($C_1$-$C_4$ alkyl), —C(O)NH($C_1$-$C_4$ alkyl), or —C(O)N($C_1$-$C_4$ alkyl)$_2$;
$R_2$ and $R_3$ are each independently -halogen, —$C_{1-C3}$ alkyl, —O($C_1$-$C_3$ alkyl), —NH($C_1$-$C_3$ alkyl) or —N($C_1$-$C_3$ alkyl)$_2$;
$R_4$=—H, —$C_1$-$C_{10}$ alkyl, —$CH_2$O($C_1$-$C_4$ alkyl), —$CH_2$N($C_1$-$C_4$ alkyl)$_2$, or —$CH_2$NH($C_1$-$C_4$ alkyl);
$R_5$=—$NH_2$, —$NHSO_2 R_4$, —C(O)$NH_2$, —C(O)NHOH, —$SO_2 NH_2$, —C(O)NH($C_1$-$C_4$ alkyl), —C(O)N($C_1$-$C_4$ alkyl)$_2$, —$SO_2$NH($C_1$-$C_4$ alkyl), —$SO_2$NH($C_1$-$C_4$ alkyl)$_2$, —H, —OH, —CN, —$C_3$-$C_8$ cycloalkyl, phenyl, naphthyl, anthryl, phenanthryl, or -(5- to 7-membered) heteroaryl, each being unsubstituted or substituted with one or more $R_2$ groups;
m=an integer ranging from 0 to 4;
n=an integer ranging from 1 to 4;
p=0 or 1; and
q=an integer ranging from 0 to 3.

16. The method of claim 15, wherein the receptor is selected from the group consisting of a κ-opioid receptor, a μ-opioid receptor, a δ-opioid receptor, and an ORL-1 receptor.

17. A method of treating diarrhea in an animal, comprising administering to an animal in need thereof an effective amount of a compound or a pharmaceutically acceptable salt of a compound of formula (Ib):

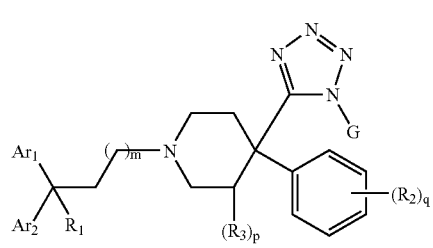

(Ib)

wherein
$Ar_1$ is —$C_3$-$C_8$ cycloalkyl, phenyl, naphthyl, anthryl, phenanthryl or -(5- to 7-membered) heteroaryl, each being unsubstituted or substituted with one or more $R_2$ groups;

Ar$_2$ is phenyl, naphthyl, anthryl, phenanthryl or (5- to 7-membered) heteroaryl, each being unsubstituted or substituted with one or more R$_2$ groups;

G is —H, -L-(CH$_2$)$_n$CO$_2$R$_4$, -L-(CH$_2$)$_n$R$_5$, —(C$_1$-C$_5$ alkylene)CO$_2$R$_4$, or (C$_1$-C$_5$ alkylene)R$_5$;

L=—C(O)—, —SO$_2$— or —SO—;

R$_1$=H, —C(O)NH$_2$, —C(O)NHOH, —CO$_2$R$_4$, —CHO, —CN, —(C$_1$-C$_4$ alkyl), —C(O)NH(C$_1$-C$_4$ alkyl), or —C(O)N(C$_1$-C$_4$ alkyl)$_2$;

R$_2$ and R$_3$ are each independently -halogen, —C$_1$-C$_3$ alkyl, —O(C$_1$-C$_3$ alkyl), —NH(C$_1$-C$_3$ alkyl) or —N(C$_1$-C$_3$ alkyl)$_2$;

R$_4$=—H, —C$_1$-C$_{10}$ alkyl, —CH$_2$O(C$_1$-C$_4$ alkyl), —CH$_2$N(C$_1$-C$_4$ alkyl)$_2$, or —CH$_2$NH(C$_1$-C$_4$ alkyl);

R$_5$=—NH$_2$, —NHSO$_2$R$_4$, —C(O)NH$_2$, —C(O)NHOH, —SO$_2$NH$_2$, —C(O)NH(C$_1$-C$_4$ alkyl), —C(O)N(C$_1$-C$_4$ alkyl)$_2$, —SO$_2$NH(C$_1$-C$_4$ alkyl), —SO$_2$N(C$_1$-C$_4$ alkyl)$_2$, —H, —OH, —CN, —C$_3$-C$_8$ cycloalkyl, phenyl, naphthyl, anthryl, phenanthryl, or -(5- to 7-membered) heteroaryl, each being unsubstituted or substituted with one or more R$_2$ groups;

m=an integer ranging from 0 to 4;

n=an integer ranging from 1 to 4;

p=0 or 1; and q=an integer ranging from 0 to 3.

18. The method of claim 17, further comprising administering an effective amount of an opioid analgesic.

19. The method of claim 17, further comprising administering an effective amount of a non-opioid analgesic.

20. The method of claim 17, further comprising administering an effective amount of an anti-emetic agent.

21. The method of claim 1, 5, or 7, wherein the compound of formula (Ia) is selected from the group consisting of

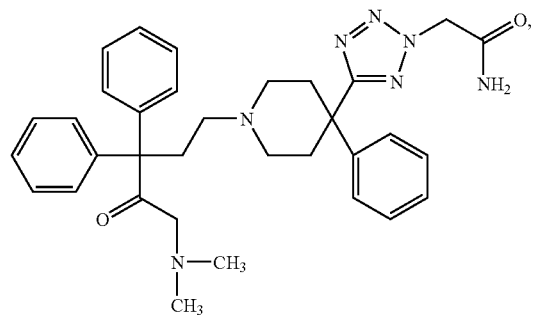

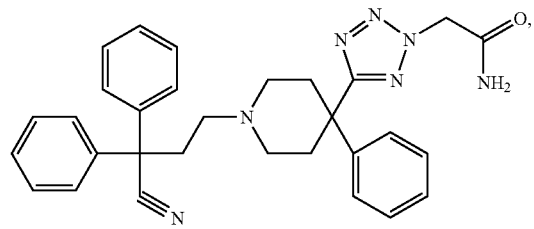

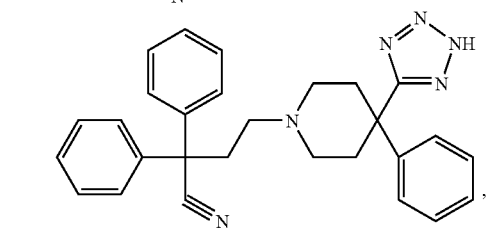

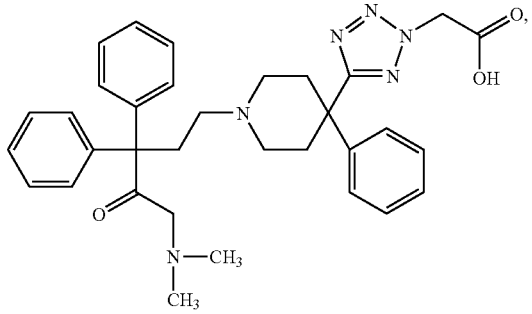

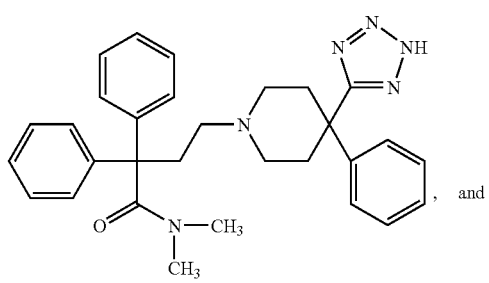

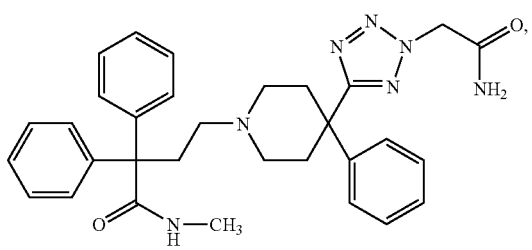

and pharmaceutical salts thereof.

22. The method of claim 21, wherein the compound of formula (Ia) is selected from the group consisting of

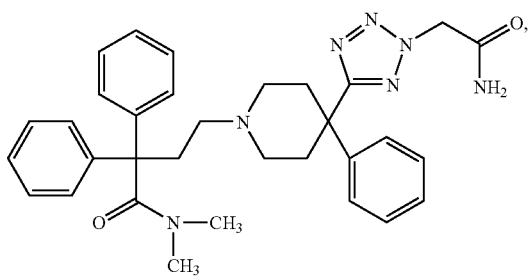

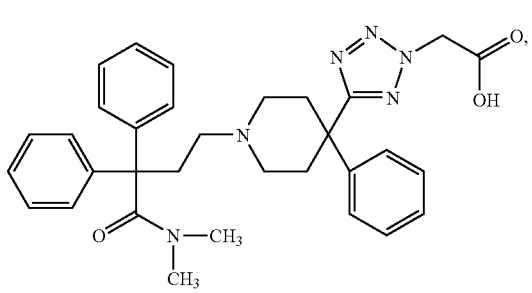

-continued
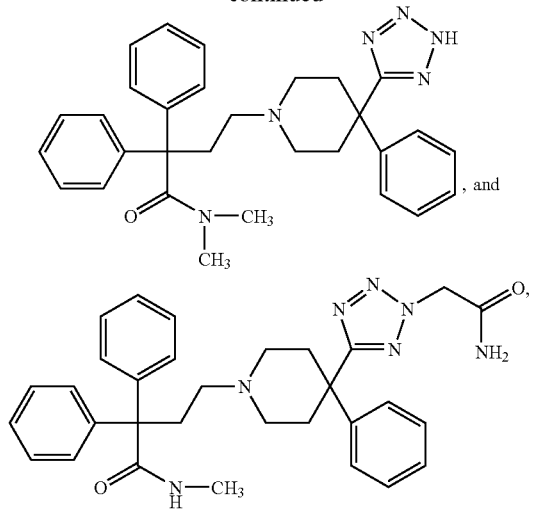
and pharmaceutical thereof.
23. The method of claim 22, wherein the compound of formula (Ia) is
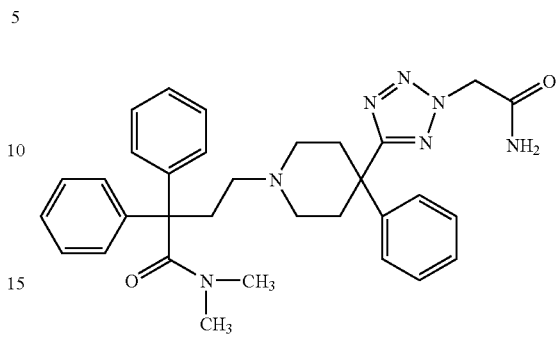
or a pharmaceutical salt thereof.
* * * * *

UNITED STATES PATENT AND TRADEMARK OFFICE
CERTIFICATE OF CORRECTION

PATENT NO. : 7,687,518 B2  Page 1 of 2
APPLICATION NO. : 11/729660
DATED : March 30, 2010
INVENTOR(S) : Zhengming Chen It is certified that error appears in the above-identified patent and that said Letters Patent is hereby corrected as shown below:

In column 104, line 51, claim 7, "-O-" should read -- -SO- --.

In column 106, line 27, claim 15, "-$C_{1-C3}$ alkyl," should read -- -$C_1$-$C_3$ alkyl, --.

In column 107, line 45, claim 21, " 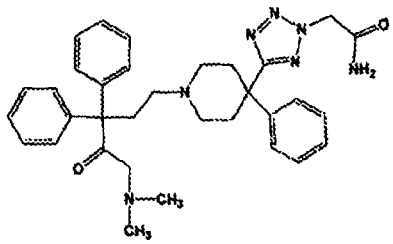 " should read

-- 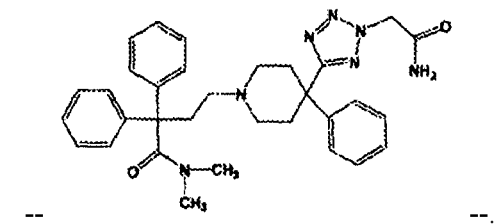 --.

In column 108, line 10, claim 21, " 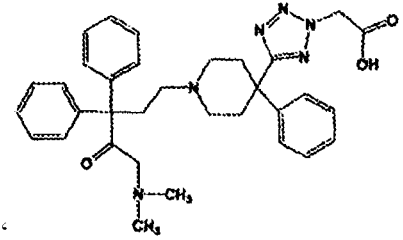 " should read

Signed and Sealed this

First Day of June, 2010

David J. Kappos
*Director of the United States Patent and Trademark Office*

CERTIFICATE OF CORRECTION (continued)
U.S. Pat. No. 7,687,518 B2

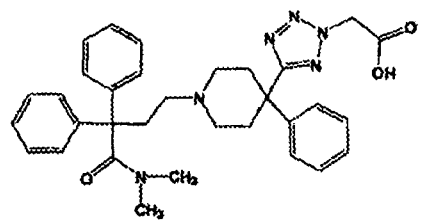

-- --.

In column 109, line 23, claim 22, "pharmaceutical" should read -- pharmaceutical salts --.